(12) United States Patent
Jia et al.

(10) Patent No.: US 12,042,523 B2
(45) Date of Patent: *Jul. 23, 2024

(54) COMPOSITIONS AND METHODS FOR MANAGING OR IMPROVING BONE DISORDERS, JOINT DISORDERS, CARTILAGE DISORDERS, OR A COMBINATION THEREOF

(71) Applicant: Unigen, Inc., Tacoma, WA (US)

(72) Inventors: Qi Jia, Seattle, WA (US); Ping Jiao, Seattle, WA (US); Mesfin Yimam, Seattle, WA (US); Teresa Horm, Seattle, WA (US)

(73) Assignee: Unigen, Inc., Tacoma, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/084,009

(22) Filed: Dec. 19, 2022

(65) Prior Publication Data

US 2023/0201295 A1 Jun. 29, 2023

Related U.S. Application Data

(63) Continuation of application No. 16/812,899, filed on Mar. 9, 2020, now Pat. No. 11,554,153, which is a continuation of application No. 15/808,580, filed on Nov. 9, 2017, now Pat. No. 10,583,161, which is a continuation-in-part of application No. 15/663,793, filed on Jul. 30, 2017, now abandoned, which is a continuation of application No. 14/741,221, filed on Jun. 16, 2015, now Pat. No. 9,717,770.

(60) Provisional application No. 62/419,740, filed on Nov. 9, 2016, provisional application No. 62/012,958, filed on Jun. 16, 2014.

(51) Int. Cl.
*A61K 36/00* (2006.01)
*A61K 31/352* (2006.01)
*A61K 31/353* (2006.01)
*A61K 31/7034* (2006.01)
*A61K 36/48* (2006.01)
*A61K 36/605* (2006.01)

(52) U.S. Cl.
CPC .......... *A61K 36/605* (2013.01); *A61K 31/352* (2013.01); *A61K 31/353* (2013.01); *A61K 31/7034* (2013.01); *A61K 36/48* (2013.01); *A61K 2300/00* (2013.01)

(58) Field of Classification Search
CPC .................................................. A61K 36/605
See application file for complete search history.

(56) References Cited

U.S. PATENT DOCUMENTS 7,514,469 B2 * 4/2009 Jia .......................... A61K 36/54
514/456

FOREIGN PATENT DOCUMENTS

JP 411147834 A * 6/1999

OTHER PUBLICATIONS

Cheon et al, Effects of prenylated flavonoids and bioflavonoids on lipopolysaccharide-induced nitric oxide production from the mouse macrophage cell line RAW 264.7. Planta Medica (2000), vol. 66, No. 7, pp. 596-600 (Year: 2000).*

* cited by examiner

*Primary Examiner* — Qiuwen Mi
(74) *Attorney, Agent, or Firm* — Dr. Sandra Poteat Thompson; Finlayson Toffer

(57) ABSTRACT

Compositions and methods for bone health, cartilage health or both, are disclosed that include preparing and utilizing a mixture of at least one *Morus* extract enriched for one or more prenylated flavonoids, at least one *Scutellaria* extract enriched for one or more free-B-ring flavonoids, and at least one *Acacia* extract enriched for one or more flavans.

11 Claims, 1 Drawing Sheet

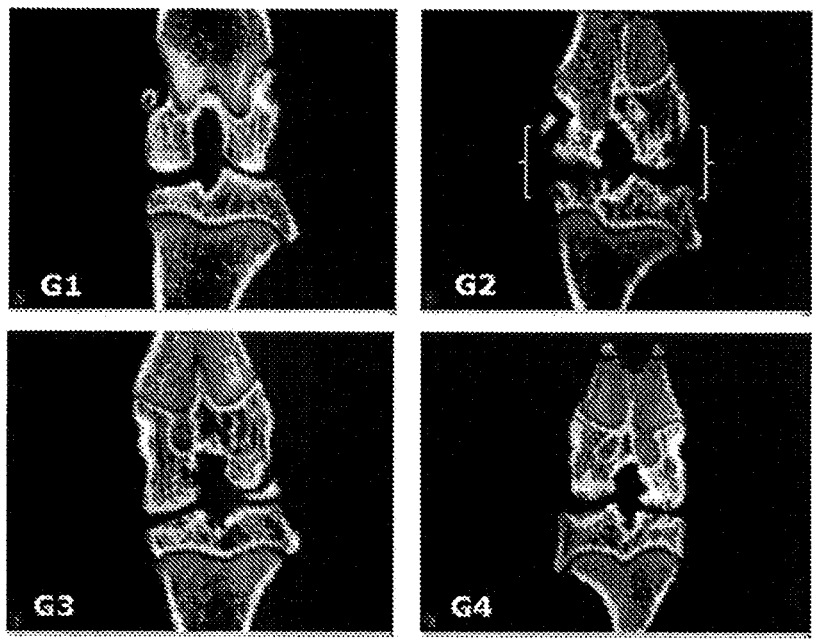

COMPOSITIONS AND METHODS FOR MANAGING OR IMPROVING BONE DISORDERS, JOINT DISORDERS, CARTILAGE DISORDERS, OR A COMBINATION THEREOF

This application claims priority to U.S. Utility application Ser. No. 16/812,899 entitled "Compositions and Methods for Managing or Improving Bone Disorders, Joint Disorders, Cartilage Disorders, or a Combination Thereof" filed on Mar. 9, 2020, which claims priority to U.S. Utility application Ser. No. 15/808,580 entitled "Compositions and Methods for Managing or Improving Bone Disorders, Joint Disorders, Cartilage Disorders, or a Combination Thereof" filed on Nov. 9, 2017; which claims priority to "U.S. Provisional Application Ser. No. 62/419,740 entitled "Morus, Scutellaria and Acacia Composition for Reduction of Arthritis Biomarker uCTX-II", which was filed on Nov. 9, 2016; and is also a continuation in part application of U.S. application Ser. No. 15/663,793, which is a continuation application of U.S. Ser. No. 14/741,221 entitled "Compositions and Methods for Managing or Improving Bone Disorders, Cartilage Disorders, or Both" and filed on Jun. 16, 2015, which claims priority to U.S. Provisional Patent Application Ser. No. 62/012,958 filed on Jun. 16, 2014, all of which are incorporated herein by reference in their entirety.

BACKGROUND OF THE SUBJECT MATTER

Reduced bone density, which often evolves into osteoporosis in aging populations, especially pre- and post-menopausal women, is an important health concern. Osteoporosis is defined clinically through the measurement of bone mineral density (BMD), which remains the best predictor of primary osteoporotic fractures (Kanis et al., *Osteoporos. Int.* 16:581, 2005). Systemic inflammation is frequently associated with accelerated bone reabsorption, which leads to bone loss. Various mechanisms, such as elevated PGE2, TNF-α, IL-1β and other pro-inflammatory cytokines, have been proposed to be involved with bone loss under inflammatory conditions (Hardy and Cooper, *J. Endocrinol.* 201:309, 2009).

It has been shown that NSAIDs inhibit the COX enzyme and decrease production of prostaglandins, which are involved in the regulation of bone turnover (Raisz et al., *Osteoporos. Int.* 3(Suppl 1):136, 1993). The use of cyclooxygenase-2 (COX-2) inhibitors has been demonstrated not only to impair load-induced bone formation, but also to prevent menopause-associated BMD loss (Richards et al., *Osteoporos. Int.* 17:1410, 2006). For example, diclofenac is an NSAID that inhibits both COX-1 and COX-2 enzymes (Richards et al., 2006). In a human clinical trial, diclofenac was almost as effective as conjugated estrogens for protection of bone loss in postmenopausal women (Bruce et al., *Am. J. Med.* 96:349, 1994). Cottrell et al. (*Bone Joint Res.* 2:41, 2013), have reported that a 5-lipoxygenase (LOX) inhibitor can enhance bone regeneration in an animal model. In human clinical trials in postmenopausal women, regular use of the combination of a COX-2 selective NSAID and aspirin has been shown to result in higher BMD at all skeletal sites, including whole body and total hip, as measured by bone density scanning (DXA) and both trabecular and cortical BMD of the lumbar spine by quantitative computer tomography (QCT) (Carbone et al., *J. Bone Miner. Res.* 18:1795, 2003).

Osteoarthritis (OA), characterized by progressive degeneration of articular cartilage, osteophyte formation, and subsequent joint space narrowing, is the most common form of arthritis that affects an estimated 30.8 million adult population in the US (Cisternas et al., 2016). Despite recent advances in drug discovery, present-day OA management is inadequate due to the lack of primary therapies proven to be effective in modifying disease progression. The current approach focuses mainly on curtailing the sensitivity of disease associated pain (like use of over the counter Non-steroidal anti-inflammatory drugs, NSAIDs), which will only mask the actual etiology leading to irreversible damage to the articular structure. In addition, chronic usages of NSAIDs for symptomatic relief of OA are also limited due to their gastrointestinal, renal and cardiovascular side effects (Bozimowski et al., 2015). As a result, there always is the need for a safe and efficacious natural alternative.

OA is a multifactorial disease with unspecified initial etiology involving articular cartilage, subchondral bone and synovial membrane. Cartilage is the main component of articular structure, and consists of chondrocytes that are embedded in a dense and highly organized extracellular matrix (ECM). ECM is synthesized by the chondrocytes, and is composed of a collagenous network that primarily contains type II collagen, along with glycosaminoglycans (GAGs) and associated proteoglycans. Pro-inflammatory cytokines such as tumor necrosis factor (TNF)-α and interleukin (IL)-1 are known to play important roles in cartilage matrix degradation in the articular cartilage through a cascade of events that lead to stimulation of aggrecanase and matrix metalloproteinase production (Kobayashi et al., 2005). Articular cartilage degradation could also occur as a result of an imbalance in the homeostasis of these fundamental matrix components such as GAGs and type II collagen (Bijlsma et al., 2011). This pathogenesis is triggered in part by the action of inflammatory cytokines, primarily IL-1 (Kapoor et al., 2011; Sandell et al., 2008) that also mediate the production of proinflammatory mediators (including NO and PGE2) and matrix degrading enzymes—aggrecanase and matrix metalloproteinase (MMP). While the catabolic enzymes, MMPs disrupt collagen fibers (Hollander et al., 1994), members of a disintegrin and metalloprotease with thrombospondin (ADAMTS) family degrade aggrecan and both cases result in the release of GAGs (Bondeson et al., 2008). Therefore, plant extracts with proven anti-inflammatory and/or anti-protease/aggrecanase activity could potentially be co-administered with other materials for their potential cartilage protection activity in OA patients.

It is believed that at various stages of OA, all three major structures of the joint (cartilage, subchondral bone and synovium) could be involved in the pathophysiology of the disease which complicates the identification of a single biomarker that is crucial for immediate therapeutic intervention at the early stage of the disease. Nevertheless, among all the major joint biomarkers proposed, C-terminal telopeptide of type II collagen (CTX-II) has been by far the most studied and frequently referred biomarker of cartilage degradation that could be used for the purpose of diagnosis, determining severity of disease or extent of disease progression, prognosis and monitoring efficacy of treatment. It is primarily generated by matrix metalloproteinase activity during cartilage degradation in OA. It is known to show a close link with progression of articular cartilage degradation in OA patients. It's correlation of increased serum, urine or synovial fluid level and articular cartilage degradation were reported both in pre-clinical and clinical studies (Oestergaard et al., 2006; Garnero et al., 2001). However, there is very limited reports suggesting that plant extracts with inherent characteristic of reducing CTX-II level to be also potentially administered for their cartilage protection activity.

One of the challenges for measurement of clinical efficacy of active agent for prevention and treatment of arthritis and for protection of joint and cartilage integrate heavily relies on subjective WOMAC questionnaires for symptom relieve and x-ray and other diagnostic instrument to measure joint space area and joint space narrowing, which requires significant number of subjects and many months long treatment. It is clinically relevant for finding novel natural compositions that can demonstrate modulation of objective clinical measurements such as CTX-II biomarkers associated with joint health.

Recently, we reported a botanical composition designated as UP1306 (a proprietary blend of two bioflavonoid standardized extracts from the heartwood of *Acacia catechu* and root bark of *Morus alba*) with analgesic and anti-inflammatory effects which was discovered through the in vivo screening of known traditional folk-medicines suggesting its usage for OA associated symptoms relief (Yimam, et al., 2016). UP1306, administered orally at a dose of 300 mg/kg, resulted in 46.3%-53.3% reductions in paw edema and 43.6%-54.8% reductions in pain sensitivity in the carrageenan induced rat paw edema model as well as a 34.4% reduction in visceral pain sensitivity in the Writhing's model in mice (Yimam et al., 2016). In vitro, it showed dose-dependent inhibition of the enzymatic activities of COX and LOX with $IC_{50}$ values of 20.9 µg/mL, 49.2 µg/mL, and 11.1 µg/mL in COX-1, COX-2, and 5-LOX, respectively (Yimam et al., 2016).

Previously we have also documented that, a bioflavonoid composition—UP446, which comprises baicalin from *Scutellaria baicalensis* and catechin from *Acacia catechu* to possess bioactivities including: (i) dual inhibition of COX and LOX (Burnett et al., 2007) (ii) normalization of COX-2, TNF-α, IL-1β, IL-6, and NF-κB gene expression in lipopolysaccharide (LPS)-induced human and animal cell lines (Tseng-Crank et al., 2010) (iii) inhibition of COX-2, 5-LOX, and inducible-nitric oxide synthase (iNOS) gene expression and moderation of NF-κB binding activity in endotoxin-stimulated rat peritoneal macrophages (Altavilla et al., 20090). Beneficial applications in OA related symptomatic pain relief has also been reported for UP446 from human clinical trials (Sampalis and Brownell, 2012; Arjmandi et al., 2014).

There is no report of using these compositions alone or in combination to reduce CTX-II biomarkers associated with joint health, bone health, or a combination thereof.

SUMMARY OF THE SUBJECT MATTER

In brief, the present disclosure is directed to compounds and compositions useful for management of bone disorders, cartilage disorders or both, and to methods of improving bone health, cartilage health or both.

In certain embodiments, this disclosure provides a composition comprising a mixture of a *Morus* extract, optionally enriched for one or more prenylated flavonoids (e.g., Diels-Alder adducts of a chalcone and a prenylphenyl moiety), or one or more stilbenes, or a combination thereof, and an *Acacia* extract, optionally enriched for flavans.

In other embodiments, compositions and methods for bone health, cartilage health or both, are disclosed that include preparing and utilizing a mixture of at least one *Morus* extract enriched for one or more prenylated flavonoids, at least one *Scutellaria* extract enriched for one or more free-B-ring flavonoids, and at least one *Acacia* extract enriched for one or more flavans.

In some embodiments, this disclosure provides a composition comprising a mixture of a *Morus* extract, optionally enriched for one or more prenylated flavonoids (e.g., Diels-Alder adducts of a chalcone and a prenylphenyl moiety), or one or more stilbenes, or a combination thereof, an *Acacia* extract, optionally enriched for flavans, and a *Scutellaria* extract, which may include *Scutellaria baicalensis*.

In further embodiments, this disclosure provides a composition comprising a mixture of a *Morus* extract, optionally enriched for prenylated flavonoids (e.g., Diels-Alder adducts of a chalcone and a prenylphenyl moiety), or one or more stilbenes, or a combination thereof, and an *Uncaria gambir* extract, optionally enriched for flavans.

In further embodiments, this disclosure provides a composition comprising a mixture of a*Morus* extract enriched for one or more prenylated flavonoids (e.g., Diels-Alder adducts of a chalcone and a prenylphenyl moiety), or one or more stilbenes, or a combination thereof, and a *Curcuma* extract, optionally enriched for curcuminoids. In other embodiments, this disclosure provides a composition comprising a mixture of a*Morus* extract enriched for one or more prenylated flavonoids (e.g., Diels-Alder adducts of a chalcone and a prenylphenyl moiety), or one or more stilbenes, and a *Peppermint* extract. In other embodiments, any of the compositions further, optionally, contain one or more of calcium, vitamin D, glucosamine compounds, such as N-acetyl glucosamine, and other bioactive compounds.

For example, a mixture of *Curcuma* and *Morus alba* root-bark extracts in a 1:1 ratio demonstrated beneficial synergistic effects with enhanced bone and cartilage health compared with either *Curcuma* or *Morus alba* root-bark extracts alone.

In another aspect, the present disclosure provides methods for managing bone disorders, cartilage disorders, or both. In certain embodiments, the compositions of this disclosure can be used in methods for treating, preventing, or managing bone disorders, cartilage disorders, or both, minimizing bone reabsorption, reducing cartilage degradation, promoting healthy bone density, protecting bone integrity, cartilage integrity or both, diminishing the action of enzymes that affect bone health, cartilage health or both, increase or maintain bone density, improving bone function, cartilage function or both, alleviating joint pain, alleviating joint stiffness, improving joint range of motion, flexibility or both, promoting mobility, or any combination thereof.

These and other aspects of contemplated embodiments will be apparent upon reference to the following detailed description.

BRIEF DESCRIPTION OF THE DRAWINGS

FIG. 1 shows bone histomorphometry evaluated on both femur and tibia per knee joint by Micro CT scan in rats having MIA-induced osteoarthritis, with or without treatment with a composition comprising an *Uncaria* extract and a *Morus* extract.

DETAILED DESCRIPTION

In certain aspects, the present disclosure provides prenylated flavonoids and resveratrol compounds mixed with flavans or curcuminoids for use in improving bone health, cartilage health or both. In certain embodiments, prenylated flavonoids and resveratrol compounds are extracted from *Morus alba* plant material, such as from the *Morus alba* root. In other embodiments, a *Morus* extract combined with flavans is optionally further combined with management agents for bone health, cartilage health or both, such as calcium (for example, found in the form of calcium citrate, calcium fructoborate, calcium carbonate, calcium lactate, calcium gluconate, or calcium phosphate), magnesium, boron, zinc, vitamin D, vitamin K, or other minerals and vitamins. Other dietary supplements that promote joint health, such as glucosamine compounds (like glucosamine sulfate, glucosamine hydrochloride, N acetylglucosamine), chondroitin sulfate and methylsulfonylmethane, hyaluronic acid, ω-3 fatty acids (such as eicosapentaenoic acid, EPA and docosahexaenoic acid, DHA), hydrolyzed collagen (e.g., from bovine type I collagen, chicken sternal type II collagen), collagen derived peptides or a mixture of collagen amino acids, xanthophyll carotenoids (e.g., astaxanthin, which is distributed in marine bacteria, algae, crustaceans, fish); non-steroidal anti-inflammatory agents/analgesics, COX/LOX inhibitory agents (such as acetaminophen, ibuprofen, celecoxib); neuropathic pain relief agents, herbal or plant extracts (such as a *Boswellia* extract).

In other embodiments, compositions and methods for bone health, cartilage health or both, are disclosed that include preparing and utilizing a mixture of at least one *Morus* extract enriched for one or more prenylated flavonoids, at least one *Scutellaria* extract enriched for one or more free-B-ring flavonoids, and at least one *Acacia* extract enriched for one or more flavans.

In some embodiments, this disclosure provides a composition comprising a mixture of a *Morus* extract, optionally enriched for one or more prenylated flavonoids (e.g., Diels-Alder adducts of a chalcone and a prenylphenyl moiety), or one or more stilbenes, or a combination thereof, an *Acacia* extract, optionally enriched for flavans, and a *Scutellaria* extract, which may include *Scutellaria baicalensis*.

In contemplated embodiments, the *Morus* extract, the *Scutellaria* extract, and the *Acacia* extract are blended in a 1.3:1:1 weight ratio. In some contemplated embodiments, the *Morus* extract, the *Scutellaria* extract, and the *Acacia* extract are blended in a 0.410:0.308:0.282 weight ratio. In contemplated embodiments, the *Morus* extract is from *Morus alba*, the *Scutellaria* extract is from *Scutellaria baicalensis*, and the *Acacia* extract is from *Acacia catechu*.

In some contemplated embodiments, the *Acacia* extract comprises 0.01% to 99.9% flavans; the *Morus* extract comprises 0.1% to 49.9% prenylated flavonoids; and the *Scutellaria* extract comprises 0.01% to 99.9% free-B-ring flavonoids.

Other aspects relate to methods of using compositions of this disclosure, such as for maintaining bone structure, cartilage structure or both, minimizing bone reabsorption, preventing cartilage degradation, increasing bone density, promoting healthy joints by protecting cartilage integrity, diminishing the action of enzymes that affect bone health, cartilage health, or both, improving joint movement or function, alleviating joint pain, alleviating joint discomfort, alleviating joint pain and discomfort, alleviating joint stiffness, improving joint range of motion or flexibility, promote mobility, or the like.

In the following description, certain specific details are set forth in order to provide a thorough understanding of various embodiments of this disclosure. However, one skilled in the art will understand that the subject matter and embodiments disclosed herein may be practiced without these details.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. Unless the context requires otherwise, throughout the present specification and claims, the word "comprise" and variations thereof, such as, "comprises" and "comprising," as well as synonymous terms like "include" and "have" and variants thereof, are to be construed in an open, inclusive sense; that is, as "including, but not limited to."

Reference throughout this specification to "one embodiment", a "contemplated embodiment", or "an embodiment" means that a feature, structure or characteristic described regarding the embodiment is included in at least one embodiment of the subject matter disclosed herein. Thus, the appearances of the phrases to "one embodiment", a "contemplated embodiment", or "an embodiment" in various places throughout this specification are not necessarily all referring to the same embodiment. Furthermore, the features, structures, or characteristics may be combined in any suitable manner in one or more embodiments.

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double or triple bonds), having from one to twelve carbon atoms ($C_1$-$C_{12}$ alkyl), or one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double or triple bonds), and having from one to twelve carbon atoms, e.g., methylene, ethylene, propylene, n-butylene, ethenylene, propenylene, n-butenylene, propynylene, n-butynylene, and the like.

The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms.

Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may include fused or bridged ring systems. Aryl radicals include aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted. "Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, or having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of this disclosure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_b R_f$— where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl), wherein at least one hydrogen atom is replaced by a bond to a non-hydrogen atoms such as a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom, such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_g R_h$, —$NR_g C(\!\!=\!\!O)R_h$, —$NR_g C(\!\!=\!\!O)NR_g R_h$, —$NR_g C(\!\!=\!\!O)OR_h$, —$NR_g SO_2 R_h$, —$OC(\!\!=\!\!O)NR_g R_h$, —$OR_g$, —$SR_g$, —$SOR_g$, —$SO_2 R_g$, —$OSO_2 R_g$, —$SO_2 OR_g$, $=\!\!NSO_2 R_g$, and —$SO_2 NR_g R_h$. "Substituted" also means any of the above groups in which one or more hydrogen atoms are replaced with —$C(\!\!=\!\!O)R_g$, —$C(\!\!=\!\!O)OR_g$, —$C(\!\!=\!\!O)NR_g R_h$, —$CH_2 SO_2 R_g$, —$CH_2 SO_2 NR_g R_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl group. In addition, each of the foregoing substituents may also be optionally substituted with one or more of the above substituents.

"Glycoside" refers to a molecule in which a sugar group is bonded through its anomeric carbon to another group via a glycosidic bond. Exemplary sugars include glucose, rhamnose, manose, galactose, arabinose, glucuronide and others. Glycosides can be linked by an O— (an O-glycoside), N— (a glycosylamine), S— (a thioglycoside), or C— (a C-glycoside) glycosidic bond. Compounds of this disclosure can form glycosides at any suitable attachment point.

A "prenyl group" is a moiety comprising a five-carbon backbone of the following structure:

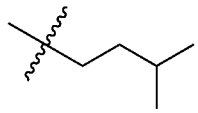

In some embodiments, prenyl groups comprise one or more carbon-carbon double bonds and/or are substituted with one or more substituents. "Prenyl" refers to the

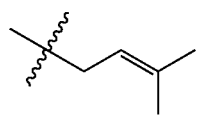 [SMILES: *CC=C(C)C]

radical. Isoprenyl refers to

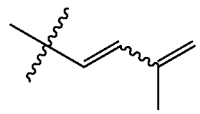 [SMILES: *C=CC(=C)C]

the radical (cis or trans). Prenyl groups are substituted or unsubstituted, such as

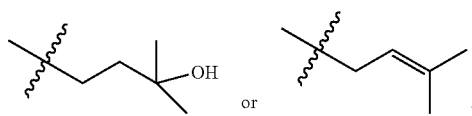

"Prenylphenyl" refers to a phenyl moiety connected to a prenyl moiety as defined above. Prenylphenyls include substituted phenyls such as flavonoids and other substituted phenyls and heteroaryls, provided there is at least one prenyl group in the molecule. In the case of substituted phenyls and heteroaryl, the prenyl moiety need not be directly attached to the phenyl ring, but can be attached at any point in the molecule.

"Chalcone" refers to a compound comprising the following core structure:

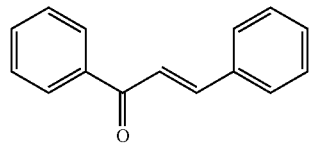

Chalcones can be variously substituted at any of the above carbon atoms.

"Prodrug" is meant to indicate a compound that may be converted under physiological conditions or by solvolysis to a biologically active compound of this disclosure. Thus, the term "prodrug" refers to a metabolic precursor of a compound of this disclosure that is pharmaceuticallyand nutraceutically acceptable. A prodrug may be inactive when administered to a subject in need thereof, but is converted in vivo to an active compound of this disclosure. Prodrugs are typically rapidly transformed in vivo to yield the parent compound of this disclosure, for example, by hydrolysis in blood or intestine or metabolized in the liver. The prodrug compound often offers advantages of solubility, tissue compatibility or delayed release in a mammalian organism (see Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical and Nutraceutical Association and Pergamon Press, 1987.

The term "prodrug" is also meant to include any covalently bonded carriers, which release the active compound of this disclosure in vivo when such prodrug is administered to a mammalian subject. Prodrugs of a compound of this disclosure may be prepared by modifying functional groups present in the compound of this disclosure in such a way that the modifications are cleaved, either in routine manipulation or in vivo, to the parent compound of this disclosure. Prodrugs include compounds of this disclosure wherein a hydroxy, amino or mercapto group is bonded to any group that, when the prodrug of the compound of this disclosure is administered to a mammalian subject, cleaves to form a free hydroxy, free amino or free mercapto group, respectively. Examples of prodrugs include acetate, formate and benzoate derivatives of alcohol or amide derivatives of amine functional groups in the compounds of this disclosure and the like.

The instant disclosure is also meant to encompass all pharmaceutically or nutraceutically acceptable compounds of any one of structures (I)-(VI) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, 18F, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of any one of structures (I)-(VI), for example, those incorporating a radioactive isotope, are useful in drug or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of any one of structures (I)-(VI) can generally be prepared by conventional techniques known to those skilled in the art or by processes analogous to those described in the preparations and examples as set out herein using an appropriate isotopically-labeled reagent in place of the non-labeled reagent previously employed.

The instant disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, this disclosure includes compounds produced by a process comprising administering a compound of this disclosure to a mammal for a period of time sufficient to yield a metabolic product thereof. Such products are typically identified by administering a radiolabelled compound of this disclosure in a detectable dose to an animal, such as rat, mouse, guinea pig, dog, cat, pig, sheep, horse, monkey, or human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans, domestic animals (such as laboratory animals or household pets like rat, mouse, guinea pig, cats, dogs, swine, cattle, sheep, goats, horses, rabbits, primates), and non-domestic animals (such as wildlife) or the like.

"Optional" or "optionally" means that the subsequently described element, component, event or circumstances may or may not occur, and includes instances where the element, component, event or circumstance occur and instances in which they do not. For example, "optionally substituted aryl" means that the aryl radical may or may not be substituted—in other words, the description includes both substituted aryl radicals and aryl radicals having no substitution.

"Pharmaceutically or nutraceutically acceptable carrier, diluent or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically or nutraceutically acceptable salt" includes both acid and base addition salts.

"Pharmaceutically or nutraceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, or the like.

"Pharmaceutically or nutraceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include the sodium, potassium, lithium, ammonium, calcium, magnesium, iron, zinc, copper, manganese, aluminum salts and the like. In certain embodiments, the inorganic salts are ammonium, sodium, potassium, calcium, or magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases include isopropylamine, diethylamine, ethanolamine, trimethylamine, dicyclohexylamine, choline, or caffeine.

Often crystallizations produce a solvate of the compound of this disclosure. As used herein, the term "solvate" refers to an aggregate that comprises one or more molecules of a compound of this disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of this disclosure may be true solvates, while in other cases, a compound of this disclosure may merely retain adventitious water or be a mixture of water plus some adventitious solvent.

A "pharmaceutical composition" or "nutraceutical composition" refers to a formulation of a compound of this disclosure and a medium generally accepted in the art for the delivery of the biologically active compound to mammals, e.g., humans. For example, a pharmaceutical composition of the present disclosure may be formulated or used as a stand alone composition, or as a component in a prescription drug, an over-the-counter (OTC) medicine, a botanical drug, an herbal medicine, a homeopathic agent, functional foods, or any other form of health care product reviewed and approved by a government agency. Exemplary nutraceutical compositions of the present disclosure may be formulated or used as a stand alone composition, or as a nutritional or bioactive component in food, a novel food, a functional food, a beverage, a bar, a food flavor, a food additive, a medical food, a dietary supplement, or an herbal product. A medium generally accepted in the art includes all pharmaceutically or nutraceutically acceptable carriers, diluents or excipients therefor.

As used herein, "enriched for" refers to a plant extract or other preparation having at least a two-fold up to about a 1000-fold increase in the amount or activity of one or more active compounds as compared to the amount or activity of the one or more active compounds found in the weight of the plant material or other source before extraction or other preparation. In certain embodiments, the weight of the plant material or other source before extraction or other preparation may be dry weight, wet weight, or a combination thereof.

As used herein, "major active ingredient" or "major active component" refers to one or more active compounds found in a plant extract or other preparation, or enriched for in a plant extract or other preparation, which is capable of at least one biological activity. In certain embodiments, a major active ingredient of an enriched extract will be the one or more active compounds that were enriched in that extract. Generally, one or more major active components will impart, directly or indirectly, most (i.e., greater than 50%) of one or more measurable biological activities or effects as compared to other extract components. In certain embodiments, a major active ingredient may be a minor component by weight percentage of an extract (e.g., less than 50%, 25%, 20%, 15%, 10%, 5%, or 1% of the components contained in an extract) but still provide most of the desired biological activity.

Any composition of this disclosure containing a major active ingredient may also contain minor active ingredients that may or may not contribute to the pharmaceutical or nutraceutical activity of the enriched composition, but not to the level of major active components, and minor active components alone may not be effective in the absence of a major active ingredient.

"Effective amount" or "therapeutically effective amount" refers to that amount of a compound or composition of this disclosure that, when administered to a mammal, such as a human, is sufficient to effect treatment, including any one or more of: (1) treating or preventing loss of bone and cartilage in a mammal; (2) promoting bone and cartilage health; (3) suppressing loss of bone and cartilage in a mammal; (4) increasing bone density in a mammal; (5) treating or preventing eosteoporosis in a mammal; (6) modifying inflammation of bone and cartilage in a mammal; and (7) protecting bone and cartilage integrity. The amount of a compound or composition of this disclosure that constitutes a "therapeutically effective amount" will vary depending on the compound, the condition being treated and its severity, the manner of administration, the duration of treatment, or the body weight and age of a subject to be treated, but can be determined by one of ordinary skill in the art having regard to his own knowledge and to this disclosure.

"Supplements" as used herein refers to a product that improves, promotes, supports, increases, regulates, manages, controls, maintains, optimizes, modifies, reduces, inhibits, or prevents a particular condition, structure or function associated with a natural state or biological process (i.e., are not used to diagnose, treat, mitigate, cure, or prevent disease). In certain embodiments, a supplement is a dietary supplement. For example, with regard to bone and cartilage health-related conditions, dietary supplements may be used to maintain bone and cartilage integrity, minimize bone reabsorption, minimize cartilage degradation, promote healthy bone and cartilage by protecting bone and cartilage integrity, diminish the action of enzymes that affect bone and cartilage health, improve oesteoprosis condition, support bone rebuild, alleviate pain, alleviate discomfort, alleviate stiffness, improve range of motion, improve flexibility, promote mobility, or the like. In certain embodiments, dietary supplements are a special category of diet, food or both, and are not a drug.

"Treating" or "treatment" or "ameliorating" refers to either a therapeutic treatment or prophylactic/preventative treatment of a disease or condition of interest in a mammal, such as a human, having or suspected of having a disease or condition of interest, and includes: (i) preventing the disease or condition from occurring in a mammal, in particular, when such mammal is predisposed to the condition but has not yet been diagnosed as having it;

(ii) inhibiting the disease or condition, i.e., arresting its development; (iii) relieving the disease or condition, i.e., causing regression of the disease or condition; or (iv) relieving the symptoms resulting from the disease or condition, (e.g., relieving pain, reducing inflammation, reducing loss of cartilege, increasing bone density) without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. In certain embodiments, compositions and methods of the instant disclosure are useful for treating, managing or ameliorating, for example, osteoarthritis, rheumatoid arthritis, or both.

As used herein, "statistical significance" refers to a p value of 0.050 or less as calculated using the Students t-test and indicates that it is unlikely that a particular event or result being measured has arisen by chance.

The chemical naming protocol and structure diagrams used herein are a modified form of the I.U.P.A.C. nomenclature system, using the ACD/Name Version 9.07 software program or ChemDraw Ultra Version 11.0 software naming program (CambridgeSoft), wherein the compounds of this disclosure are named herein as derivatives of the central core structure, e.g., the imidazopyridine structure. For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

As noted herein, in certain embodiments, the present disclosure provides a composition comprising prenylated flavonoids. Flavonoids include flavans, flavones, flavonols, flavanones, flavanonols, isoflavonoids, neoflavonoids, chalcones, arylbenzofuran, or the like.

In certain embodiments, a flavonoid compound of the present disclosure has structure (III), as follows:

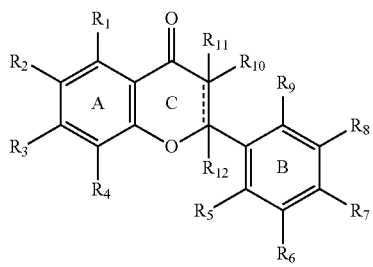

III wherein $R_1$—$R_{12}$ are each independently H, hydroxyl, a prenyl group, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl, or a bond to a compound of structure (III) or (IV); or one of $R_1$—$R_{12}$ joins with another one of $R_1$—$R_{12}$ to form a ring, and the remaining $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied (e.g., when the optional double bond is present in ring C, then $R_{12}$ is absent and at least one of $R_{10}$ or $R_{11}$ is absent). In certain embodiments, at least one of $R_1$—$R_{12}$ is a prenyl group, such as

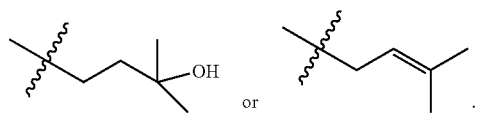

In further embodiments, the optional double bond is present in ring C, $R_{11}$ and $R_{12}$ are absent, and $R_{10}$ is a prenyl group. In still further embodiments, at least one of $R_1$—$R_9$ is a prenyl group and $R_{10}$—$R_{12}$ are independently H or hydroxyl. In certain specific embodiments, the prenylated flavonoids include Albanin G, Kuwanon G, Morusin, or any combination thereof.

In certain embodiments, a flavonoid compound of the present disclosure has structure (IV) as follows:

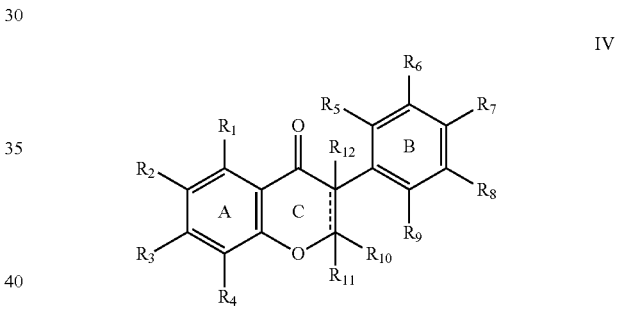

IV wherein $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl, or a bond to a compound of structure (III) or (IV); or one of $R_1$—$R_{12}$ joins with another one of $R_1$—$R_{12}$ to form a ring, and the remaining $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied (e.g., when the optional double bond is present in ring C, then $R_{12}$ is absent and at least one of $R_{10}$ or $R_{11}$ is absent). In certain embodiments, at least one of $R_1$—$R_{12}$ is a prenyl group, such as

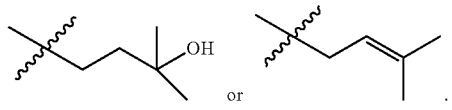

In further embodiments, the optional double bond is present in ring C, $R_{11}$ and $R_{12}$ are absent, and $R_{10}$ is a prenyl group. In still further embodiments, at least one of $R_1$—$R_9$ is a prenyl group and $R_{10}$—$R_{12}$ are independently H or hydroxyl. In certain specific embodiments, the prenylated flavonoids include Albanin G, Kuwanon G, Morusin, morusinol, Sanggenon, isoxanthoumol, glabridin, cathayanon A, or any combination thereof.

In some embodiments, a chalconoid compound of the present disclosure has structure (V) as follows:

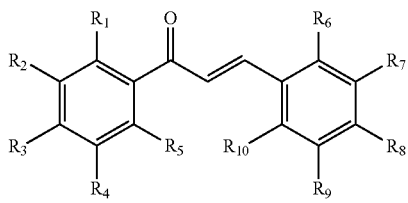

V wherein $R_1$—$R_{10}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, or aralkylcarbonyl. In certain embodiments, at least one of $R_1$—$R_{10}$ is a prenyl group, such as

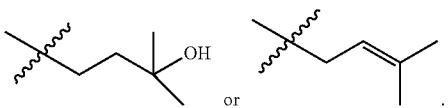

In further embodiments, the optional double bond is present in ring C, $R_{11}$ and $R_{12}$ are absent, and $R_{10}$ is a prenyl group. In still further embodiments, at least one of $R_1$—$R_9$ is a prenyl group and $R_{10}$—$R_{12}$ are independently H or hydroxyl. In certain specific embodiments, a chalconoid compound includes xanthohumol.

In certain embodiments, a stilbene compound of the present disclosure is an (E)-stilbene (trans isomer) structure of formula I or (Z)-stilbene (cis isomer) structure of formula II, as follows:

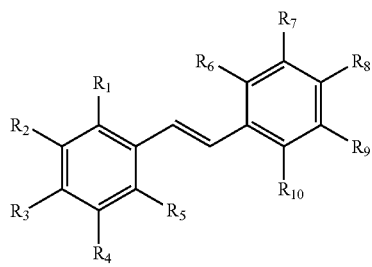

I

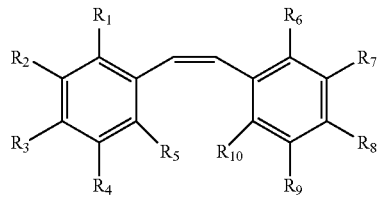

II wherein $R_1$—$R_{10}$ are each independently H, hydroxyl, glycoside, a prenyl group, flavonoid, chalcone, halogen, sulfhydryl, amino, aldehyde, $C_{1-12}$ alkyl, $C_{1-12}$ alkenyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, or aralkylcarbonyl. In certain embodiments, at least one of $R_1$—$R_{12}$ is a prenyl group, such as

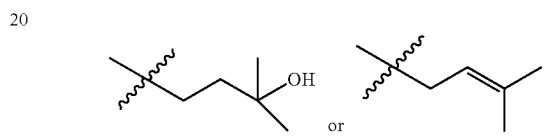

In further embodiments, $R_1$, $R_5$, $R_6$ and $R_{10}$ are H. In still further embodiments, $R_2$ is a glucoside, or $R_2$ and $R_8$ are glycosides, and one or more of $R_4$, $R_9$, and $R_{10}$ are hydroxyl. In yet further embodiments, $R_1$, $R_5$, $R_6$ are H, and one or more of $R_2$—$R_4$ and $R_7$—$R_{10}$ are independently hydroxyl, $C_{1-3}$ alkoxy, or any combination thereof. In certain specific embodiments, a stilbene includes oxyresveratrol, resveratrol, piceatannol, pinosylvin, 3,4'-dihydroxystilbene, combretastatin A-1, pterostilbene, rhapontigenin, and a stilbene glycoside includes mulberroside A, rhaponticin, piceid, astringin, or any combination of these stilbenes or stilbene glycosides.

It is understood that any embodiment of the compounds of structure (I) to (VI), as set forth above, and any specific substituent set forth herein for the compounds of structure (I) to (VI), may be independently combined with other embodiments or sub stituents of any one of the compounds of structure (I) to (VI) to form embodiments of this disclosure not specifically set forth above. In addition, in the event that a list of substituents is listed for any particular R group in a particular embodiment or claim, it is understood that each individual substituent may be deleted from the particular embodiment or claim and that the remaining list of substituents will be considered to be within the scope of this disclosure.

For the purposes of administration, compounds and compositions of the present disclosure may be administered as a raw chemical or may be formulated as pharmaceutical or nutraceutical compositions. In certain embodiments, pharmaceutical or nutraceutical compositions of the present disclosure comprise any one or more of the compounds having structure (I) to (VI) and a pharmaceutically or nutraceutically acceptable carrier, diluent or excipient. The compounds of structures (I) to (VI) are individually or in combination present in the composition in an amount that is effective to treat a particular disease or condition of interest. Promoting, managing, or improving joint health or treating disease with compounds as set forth in any one of structures (I) to (VI) can be determined by one skilled in the art, for example, as described in the Examples herein.

In certain embodiments, compounds and compositions (e.g., pharmaceutical, nutraceutical) of the present disclosure may be administered in an amount sufficient to promote bone health; improve bone health; maintain bone health; treat or manage bone disorders; support bone health; support a normal and comfortable range of motion and/or flexibility; improve range of motion and/or flexibility; reduce the action of harmful enzymes that break down bones; alter the action of enzymes that affect bone absorption; improve movement with normal bone function; improve physical mobility; manage and/or maintain physical mobility; alleviate pain and/or stiffness due to bone loss; improve physical function; promote or enhance flexibility and comfortable movement; promote healthy bone function and comfort; relieve bone discomfort; relieve bone discomfort caused by exercise, work, overexertion or any combination thereof; promote healthy bones by protecting cartilage integrity; maintain joint cartilage; support joint cartilage; treat, prevent, or manage cartilage degradation; minimize cartilage degradation; promote joint health or comfort by maintaining synovial fluid for joint lubrication; support joint stability and joint flexibility; revitalize joints and promote mobility; promote flexible joints and strong cartilage; maintain steady blood flow to joints to support enhanced flexibility and/or strength; promote joint comfort and a wide range of motion after exercise, work, overexertion, or any combination thereof; or any other associated indication described herein, and generally with acceptable toxicity to a patient.

In certain other embodiments, compounds and compositions (e.g., pharmaceutical, nutraceutical) of the present disclosure may be administered in an amount sufficient to prevent or treat bone disorders, cartilage disorders, or both. Those osteochondrodyspiasia includes osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia, or any other bone and cartilage associated indication, and generally with acceptable toxicity to a patient.

Administration of the compounds of this disclosure, or their pharmaceutically or nutraceutically acceptable salts, in pure form or in an appropriate pharmaceutical or nutraceutical composition, can be carried out via any of the accepted modes of administration of agents for serving similar utilities. The pharmaceutical or nutraceutical compositions of this disclosure can be prepared by combining a compound of this disclosure with an appropriate pharmaceutically or nutraceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical or nutraceutical compositions include oral, topical, transdermal, inhalation, parenteral, sublingual, buccal, rectal, vaginal, or intranasal. The term parenteral as used herein includes subcutaneous injections, intravenous, intramuscular, intrasternal injection or infusion techniques. Pharmaceutical or nutraceutical compositions of this disclosure are formulated so as to allow the active ingredients contained therein to be bioavailable upon administration of the composition to a patient. In certain embodiments, compositions of the present disclosure are administered to a subject or patient in the form of one or more dosage units, where, for example, a tablet may be a single dosage unit, and a container of a compound of this disclosure in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of this disclosure, or a pharmaceutically or nutraceutically acceptable salt thereof, for treatment of a disease or condition of interest in accordance with the teachings of this disclosure.

A pharmaceutical or nutraceutical composition of this disclosure may be in the form of a solid or liquid. In one aspect, the carrier(s) are particulate, so that the compositions are, for example, in tablet or powder form. The carrier(s) may be liquid, with the compositions being, for example, oral syrup, injectable liquid or an aerosol, which is useful in, for example, inhalatory administration.

When intended for oral administration, the pharmaceutical or nutraceutical composition is in either solid or liquid form, where semi-solid, semi-liquid, suspension and gel forms are included within the forms considered herein as either solid or liquid.

As a solid composition for oral administration, the pharmaceutical or nutraceutical composition may be formulated into a powder, granule, compressed tablet, pill, capsule, chewing gum, wafer, bar, or like form. Such a solid composition will typically contain one or more inert diluents or edible carriers. In addition, one or more of the following may be present: binders such as carboxymethylcellulose, ethyl cellulose, cyclodextrin, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex®; glidants such as colloidal silicon dioxide; sweetening agents such as sucrose or saccharin; a flavoring agent such as peppermint, methyl salicylate or orange flavoring; and a coloring agent.

When the pharmaceutical or nutraceutical composition is in the form of a capsule, for example, a gelatin capsule, it may contain, in addition to materials of the above type, a liquid carrier such as polyethylene glycol or oil.

The pharmaceutical or nutraceutical composition may be in the form of a liquid, for example, an elixir, syrup, gel, solution, emulsion or suspension. The liquid may be for oral administration or for delivery by injection, as two examples. When intended for oral administration, a useful composition contains, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical or nutraceutical compositions of this disclosure, whether they be solutions, suspensions or other like form, may include one or more of the following adjuvants: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as carbonate, citrates, acetate, lactate, gluconate, or phosphates and agents for the adjustment of tonicity such as sodium chloride or dextrose. The parenteral preparation can be enclosed in ampoules, disposable syringes or multiple dose vials made of glass or plastic. Physiological saline is a generally useful adjuvant. An injectable pharmaceutical or nutraceutical composition is sterile.

A liquid pharmaceutical or nutraceutical composition of this disclosure intended for either parenteral or oral administration should contain an amount of a compound of this disclosure such that a suitable dosage will be obtained.

The pharmaceutical or nutraceutical composition of this disclosure may be intended for topical administration, in which case the carrier may suitably comprise a solution, emulsion, cream, lotion, ointment, or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical or nutraceutical composition for topical administration. If intended for transdermal administration, the composition may include a transdermal patch or iontophoresis device.

The pharmaceutical or nutraceutical composition of this disclosure may be intended for rectal administration, in the form, for example, of a suppository, which will melt in the rectum and release the drug. The composition for rectal administration may contain an oleaginous base as a suitable nonirritating excipient. Such bases include lanolin, cocoa butter and polyethylene glycol.

The pharmaceutical or nutraceutical composition of this disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical or nutraceutical composition of this disclosure in solid or liquid form may include an agent that binds to the compound of this disclosure and thereby assists in the delivery of the compound. Suitable agents that may act in this capacity include a monoclonal or polyclonal antibody, a protein or a liposome.

The pharmaceutical or nutraceutical composition of this disclosure in solid or liquid form may include reducing the size of a particle to, for example, improve bioavailability. The size of a powder, granule, particle, microsphere, or the like in a composition, with or without an excipient, can be macro (e.g., visible to the eye or at least 100 µm in size), micro (e.g., may range from about 100 µm to about 100 nm in size), nano (e.g., may no more than 100 nm in size), and any size in between or any combination thereof to improve size and bulk density.

The pharmaceutical or nutraceutical composition of this disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation, may determine the most appropriate aerosol(s).

The pharmaceutical or nutraceutical compositions of this disclosure may be prepared by methodology well known in the pharmaceutical or nutraceutical art. For example, a pharmaceutical or nutraceutical composition intended to be administered by injection can be prepared by combining a compound of this disclosure with sterile, distilled water so as to form a solution. A surfactant may be added to facilitate the formation of a homogeneous solution or suspension. Surfactants are compounds that non-covalently interact with the compound of this disclosure so as to facilitate dissolution or homogeneous suspension of the compound in the aqueous delivery system.

The compounds of this disclosure, or their pharmaceutically or nutraceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of this disclosure, or pharmaceutically or nutraceutically acceptable derivatives thereof, may also be administered simultaneously with, prior to, or after administration of one or more other therapeutic agents. Such combination therapy includes administration of a single pharmaceutical or nutraceutical dosage formulation which contains a compound of this disclosure and one or more additional active agents, as well as administration of the compound of this disclosure and each active agent in its own separate pharmaceutical or nutraceutical dosage formulation. For example, a compound of this disclosure and another active agent can be administered to the patient together in a single oral dosage composition, such as a tablet or capsule, or each agent can be administered in separate oral dosage formulations. Where separate dosage formulations are used, the compounds of this disclosure and one or more additional active agents can be administered at essentially the same time, i.e., concurrently, or at separate staggered times, i.e., sequentially; combination therapy is understood to include all these regimens.

It is understood that in the present description, combinations of substituents or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, a protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of this disclosure which are pharmacologically active. Such derivatives may therefore be described as "prodrugs". All prodrugs of compounds of this disclosure are included within the scope of this disclosure.

Furthermore, all compounds of this disclosure which exist in free base or acid form can be converted to their pharmaceutically or nutraceutically acceptable salts by treatment with the appropriate inorganic or organic base or acid by methods known to one skilled in the art. Salts of the compounds of this disclosure can be converted to their free base or acid form by standard techniques.

In some embodiments, compounds of the present disclosure can be isolated from plant sources, for example, from those plants included in the Examples and elsewhere throughout the present application. Suitable plant parts for isolation of the compounds include leaves, bark, trunk, trunk bark, stems, stem bark, twigs, tubers, root, root bark, bark surface (such as periderm or polyderm, which may include phellem, phellogen, phelloderm, or any combination thereof), young shoots, rhizomes, seed, fruit, androecium, gynoecium, calyx, stamen, petal, sepal, carpel (pistil), flower, or any combination thereof. In some related embodiments, the compounds are isolated from plant sources and synthetically modified to contain any of the recited substituents. In this regard, synthetic modification of the compound isolated from plants can be accomplished using any number of techniques that are known in the art and are well within the knowledge of one of ordinary skill in the art.

*Morus alba* L (Moraceae), the mulberry or white berry plant, is native to northern China, and has been cultivated and naturalized elsewhere, from India to the Middle East to Southern Europe, and recently to the North American area. *Morus* root-bark is used in traditional medicine known as Sang bai pi or Cortex Mori (Pharmacopoeia of the People's Republic of China, 2005). *Morus* herb is also known as Pong-na-moo in Korean and Sohakuhi in Japan. In contemporary pharmacological research, *Morus alba* root-bark has been reported to have antibacterial, anti-viral, antioxidant, hypoglycemic, hypolipidemic, neuroprotective, antiulcer, analgesic and anti-inflammatory activities. A variety of bioactive compounds from *Morus alba* root-bark have in vivo and in vitro anti-inflammatory activity.

As noted herein, compounds of a Diels-Alder adduct of a chalcone and a prenylphenyl moiety, prenylated flavonoids, stilbenes, or any combination thereof may be obtained by chemical synthesis or from a plant extract, such as a *Morus* or *Milicia* extract. For example, *Morus* is a genus of flowering trees in the family Moraceae, which comprises more than 30 species (known as mulberries) that grow wild or under cultivation in many countries. Exemplary *Morus* species include *Morus alba* L., *Morus australis* Poir, *Morus celtidifolia* Kunth, *Morus insignis*, *Morus mesozygia* Stapf, *Morus microphylla*, *Morus nigra* L., *Morus rubra* L., *Morus atropurpurea*, *Morus bombycis*, *Morus cathayana*, *Morus indica*, *Morus lhou*, *Morus japonica*, *Morus kagayamae*, *Morus laevigata*, *Morus latifolia*, *Morus liboensis*, *Morus macroura*, *Morus mongolica*, *Morus multicaulis*, *Morus notabilis*, *Morus rotundiloba*, *Morus serrate*, *Morus heterophyllus*, *Morus tillaefolia*, *Morus trilobata*, *Morus yunnanensis*, and *Morus wittiorum*.

In certain embodiments, a *Morus* extract is from *Morus alba*, or a *Morus* extract is a mixture of extracts from one, two, three, four, or five different *Morus* species. A mixture of extracts may include extracts from two or more *Morus* species or other sources listed in Table A. For example, a composition comprising a Diels-Alder adduct of a chalcone and a prenylphenyl moiety, a prenylated flavonoid, a stilbene, or any combination thereof may be made up of a *Morus* extract (e.g., *Morus alba*) and a *Milicia* extract (e.g., *Milicia excelsa*). In certain embodiments, a *Morus* extract enriched for prenylated flavonoids and stilbenes is from *Morus alba* (a) root bark, (b) root bark and leaves, (c) rootbark and twigs, (d) root bark, leaves and twigs, or (e) root bark, root wood, fine roots, stem bark, branch, branch bark, branch wood, and twigs.

In some specific embodiments, compounds of a Diels-Alder adduct of a chalcone and a prenylphenyl moiety may be any one or more of the compounds provided in Table A.

TABLE A

List of Exemplary Diels-Alder Adduct Compounds

| Structure | Name | Species | Molecular Formula | M.W. |
|---|---|---|---|---|
| 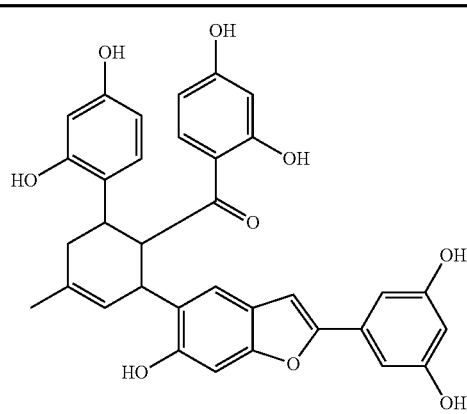 | Albafuran C | *Morus alba* | $C_{34}H_{28}O_9$ | 580.590 |

TABLE A-continued

List of Exemplary Diels-Alder Adduct Compounds

| Structure | Name | Species | Molecular Formula | M.W. |
|---|---|---|---|---|
| 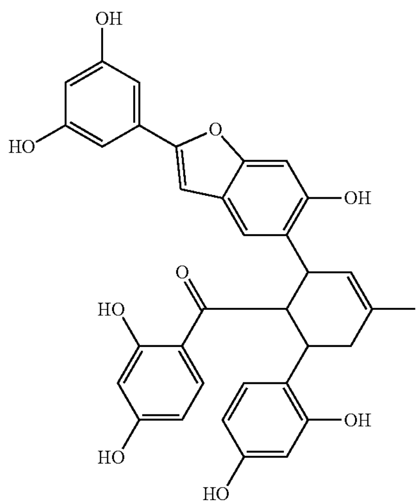 [SMILES: CC1=CC(c2cc3cc(-c4cc(O)cc(O)c4)oc3cc2O)C(C(=O)c2ccc(O)cc2O)C(c2ccc(O)cc2O)C1] | Albafuran C; 2-Epimer | *Morus australis* | $C_{34}H_{28}O_9$ | 580.590 |
| 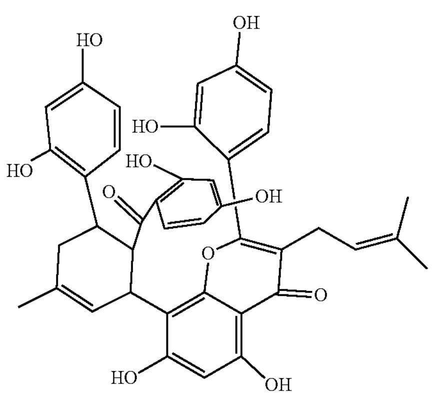 [SMILES: CC(C)=CCc1c(-c2ccc(O)cc2O)oc2c(C3C=C(C)CC(c4ccc(O)cc4O)C3C(=O)c3ccc(O)cc3O)c(O)cc(O)c2c1=O] | Albanin F | *Morus alba*, also from *Morus australis*, *Morus bombycis*, and *Morus lhou* | $C_{40}H_{36}O_{11}$ | 692.718 |
| 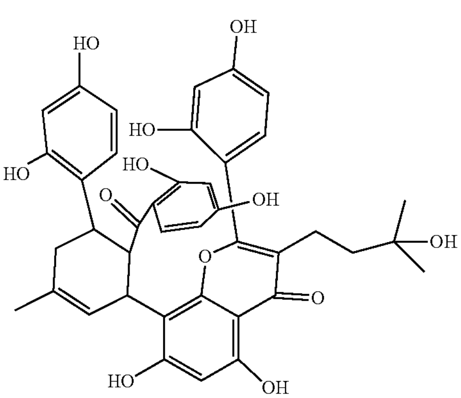 [SMILES: CC1=CC(c2c(O)cc(O)c3c(=O)c(CCC(C)(C)O)c(-c4ccc(O)cc4O)oc23)C(C(=O)c2ccc(O)cc2O)C(c2ccc(O)cc2O)C1] | Albanin F (Moracenin D); 12,13-Dihydro, 13-hydroxy | *Morus* sp. | $C_{40}H_{38}O_{12}$ | 710.733 |

TABLE A-continued

List of Exemplary Diels-Alder Adduct Compounds

| Structure | Name | Species | Molecular Formula | M.W. |
|---|---|---|---|---|
| 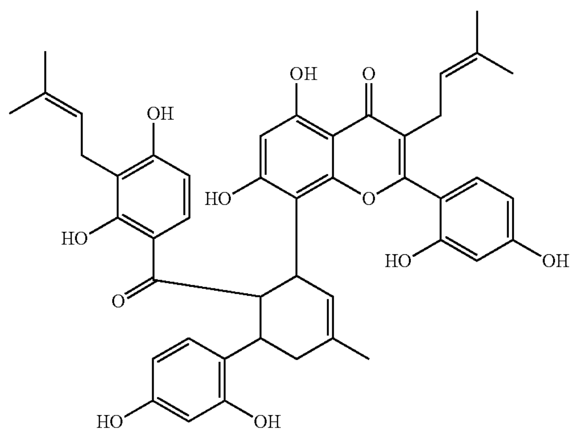 [SMILES: CC(C)=CCc1c(O)ccc(C(=O)C2C(c3c(O)cc(O)c4c(=O)c(CC=C(C)C)c(-c5ccc(O)cc5O)oc34)C=C(C)CC2c2ccc(O)cc2O)c1O] | Albanin G (Kuwanon H. Moracenin A.) | Morus alba; also isol. from Morus australis, Morus bombycis, and Morus lhou | $C_{45}H_{44}O_{11}$ | 760.836 |
| 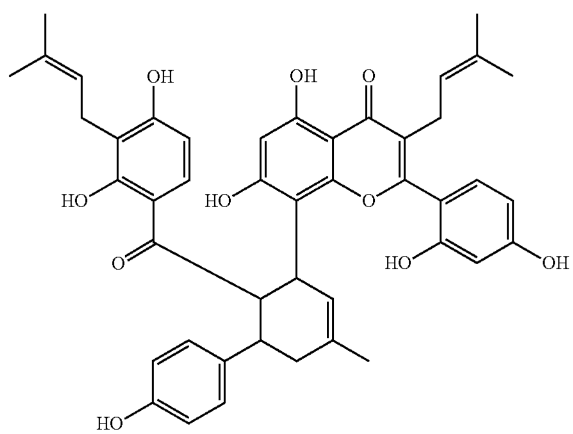 [SMILES: CC(C)=CCc1c(O)ccc(C(=O)C2C(c3c(O)cc(O)c4c(=O)c(CC=C(C)C)c(-c5ccc(O)cc5O)oc34)C=C(C)CC2c2ccc(O)cc2)c1O] | Albanin G; 2'''-Deoxy (Mongolicin D) | Morus mongolica | $C_{45}H_{44}O_{10}$ | 744.837 |
| 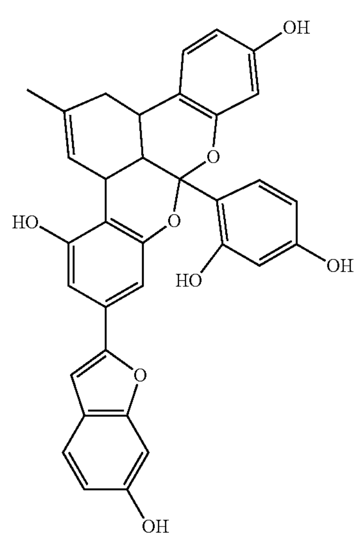 [SMILES: CC1=CC2c3c(O)cc(-c4cc5ccc(O)cc5o4)cc3OC3(c4ccc(O)cc4O)Oc4cc(O)ccc4C(C1)C23] | Albanol A (Mulberrofuran G.) | Morus lhou | $C_{34}H_{26}O_{8}$ | 562.575 |

TABLE A-continued

List of Exemplary Diels-Alder Adduct Compounds

| Structure | Name | Species | Molecular Formula | M.W. |
|---|---|---|---|---|
| 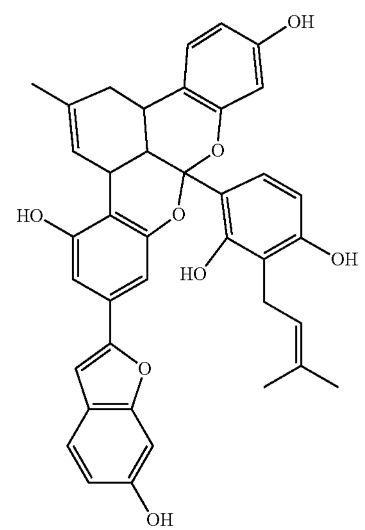 [SMILES: CC(C)=CCc1c(O)ccc(C23Oc4cc(O)ccc4C4CC(C)=CC(c5c(O)cc(-c6cc7ccc(O)cc7o6)cc5O2)C43)c1O] | Albanol A; 3"-(3-Methyl-2-butenyl), Mulberrofuran F | *Morus lhou* | $C_{39}H_{34}O_8$ | 630.693 |
| 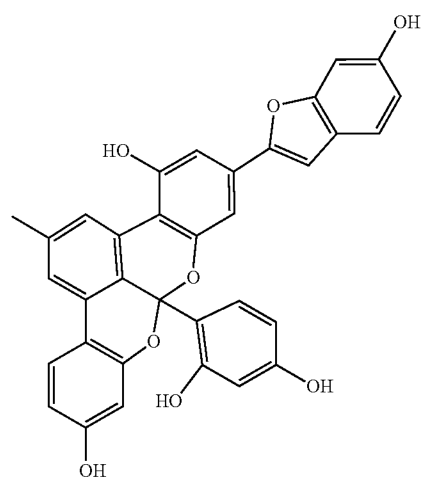 [SMILES: Cc1cc2c3c(c1)-c1c(O)cc(-c4cc5ccc(O)cc5o4)cc1OC3(c1ccc(O)cc1O)Oc1cc(O)ccc1-2] | Albanol B | *Morus alba* | $C_{34}H_{22}O_8$ | 558.543 |
| 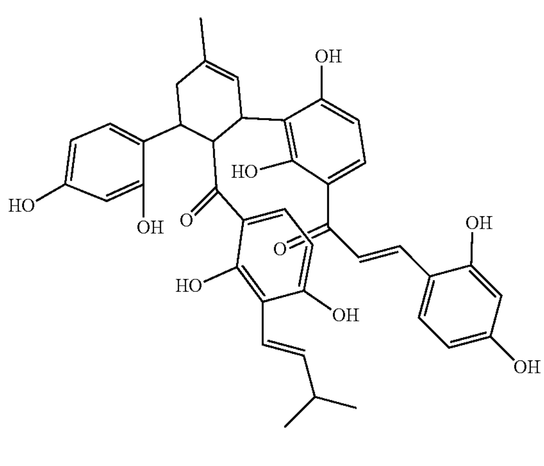 | Artonin C | *Artocarpus heterophyllus* (jackfruit) | $C_{40}H_{38}O_{10}$ | 678.734 |

TABLE A-continued
List of Exemplary Diels-Alder Adduct Compounds
| Structure | Name | Species | Molecular Formula | M.W. |
|---|---|---|---|---|
| 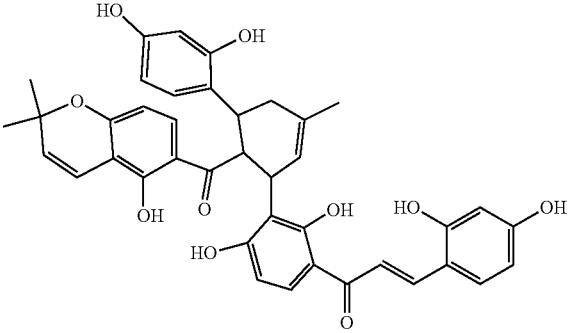 [SMILES: CC1=CC(c2c(O)ccc(C(=O)/C=C/c3ccc(O)cc3O)c2O)C(C(=O)c2ccc3c(c2O)C=CC(C)(C)O3)C(c2ccc(O)cc2O)C1] | Artonin D | *Artocarpus heterophyllus* (jackfruit) | $C_{40}H_{36}O_{10}$ | 676.718 |
| 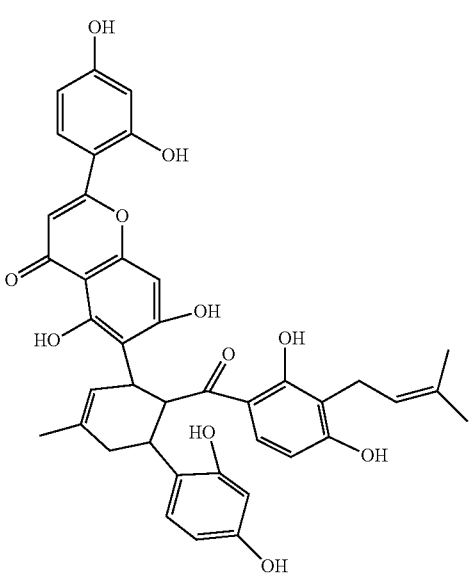 [SMILES: CC(C)=CCc1c(O)ccc(C(=O)C2C(c3c(O)cc4oc(-c5ccc(O)cc5O)cc(=O)c4c3O)C=C(C)CC2c2ccc(O)cc2O)c1O] | Artonin I | *Morus heterophyllus* | $C_{40}H_{36}O_{11}$ | 692.718 |
| 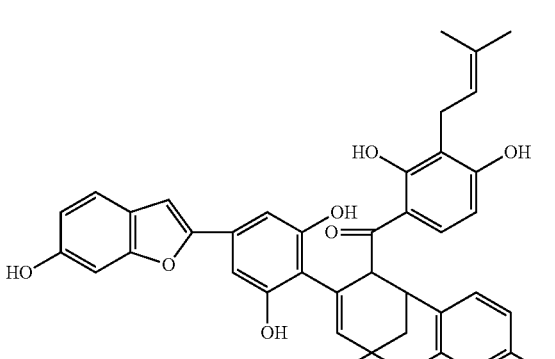 | Australisin B | *Morus australis* | $C_{39}H_{34}O_{9}$ | 646.692 |

TABLE A-continued
List of Exemplary Diels-Alder Adduct Compounds
| Structure | Name | Species | Molecular Formula | M.W. |
|---|---|---|---|---|
| 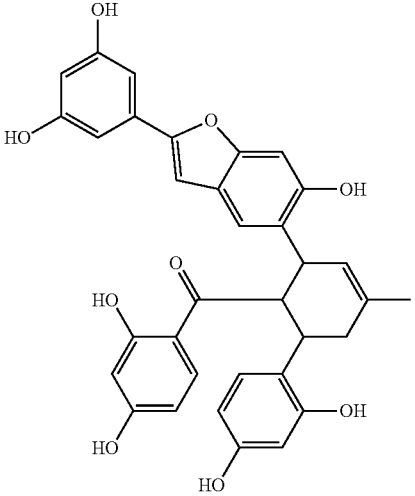 [SMILES: CC1=CC(c2cc3cc(-c4cc(O)cc(O)c4)oc3cc2O)C(C(=O)c2ccc(O)cc2O)C(c2ccc(O)cc2O)C1] | Australisin C.; 2-Epimer | *Morus australis* | $C_{34}H_{28}O_9$ | |
| 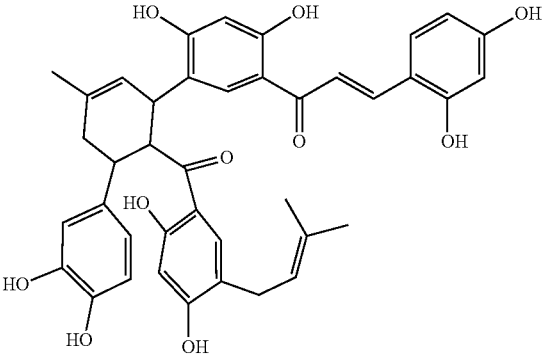 [SMILES: CC(C)=CCc1cc(C(=O)C2C(c3cc(C(=O)/C=C/c4ccc(O)cc4O)c(O)cc3O)C=C(C)CC2c2ccc(O)c(O)c2)c(O)cc1O] | Brosimone B | *Brosimopsis oblongifolia* (preferred genus name *Brosimum*) | $C_{40}H_{38}O_{10}$ | 678.734 |
| 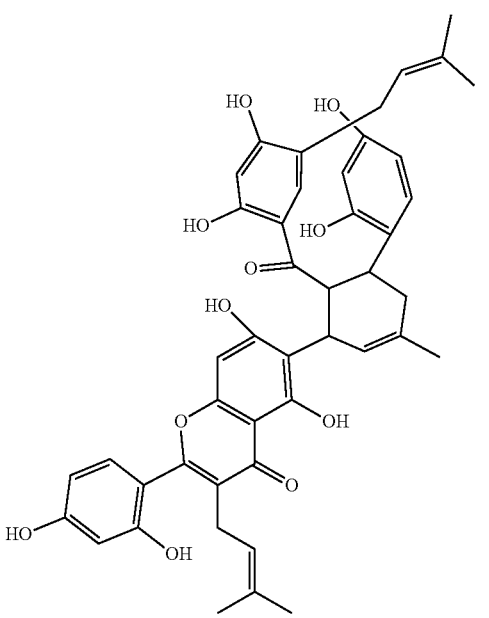 [SMILES: CC(C)=CCc1cc(C(=O)C2C(c3c(O)cc4oc(-c5ccc(O)cc5O)c(CC=C(C)C)c(=O)c4c3O)C=C(C)CC2c2ccc(O)cc2O)c(O)cc1O] | Brosimone D | *Brosimopsis oblongifolia* (preferred genus name *Brosimum*) | $C_{45}H_{44}O_{11}$ | 760.836 |

TABLE A-continued

List of Exemplary Diels-Alder Adduct Compounds

| Structure | Name | Species | Molecular Formula | M.W. |
|---|---|---|---|---|
| 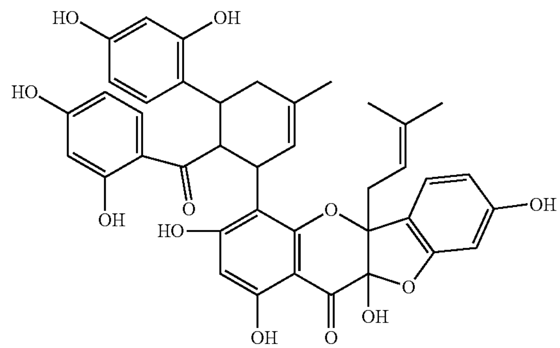 [SMILES: CC(C)=CCC12Oc3c(c(O)cc(O)c3C3C=C(C)CC(c4ccc(O)cc4O)C3C(=O)c3ccc(O)cc3O)C(=O)C1(O)Oc1cc(O)ccc12] | Cathayanon A | *Morus cathayana* | $C_{40}H_{36}O_{12}$ | 708.717 |
| 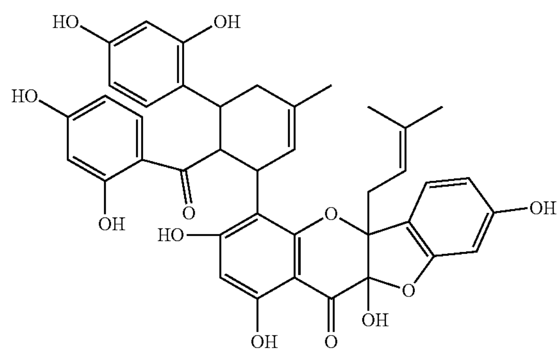 [SMILES: CC(C)=CCC12Oc3c(c(O)cc(O)c3C3C=C(C)CC(c4ccc(O)cc4O)C3C(=O)c3ccc(O)cc3O)C(=O)C1(O)Oc1cc(O)ccc12] | Cathayanon A; 14-Epimer | *Morus cathayana* | $C_{40}H_{36}O_{12}$ | 708.717 |
| 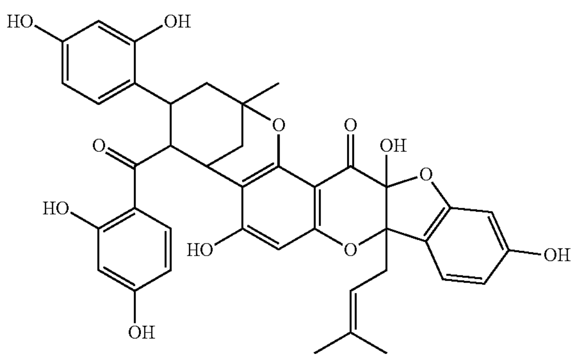 [SMILES: CC(C)=CCC12Oc3cc(O)c4c(c3C(=O)C1(O)Oc1cc(O)ccc12)OC1(C)CC(c2ccc(O)cc2O)C(C(=O)c2ccc(O)cc2O)C4C1] | Cathayanon E | *Morus cathayana* | $C_{40}H_{36}O_{12}$ | 708.717 |
| 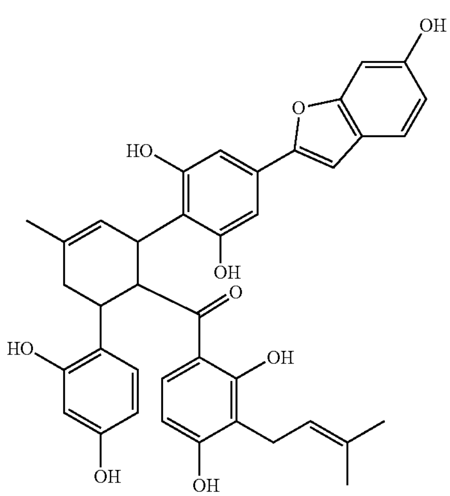 [SMILES: CC(C)=CCc1c(O)ccc(C(=O)C2C(c3c(O)cc(-c4cc5ccc(O)cc5o4)cc3O)C=C(C)CC2c2ccc(O)cc2O)c1O] | Chalcomoracin | *Morus alba* and *Morus mongolica* | $C_{39}H_{36}O_9$ | 648.708 |

TABLE A-continued
List of Exemplary Diels-Alder Adduct Compounds
| Structure | Name | Species | Molecular Formula | M.W. |
|---|---|---|---|---|
| 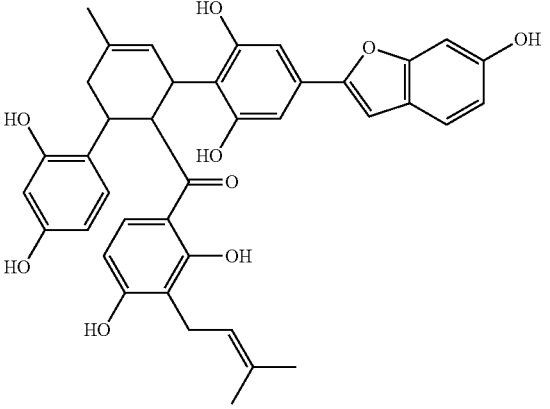 [SMILES: CC(C)=CCc1c(O)ccc(C(=O)C2C(c3c(O)cc(-c4cc5ccc(O)cc5o4)cc3O)C=C(C)CC2c2ccc(O)cc2O)c1O] | Chalcomoracin; 3",5"-Diepimer | *Sorocea muriculata* | $C_{39}H_{36}O_9$ | 648.708 |
| 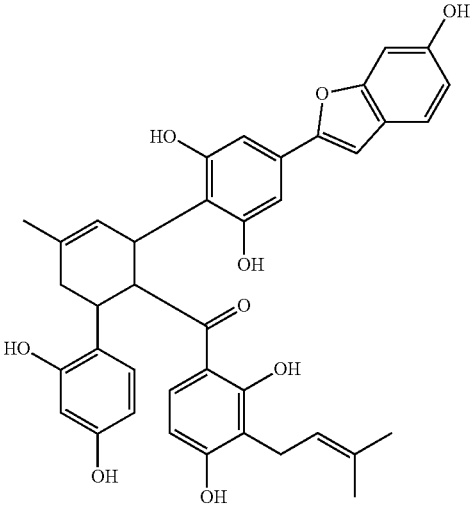 [SMILES: CC(C)=CCc1c(O)ccc(C(=O)C2C(c3c(O)cc(-c4cc5ccc(O)cc5o4)cc3O)C=C(C)CC2c2ccc(O)cc2O)c1O] | Chalcomoracin; 3"-Epimer | *Morus mongolica* | $C_{39}H_{36}O_9$ | 648.708 |
| 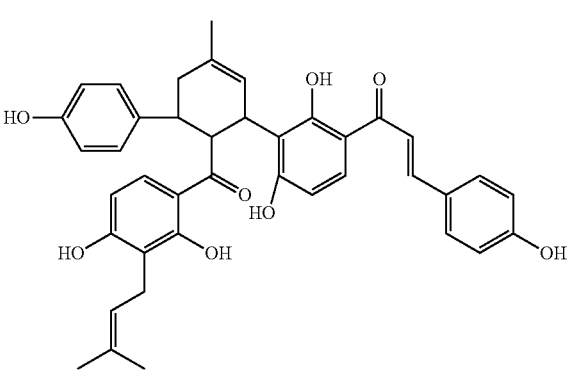 [SMILES: CC(C)=CCc1c(O)ccc(C(=O)C2C(c3c(O)ccc(C(=O)/C=C/c4ccc(O)cc4)c3O)C=C(C)CC2c2ccc(O)cc2)c1O] | Dorstenone | *Dorstenia barteri* | $C_{40}H_{38}O_8$ | 646.735 |

TABLE A-continued

List of Exemplary Diels-Alder Adduct Compounds

| Structure | Name | Species | Molecular Formula | M.W. |
|---|---|---|---|---|
| 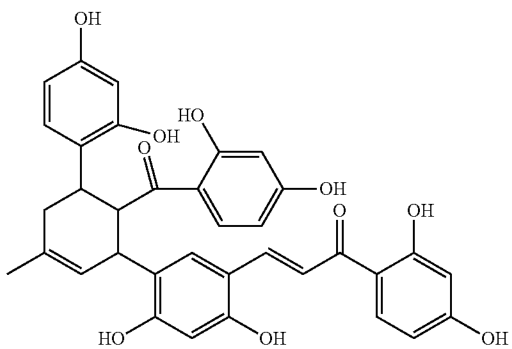 [SMILES: CC1=CC(c2cc(/C=C/C(=O)c3ccc(O)cc3O)c(O)cc2O)C(C(=O)c2ccc(O)cc2O)C(c2ccc(O)cc2O)C1] | Guangsangon C | *Morus macroura* | $C_{35}H_{30}O_{10}$ | 610.616 |
| 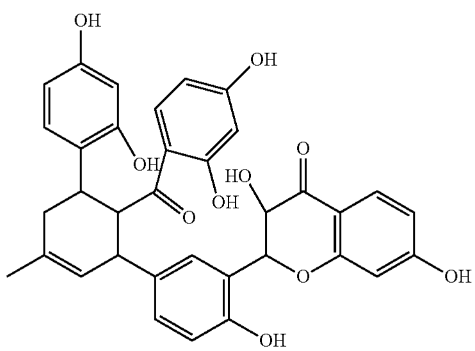 [SMILES: CC1=CC(c2ccc(O)c(C3Oc4cc(O)ccc4C(=O)C3O)c2)C(C(=O)c2ccc(O)cc2O)C(c2ccc(O)cc2O)C1] | Guangsangon D | *Morus macroura* | $C_{35}H_{30}O_{10}$ | 610.616 |
| 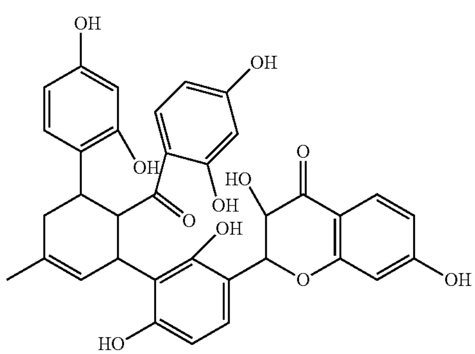 [SMILES: CC1=CC(c2c(O)ccc(C3Oc4cc(O)ccc4C(=O)C3O)c2O)C(C(=O)c2ccc(O)cc2O)C(c2ccc(O)cc2O)C1] | Guangsangon D; 2'-Deoxy, 4',6'-dihydroxy | *Morus macroura* | $C_{35}H_{30}O_{11}$ | 626.615 |
| 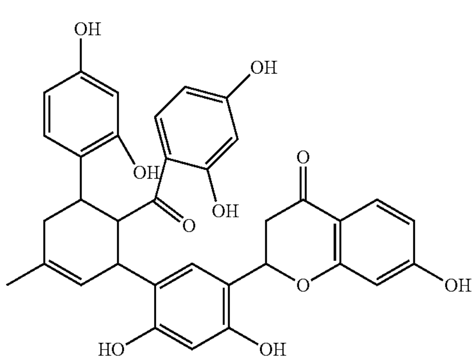 [SMILES: CC1=CC(c2cc(C3CC(=O)c4ccc(O)cc4O3)c(O)cc2O)C(C(=O)c2ccc(O)cc2O)C(c2ccc(O)cc2O)C1] | Guangsangon D; 3-Deoxy, 4'-hydroxy | *Morus macroura* and *Morus wittiorum* | $C_{35}H_{30}O_{10}$ | 610.616 |

TABLE A-continued

List of Exemplary Diels-Alder Adduct Compounds

| Structure | Name | Species | Molecular Formula | M.W. |
|---|---|---|---|---|
| 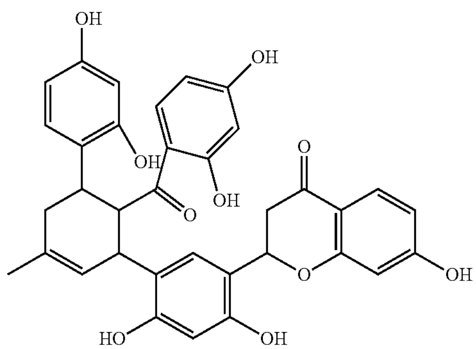 [SMILES: CC1=CC(c2cc(C3CC(=O)c4ccc(O)cc4O3)c(O)cc2O)C(C(=O)c2ccc(O)cc2O)C(c2ccc(O)cc2O)C1] | Guangsangon D; 2-Epimer, 3-deoxy, 4'-hydroxy | Morus macroura | $C_{35}H_{30}O_{10}$ | 610.616 |
| 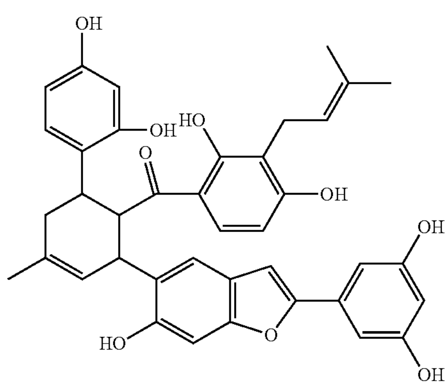 [SMILES: CC(C)=CCc1c(O)ccc(C(=O)C2C(c3cc4cc(-c5cc(O)cc(O)c5)oc4cc3O)C=C(C)CC2c2ccc(O)cc2O)c1O] | Guangsangon E | Morus macroura | $C_{39}H_{36}O_9$ | 648.708 |
| 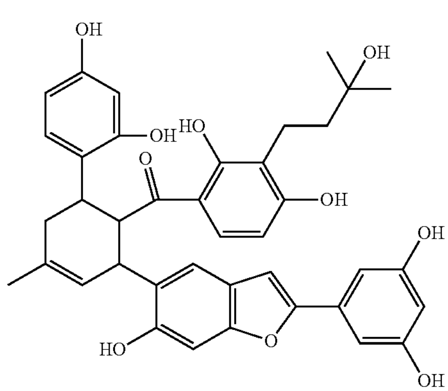 [SMILES: CC1=CC(c2cc3cc(-c4cc(O)cc(O)c4)oc3cc2O)C(C(=O)c2ccc(O)c(CCC(C)(C)O)c2O)C(c2ccc(O)cc2O)C1] | Guangsangon E; 3''-Epimer, 2'''',3''''-dihydro, 3''''-hydroxy | Morus macroura | $C_{39}H_{38}O_{10}$ | 666.723 |

TABLE A-continued

List of Exemplary Diels-Alder Adduct Compounds

| Structure | Name | Species | Molecular Formula | M.W. |
|---|---|---|---|---|
| 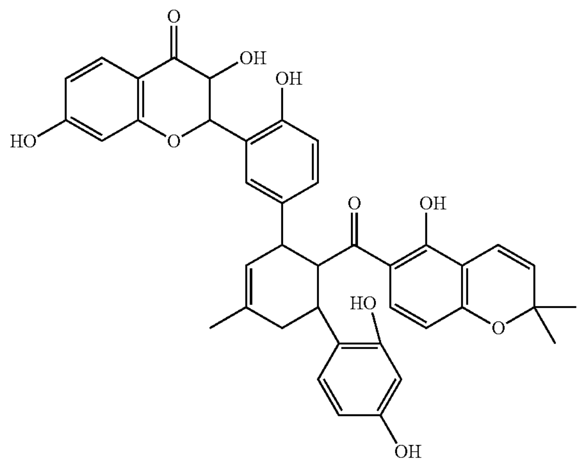 [SMILES: CC1=CC(c2ccc(O)c(C3Oc4cc(O)ccc4C(=O)C3O)c2)C(C(=O)c2ccc3c(c2O)C=CC(C)(C)O3)C(c2ccc(O)cc2O)C1] | Guangsangon F | *Morus macroura* | $C_{40}H_{36}O_{10}$ | 676.718 |
| 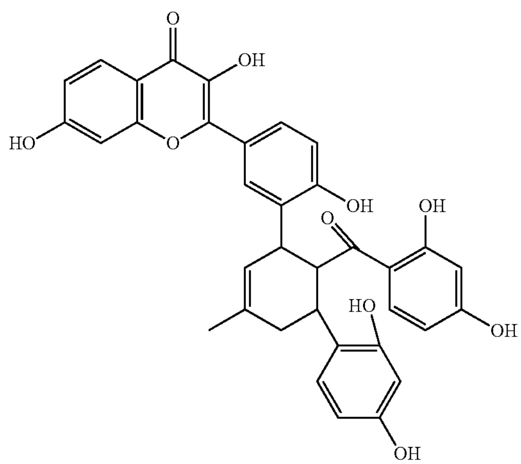 [SMILES: CC1=CC(c2cc(-c3oc4cc(O)ccc4c(=O)c3O)ccc2O)C(C(=O)c2ccc(O)cc2O)C(c2ccc(O)cc2O)C1] | Guangsangon G | *Morus macroura* | $C_{35}H_{28}O_{10}$ | 608.600 |
| 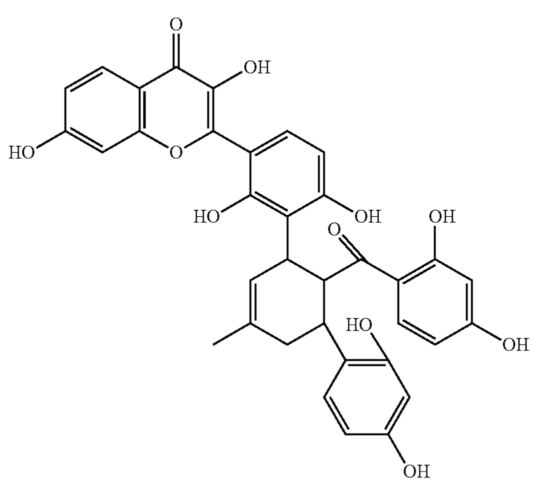 [SMILES: CC1=CC(c2c(O)ccc(-c3oc4cc(O)ccc4c(=O)c3O)c2O)C(C(=O)c2ccc(O)cc2O)C(c2ccc(O)cc2O)C1] | Guangsangon G; 1''-Epimer, 2'-hydroxy | *Morus macroura* | $C_{35}H_{28}O_{11}$ | 624.600 |

TABLE A-continued

List of Exemplary Diels-Alder Adduct Compounds

| Structure | Name | Species | Molecular Formula | M.W. |
|---|---|---|---|---|
| 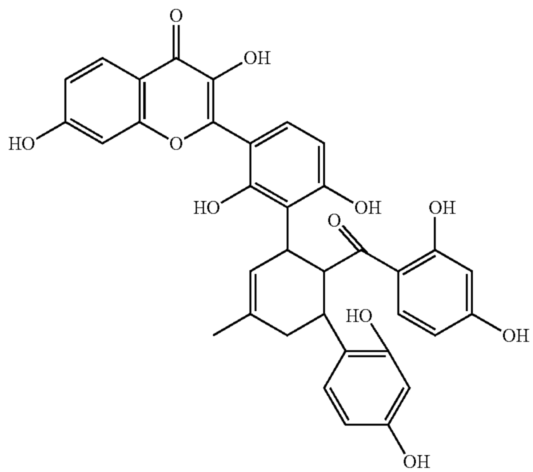 [SMILES: CC1=CC(c2c(O)ccc(-c3oc4cc(O)ccc4c(=O)c3O)c2O)C(C(=O)c2ccc(O)cc2O)C(c2ccc(O)cc2O)C1] | Guangsangon G; 2'-Hydroxy | *Morus macroura* | $C_{35}H_{28}O_{11}$ | 624.600 |
| 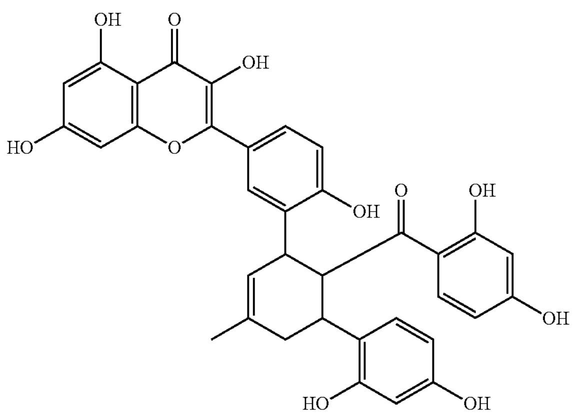 [SMILES: CC1=CC(c2cc(-c3oc4cc(O)cc(O)c4c(=O)c3O)ccc2O)C(C(=O)c2ccc(O)cc2O)C(c2ccc(O)cc2O)C1] | Guangsangon G; 5-Hydroxy | *Morus wittiorum* | $C_{35}H_{28}O_{11}$ | 625.600 |
| 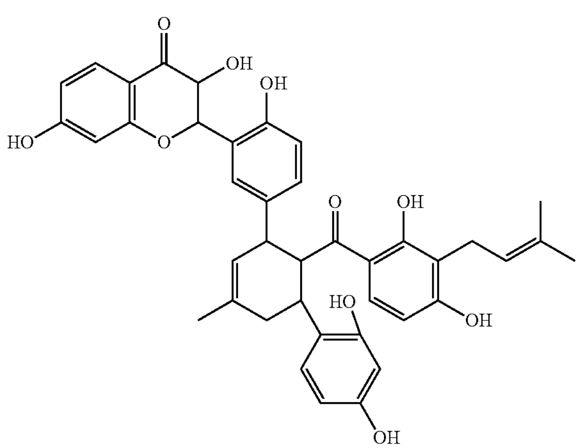 [SMILES: CC(C)=CCc1c(O)ccc(C(=O)C2C(c3ccc(O)c(C4Oc5cc(O)ccc5C(=O)C4O)c3)C=C(C)CC2c2ccc(O)cc2O)c1O] | Guangsangon H | *Morus macroura* | $C_{40}H_{38}O_{10}$ | 678.734 |

TABLE A-continued

List of Exemplary Diels-Alder Adduct Compounds

| Structure | Name | Species | Molecular Formula | M.W. |
|---|---|---|---|---|
| 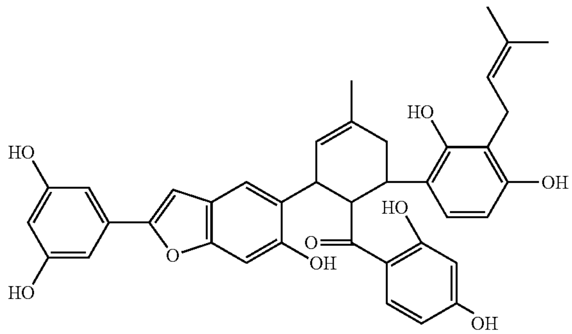 [SMILES: CC(C)=CCc1c(O)ccc(C2CC(C)=CC(c3cc4cc(-c5cc(O)cc(O)c5)oc4cc3O)C2C(=O)c2ccc(O)cc2O)c1O] | Guangsangon J | *Morus macroura* | $C_{39}H_{36}O_9$ | 648.708 |
| 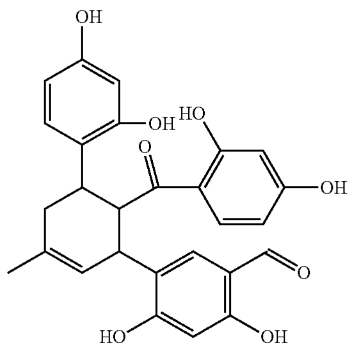 [SMILES: CC1=CC(c2cc(C=O)c(O)cc2O)C(C(=O)c2ccc(O)cc2O)C(c2ccc(O)cc2O)C1] | Guangsangon L | *Morus alba* | $C_{27}H_{24}O_8$ | 476.482 |
| 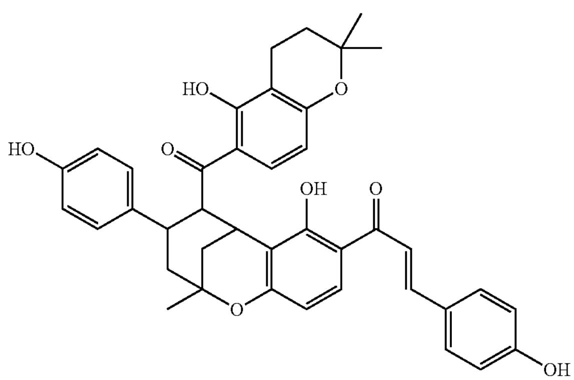 [SMILES: CC1(C)CCc2c(ccc(C(=O)C3C(c4ccc(O)cc4)CC4(C)CC3c3c(ccc(C(=O)/C=C/c5ccc(O)cc5)c3O)O4)c2O)O1] | Isobavachromene dimer | *Dorstenia zenkeri* | $C_{40}H_{38}O_8$ | 646.735 |
| 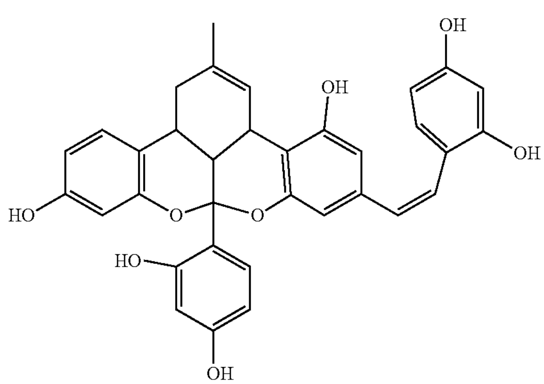 [SMILES: CC1=CC2c3c(O)cc(/C=C\c4ccc(O)cc4O)cc3OC3(c4ccc(O)cc4O)Oc4cc(O)ccc4C(C1)C23] | Kuwanol A | *Morus bombycis* | $C_{34}H_{28}O_8$ | 564.590 |

TABLE A-continued
List of Exemplary Diels-Alder Adduct Compounds
| Structure | Name | Species | Molecular Formula | M.W. |
|---|---|---|---|---|
| 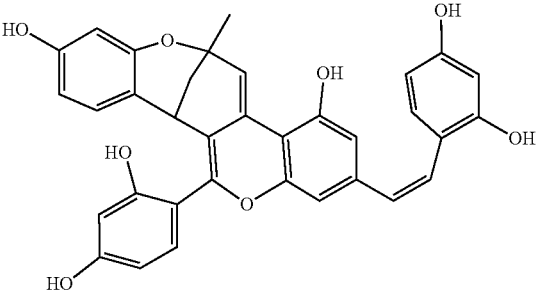 [SMILES: CC12C=C3C(=C(c4ccc(O)cc4O)Oc4cc(/C=C\c5ccc(O)cc5O)cc(O)c43)C(C1)c1ccc(O)cc1O2] | Kuwanol B | *Morus bombycis* | $C_{34}H_{26}O_8$ | 562.575 |
| 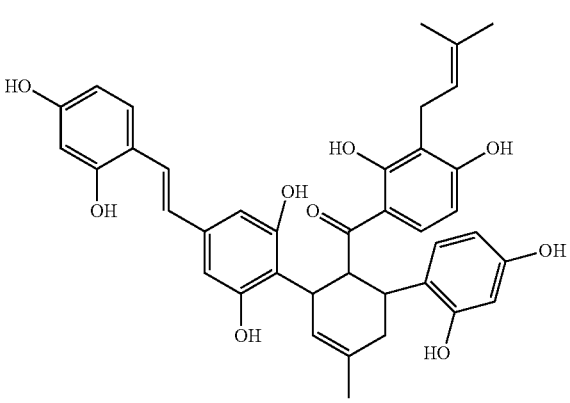 [SMILES: CC(C)=CCc1c(O)ccc(C(=O)C2C(c3c(O)cc(/C=C/c4ccc(O)cc4O)cc3O)C=C(C)CC2c2ccc(O)cc2O)c1O] | Kuwanol E | *Morus alba* (white mulberry) | $C_{39}H_{38}O_9$ | 650.724 |
| 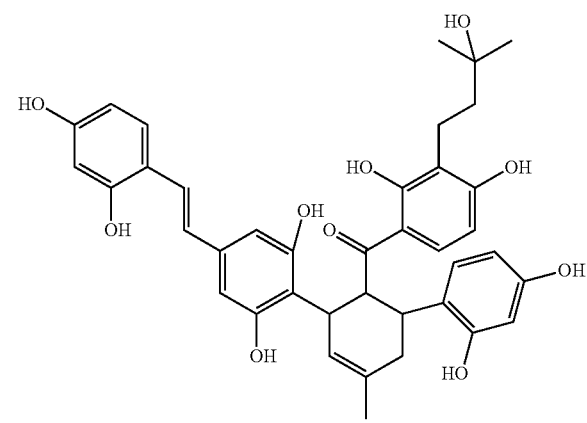 [SMILES: CC1=CC(c2c(O)cc(/C=C/c3ccc(O)cc3O)cc2O)C(C(=O)c2ccc(O)c(CCC(C)(C)O)c2O)C(c2ccc(O)cc2O)C1] | Kuwanol E; 2''',3'''-Dihydro, 3'''-hydroxy | *Sorocea ilicifolia* | $C_{39}H_{40}O_{10}$ | 668.739 |

TABLE A-continued
List of Exemplary Diels-Alder Adduct Compounds
| Structure | Name | Species | Molecular Formula | M.W. |
|---|---|---|---|---|
| 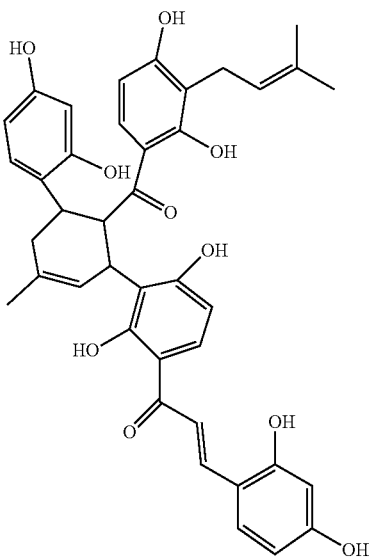 [SMILES: CC(C)=CCc1c(O)ccc(C(=O)C2C(c3c(O)ccc(C(=O)/C=C/c4ccc(O)cc4O)c3O)C=C(C)CC2c2ccc(O)cc2O)c1O] | Kuwanon J | Morus alba and from Morus bombycus and Morus nigra | $C_{40}H_{38}O_{10}$ | 678.734 |
| 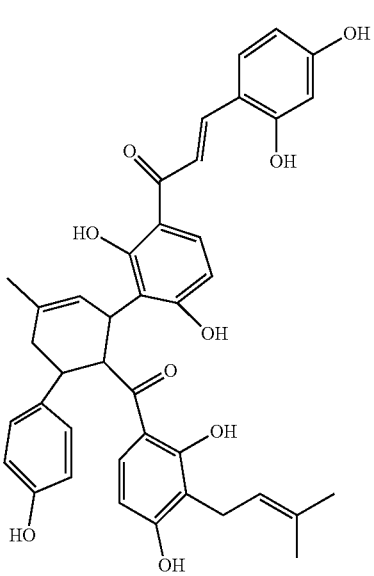 [SMILES: CC(C)=CCc1c(O)ccc(C(=O)C2C(c3c(O)ccc(C(=O)/C=C/c4ccc(O)cc4O)c3O)C=C(C)CC2c2ccc(O)cc2)c1O] | Kuwanon J; 16"-Deoxy | Morus alba (white mulberry) | $C_{40}H_{38}O_9$ | 662.735 |

TABLE A-continued

List of Exemplary Diels-Alder Adduct Compounds

| Structure | Name | Species | Molecular Formula | M.W. |
|---|---|---|---|---|
| 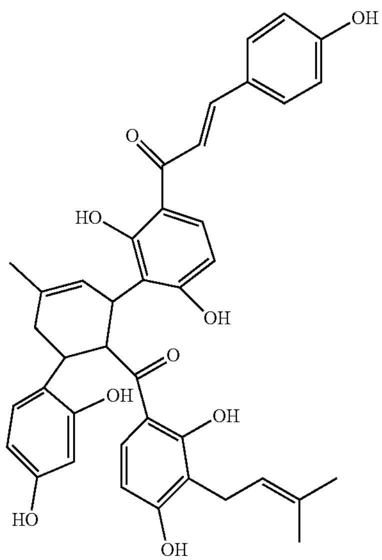 [SMILES: CC(C)=CCc1c(O)ccc(C(=O)C2C(c3c(O)ccc(C(=O)/C=C/c4ccc(O)cc4)c3O)C=C(C)CC2c2ccc(O)cc2O)c1O] | Kuwanon J: 2-Deoxy | *Morus alba* (white mulberry) | $C_{40}H_{38}O_9$ | 662.735 |
| | Kuwanon J, Δ21″, 22″-Isomer, 2-deoxy | *Morus alba* (white mulberry) | $C_{40}H_{38}O_9$ | 662.735 |

TABLE A-continued

List of Exemplary Diels-Alder Adduct Compounds

| Structure | Name | Species | Molecular Formula | M.W. |
|---|---|---|---|---|
| 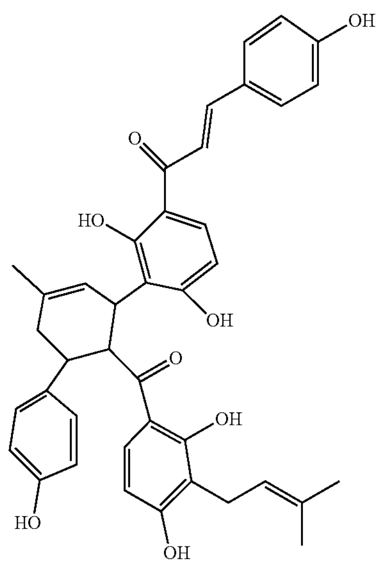 [SMILES: CC(C)=CCc1c(O)ccc(C(=O)C2C(c3c(O)ccc(C(=O)/C=C/c4ccc(O)cc4)c3O)C=C(C)CC2c2ccc(O)cc2)c1O] | Kuwanon J; 2,16''-Dideoxy | *Morus alba* (white mulberry) | $C_{40}H_{38}O_8$ | 646.735 |
| 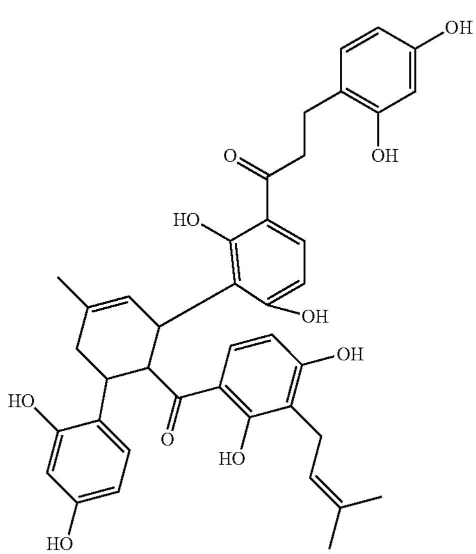 [SMILES: CC(C)=CCc1c(O)ccc(C(=O)C2C(c3c(O)ccc(C(=O)CCc4ccc(O)cc4O)c3O)C=C(C)CC2c2ccc(O)cc2O)c1O] | Kuwanon J; 2',3'-Dihydro | *Morus mongolica* | $C_{40}H_{40}O_{10}$ | 680.750 |

TABLE A-continued

List of Exemplary Diels-Alder Adduct Compounds

| Structure | Name | Species | Molecular Formula | M.W. |
|---|---|---|---|---|
|  | Kuwanon J; 1''-Epimer | Morus alba and Morus bombycus | $C_{40}H_{38}O_{10}$ | 678.734 |
|  | Kuwanon J, Δ21'', 22''-Isomer, 2-deoxy (Artonin X.) | Artocarpus heterophyllus (jackfruit) | $C_{40}H_{38}O_9$ | 662.735 |

TABLE A-continued
List of Exemplary Diels-Alder Adduct Compounds
| Structure | Name | Species | Molecular Formula | M.W. |
|---|---|---|---|---|
| 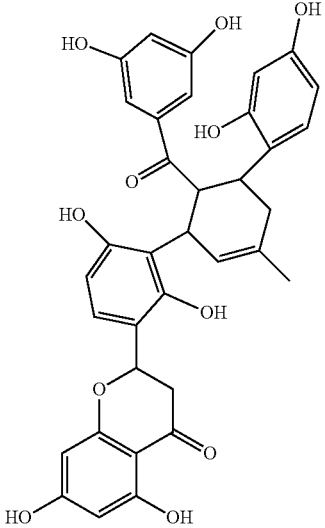 [SMILES: CC1=CC(c2c(O)ccc(C3CC(=O)c4c(O)cc(O)cc4O3)c2O)C(C(=O)c2cc(O)cc(O)c2)C(c2ccc(O)cc2O)C1] | Kuwanon L | Morus alba (white mulberry) | $C_{35}H_{30}O_{11}$ | 626.615 |
| 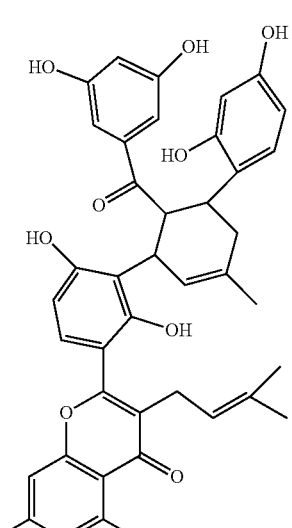 | Kuwanon L; 2,3-Didehydro, 3-(3-methyl-2-butenyl) | Morus alba (white mulberry) | $C_{40}H_{36}O_{11}$ | 692.718 |

TABLE A-continued
List of Exemplary Diels-Alder Adduct Compounds
| Structure | Name | Species | Molecular Formula | M.W. |
|---|---|---|---|---|
| 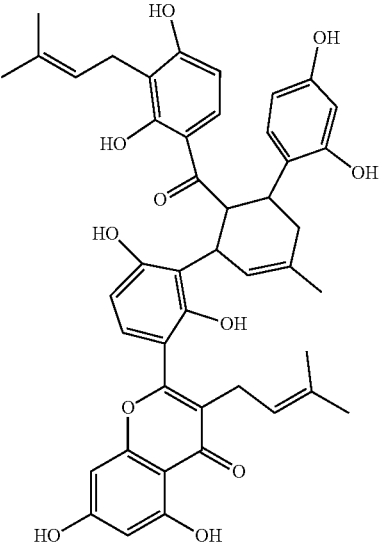 [SMILES: CC(C)=CCc1c(O)ccc(C(=O)C2C(c3c(O)ccc(-c4oc5cc(O)cc(O)c5c(=O)c4CC=C(C)C)c3O)C=C(C)CC2c2ccc(O)cc2O)c1O] | Kuwanon N | *Morus lhou* | $C_{45}H_{44}O_{11}$ | 760.836 |
| 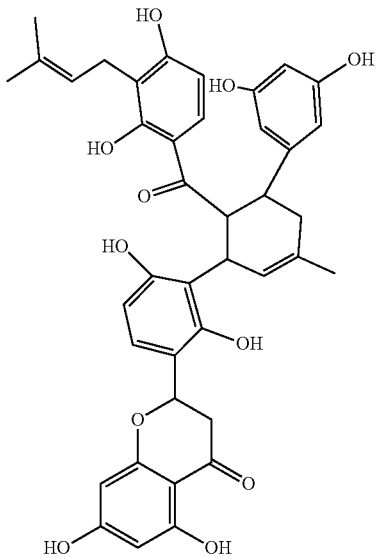 [SMILES: CC(C)=CCc1c(O)ccc(C(=O)C2C(c3c(O)ccc(C4CC(=O)c5c(O)cc(O)cc5O4)c3O)C=C(C)CC2c2cc(O)cc(O)c2)c1O] | Kuwanon O | *Morus lhou* | $C_{40}H_{38}O_{11}$ | 694.734 |

TABLE A-continued

List of Exemplary Diels-Alder Adduct Compounds

| Structure | Name | Species | Molecular Formula | M.W. |
|---|---|---|---|---|
| 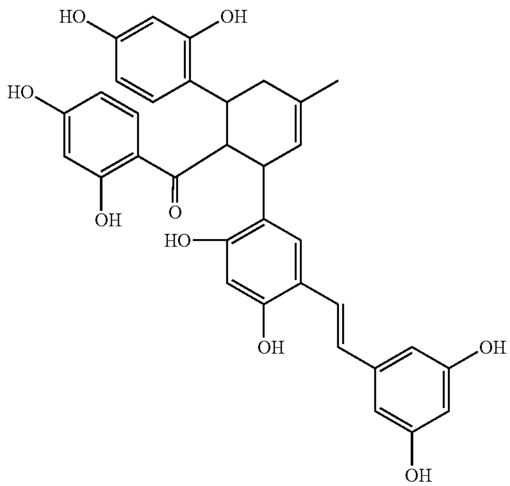 [SMILES: CC1=CC(c2cc(/C=C/c3cc(O)cc(O)c3)c(O)cc2O)C(C(=O)c2ccc(O)cc2O)C(c2ccc(O)cc2O)C1] | Kuwanon P | *Morus lhou* | $C_{34}H_{30}O_9$ | 582.606 |
| 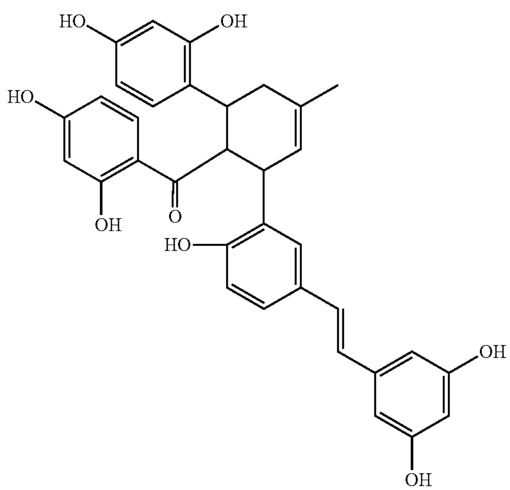 [SMILES: CC1=CC(c2cc(/C=C/c3cc(O)cc(O)c3)ccc2O)C(C(=O)c2ccc(O)cc2O)C(c2ccc(O)cc2O)C1] | Kuwanon P; 2-Deoxy | *Morus macroura* | $C_{34}H_{30}O_8$ | |
| 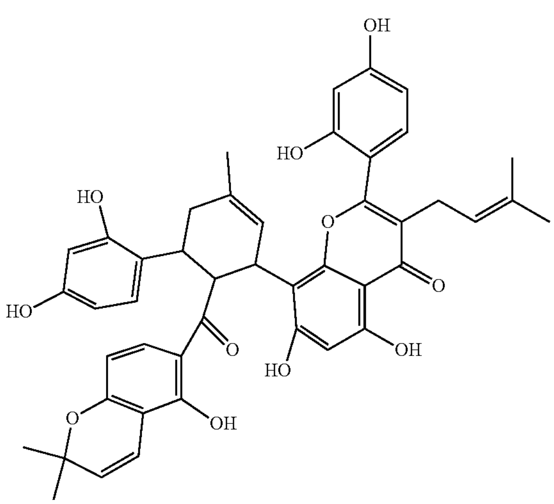 [SMILES: CC(C)=CCc1c(-c2ccc(O)cc2O)oc2c(C3C=C(C)CC(c4ccc(O)cc4O)C3C(=O)c3ccc4c(c3O)C=CC(C)(C)O4)c(O)cc(O)c2c1=O] | Kuwanon W | *Morus lhou* | $C_{45}H_{42}O_{11}$ | 758.820 |

TABLE A-continued

List of Exemplary Diels-Alder Adduct Compounds

| Structure | Name | Species | Molecular Formula | M.W. |
|---|---|---|---|---|
| 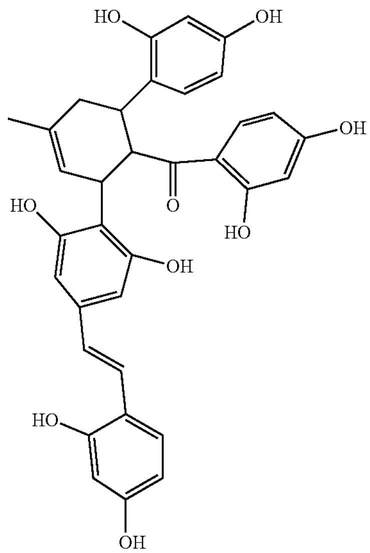 [SMILES: CC1=CC(c2c(O)cc(/C=C/c3ccc(O)cc3O)cc2O)C(C(=O)c2ccc(O)cc2O)C(c2ccc(O)cc2O)C1] | Kuwanon X | *Morus lhou* | $C_{34}H_{30}O_9$ | 582.606 |
| | Kuwanon X; 3″-Epimer | *Morus alba* (white mulberry) | $C_{34}H_{30}O_9$ | 582.606 |
| 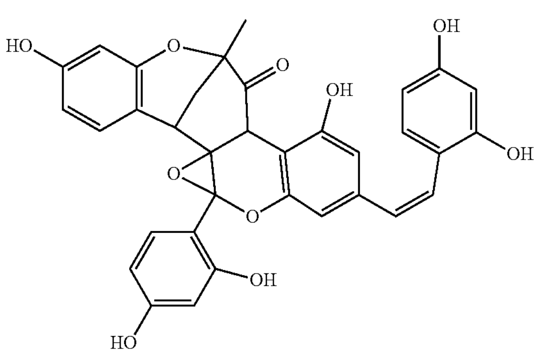 [SMILES: CC12CC(c3ccc(O)cc3O1)C13OC1(c1ccc(O)cc1O)Oc1cc(/C=C\c4ccc(O)cc4O)cc(O)c1C3C2=O] | Kuwanon Z | *Morus alba* (white mulberry) | $C_{34}H_{26}O_{10}$ | 594.573 |

TABLE A-continued
List of Exemplary Diels-Alder Adduct Compounds
| Structure | Name | Species | Molecular Formula | M.W. |
|---|---|---|---|---|
| 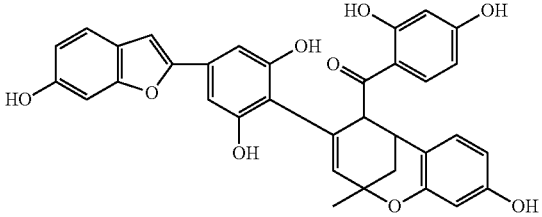 [SMILES: CC12C=C(c3c(O)cc(-c4cc5ccc(O)cc5o4)cc3O)C(C(=O)c3ccc(O)cc3O)C(C1)c1ccc(O)cc1O2] | Mongolicin C | *Morus mongolica* | $C_{34}H_{26}O_9$ | 578.574 |
| 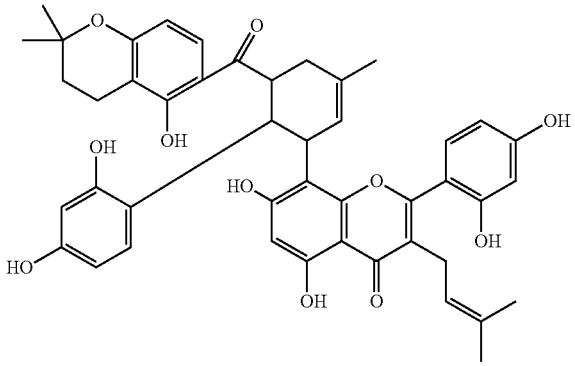 [SMILES: CC(C)=CCc1c(-c2ccc(O)cc2O)oc2c(C3C=C(C)CC(C(=O)c4ccc5c(c4O)CCC(C)(C)O5)C3c3ccc(O)cc3O)c(O)cc(O)c2c1=O] | Moracenin C | *Morus* sp. | $C_{45}H_{44}O_{11}$ | 760.836 |
| 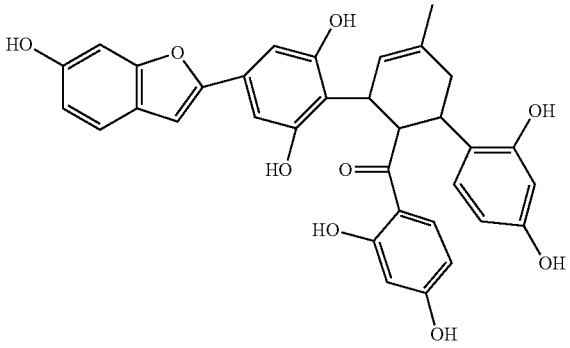 [SMILES: CC1=CC(c2c(O)cc(-c3cc4ccc(O)cc4o3)cc2O)C(C(=O)c2ccc(O)cc2O)C(c2ccc(O)cc2O)C1] | Mulberrofuran C | *Morus bombycis* (Moraceae) | | |
| 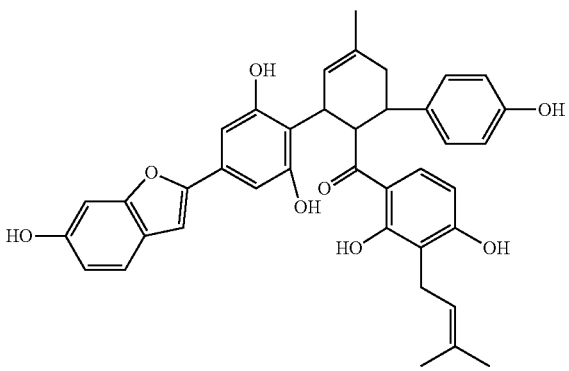 [SMILES: CC(C)=CCc1c(O)ccc(C(=O)C2C(c3c(O)cc(-c4cc5ccc(O)cc5o4)cc3O)C=C(C)CC2c2ccc(O)cc2)c1O] | Mulberrofuran E | *Morus alba* (white mulberry) (Moraceae) | $C_{39}H_{36}O_8$ | 632.709 |

TABLE A-continued
List of Exemplary Diels-Alder Adduct Compounds
| Structure | Name | Species | Molecular Formula | M.W. |
|---|---|---|---|---|
| 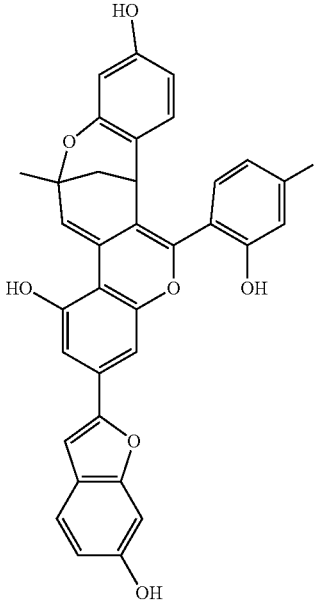 | Mulberrofuran I | *Morus bombycis* | $C_{34}H_{24}O_8$ | 560.559 |
| 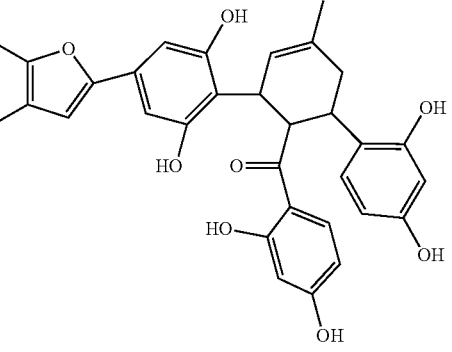 | Mulberrofuran J | *Morus lhou* | $C_{34}H_{28}O_9$ | 580.590 |
| 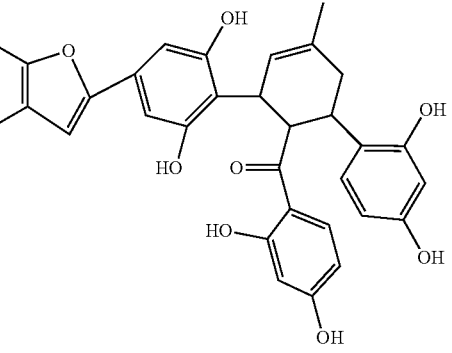 | Mulberrofuran J, 2-Epimer | *Morus bombycis* | | |

TABLE A-continued

List of Exemplary Diels-Alder Adduct Compounds

| Structure | Name | Species | Molecular Formula | M.W. |
|---|---|---|---|---|
| 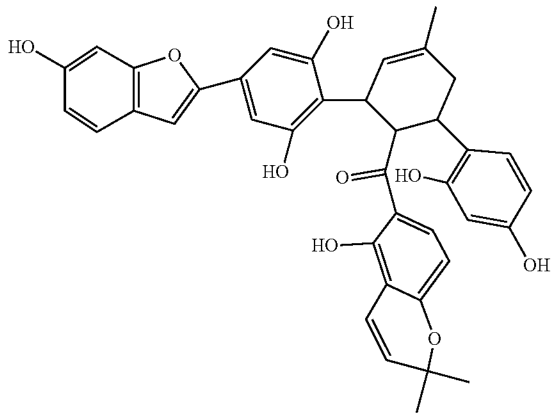 [SMILES: CC1=CC(c2c(O)cc(-c3cc4ccc(O)cc4o3)cc2O)C(C(=O)c2ccc3c(c2O)C=CC(C)(C)O3)C(c2ccc(O)cc2O)C1] | Mulberrofuran O | Morus alba | | 646.692 |
| 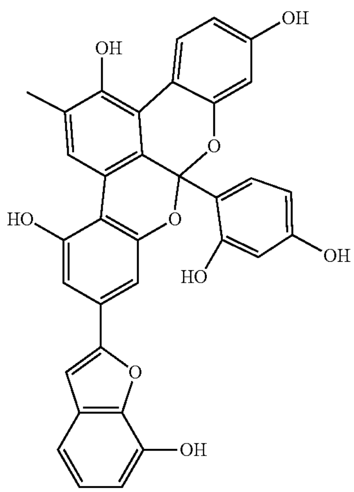 [SMILES: Cc1cc2c3c(c1O)-c1ccc(O)cc1OC3(c1ccc(O)cc1O)Oc1cc(-c3cc4cccc(O)c4o3)cc(O)c1-2] | Mulberrofuran P | Morus alba (white mulberry) | $C_{34}H_{22}O_9$ | 574.542 |
| 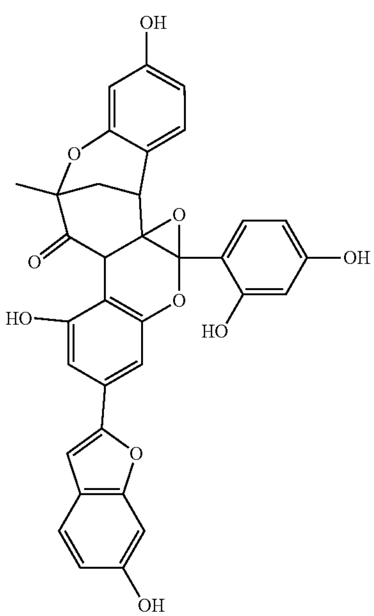 [SMILES: CC12CC(c3ccc(O)cc3O1)C13OC1(c1ccc(O)cc1O)Oc1cc(-c4cc5ccc(O)cc5o4)cc(O)c1C3C2=O] | Mulberrofuran Q | Morus alba (white mulberry) | $C_{34}H_{24}O_{10}$ | 592.558 |

TABLE A-continued
List of Exemplary Diels-Alder Adduct Compounds
| Structure | Name | Species | Molecular Formula | M.W. |
|---|---|---|---|---|
| 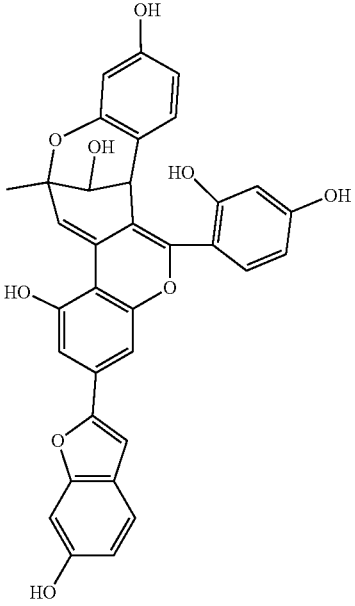 [SMILES: CC12C=C3C(=C(c4ccc(O)cc4O)Oc4cc(-c5cc6ccc(O)cc6o5)cc(O)c43)C(c3ccc(O)cc3O1)C2O] | Mulberrofuran S | *Morus alba* (white mulberry) | $C_{34}H_{24}O_9$ | 576.558 |
| 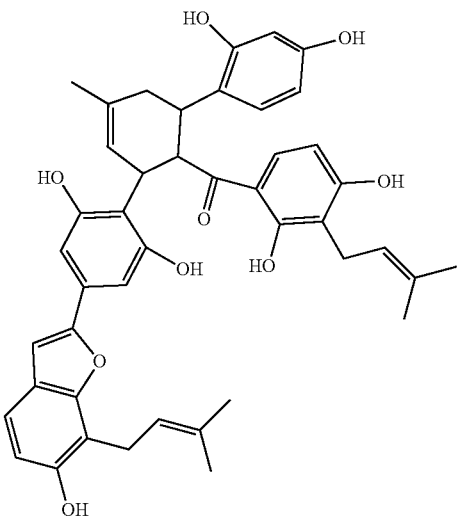 [SMILES: CC(C)=CCc1c(O)ccc(C(=O)C2C(c3c(O)cc(-c4cc5ccc(O)c(CC=C(C)C)c5o4)cc3O)C=C(C)CC2c2ccc(O)cc2O)c1O] | Mulberrofuran T | *Morus alba* (white mulberry) | $C_{44}H_{44}O_9$ | 716.826 |

TABLE A-continued

List of Exemplary Diels-Alder Adduct Compounds

| Structure | Name | Species | Molecular Formula | M.W. |
|---|---|---|---|---|
| 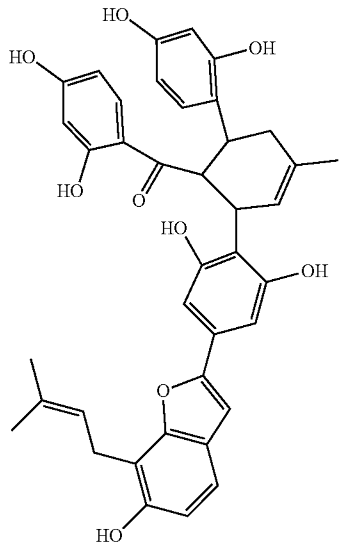 [SMILES: CC(C)=CCc1c(O)ccc2cc(-c3cc(O)c(C4C=C(C)CC(c5ccc(O)cc5O)C4C(=O)c4ccc(O)cc4O)c(O)c3)oc12] | Mulberrofuran U | *Morus insignis* | $C_{39}H_{36}O_9$ | 648.708 |
| 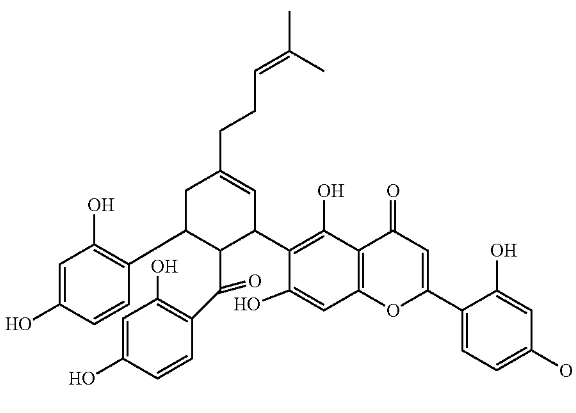 [SMILES: CC(C)=CCCC1=CC(c2c(O)cc3oc(-c4ccc(O)cc4O)cc(=O)c3c2O)C(C(=O)c2ccc(O)cc2O)C(c2ccc(O)cc2O)C1] | Multicaulisin | *Morus multicaulis* | $C_{40}H_{36}O_{11}$ | 692.718 |
| 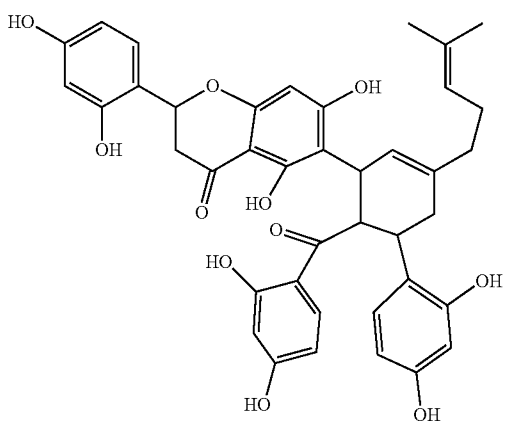 [SMILES: CC(C)=CCCC1=CC(c2c(O)cc3c(c2O)C(=O)CC(c2ccc(O)cc2O)O3)C(C(=O)c2ccc(O)cc2O)C(c2ccc(O)cc2O)C1] | Sanggenol G | *Morus cathayana* | $C_{30}H_{34}O_7$ | 694.734 |

TABLE A-continued
List of Exemplary Diels-Alder Adduct Compounds
| Structure | Name | Species | Molecular Formula | M.W. |
|---|---|---|---|---|
| 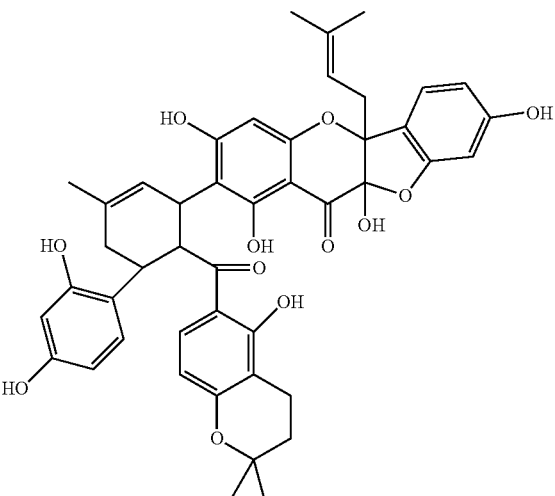 [SMILES: CC(C)=CCC12Oc3cc(O)c(C4C=C(C)CC(c5ccc(O)cc5O)C4C(=O)c4ccc5c(c4O)CCC(C)(C)O5)c(O)c3C(=O)C1(O)Oc1cc(O)ccc12] | Sanggenol J | *Morus cathayana* | $C_{45}H_{44}O_{12}$ | 776.835 |
| 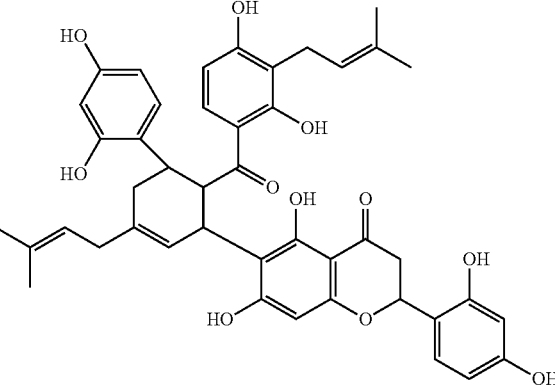 [SMILES: CC(C)=CCC1=CC(c2c(O)cc3c(c2O)C(=O)CC(c2ccc(O)cc2O)O3)C(C(=O)c2ccc(O)c(CC=C(C)C)c2O)C(c2ccc(O)cc2O)C1] | Sanggenol M | *Morus mongolica* | $C_{44}H_{44}O_{11}$ | 748.825 |
| 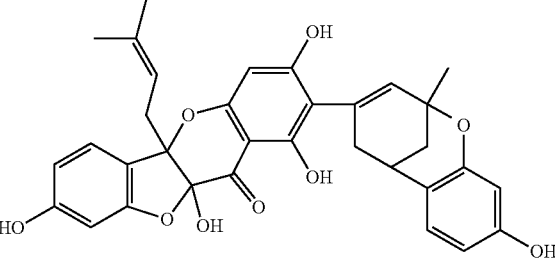 | Sanggenon B | *Morus* | $C_{33}H_{30}O_9$ | 570.595 |
| 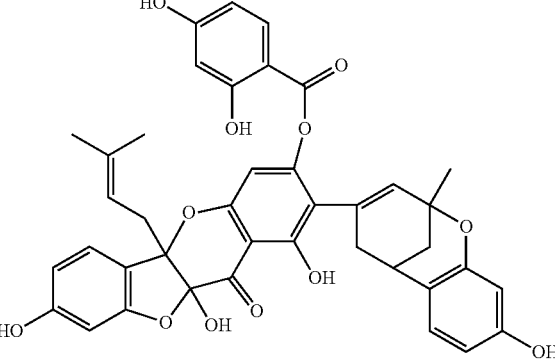 [SMILES: CC(C)=CCC12Oc3cc(OC(=O)c4ccc(O)cc4O)c(C4=CC5(C)CC(C4)c4ccc(O)cc4O5)c(O)c3C(=O)C1(O)Oc1cc(O)ccc12] | Sanggenol B; 7-O-(2,4-Dihydroxybenzoyl) (Sanggenon S) | *Morus* sp | $C_{40}H_{34}O_{12}$ | 706.701 |

TABLE A-continued
List of Exemplary Diels-Alder Adduct Compounds
| Structure | Name | Species | Molecular Formula | M.W. |
|---|---|---|---|---|
| 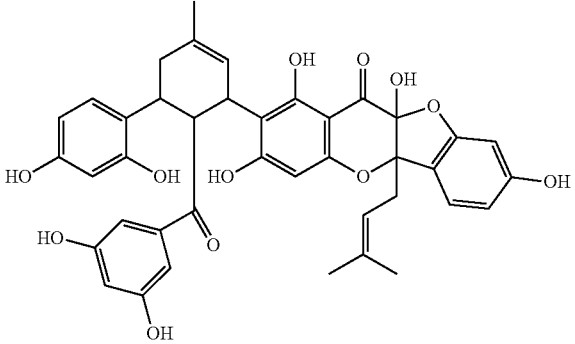 [SMILES: CC(C)=CCC12Oc3cc(O)c(C4C=C(C)CC(c5ccc(O)cc5O)C4C(=O)c4cc(O)cc(O)c4)c(O)c3C(=O)C1(O)Oc1cc(O)ccc12] | Sanggenon D | *Morus cathayana* | $C_{40}H_{36}O_{12}$ | 708.717 |
| 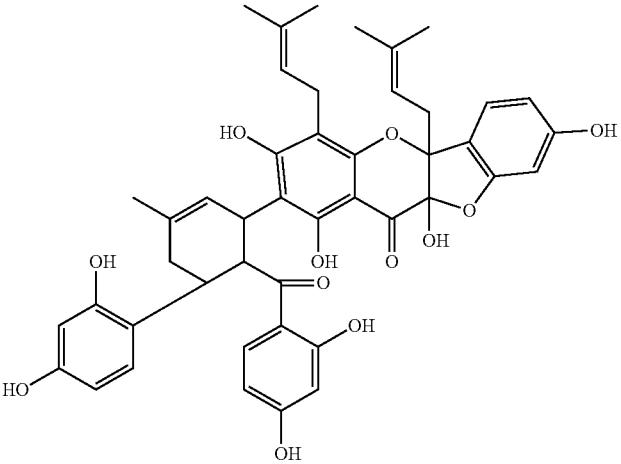 [SMILES: CC(C)=CCc1c(O)c(C2C=C(C)CC(Cc3ccc(O)cc3O)C2C(=O)c2ccc(O)cc2O)c(O)c2c1OC1(CC=C(C)C)c3ccc(O)cc3OC1(O)C2=O] | Sanggenon E | *Morus* Spp. | $C_{45}H_{44}O_{12}$ | 776.835 |
| 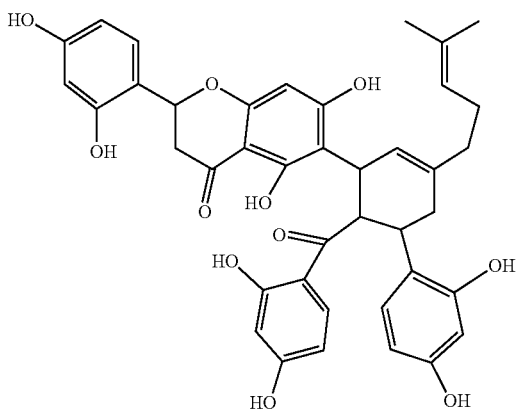 [SMILES: CC(C)=CCCC1=CC(c2c(O)cc3c(c2O)C(=O)CC(c2ccc(O)cc2O)O3)C(C(=O)c2ccc(O)cc2O)C(c2ccc(O)cc2O)C1] | Sanggenon G | *Morus alba* | $C_{40}H_{38}O_{11}$ | 694.734 |

TABLE A-continued
List of Exemplary Diels-Alder Adduct Compounds
| Structure | Name | Species | Molecular Formula | M.W. |
|---|---|---|---|---|
| 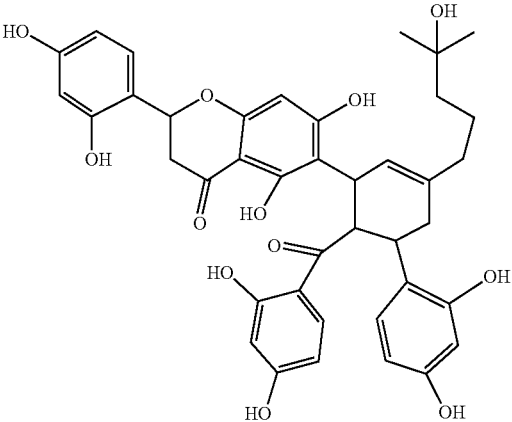 [SMILES: CC(C)(O)CCCC1=CC(c2c(O)cc3c(c2O)C(=O)CC(c2ccc(O)cc2O)O3)C(C(=O)c2ccc(O)cc2O)C(c2ccc(O)cc2O)C1] | Sanggenon G; 14,15-Dihydro, 15-hydroxy | *Morus* sp. | $C_{40}H_{40}O_{12}$ | 712.749 |
| 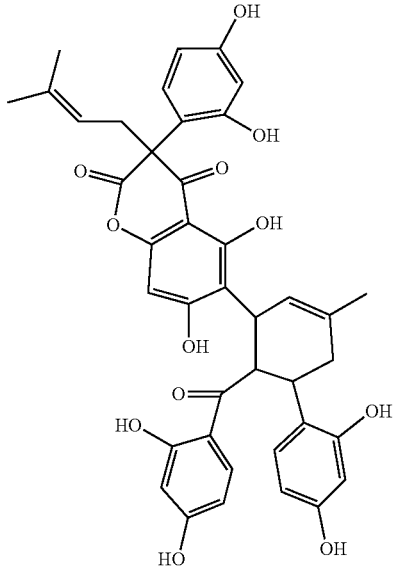 [SMILES: CC(C)=CCC1(c2ccc(O)cc2O)C(=O)Oc2cc(O)c(C3C=C(C)CC(c4ccc(O)cc4O)C3C(=O)c3ccc(O)cc3O)c(O)c2C1=O] | Sanggenon Q | *Morus mongolica* | $C_{40}H_{36}O_{12}$ | 708.717 |
| 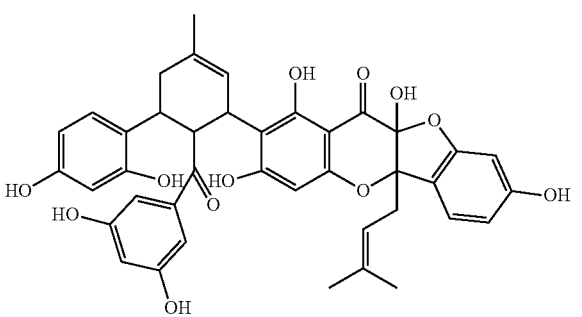 [SMILES: CC(C)=CCC12Oc3cc(O)c(C4C=C(C)CC(c5ccc(O)cc5O)C4C(=O)c4cc(O)cc(O)c4)c(O)c3C(=O)C1(O)Oc1cc(O)ccc12] | Sanggenon D; 3'-Epimer | *Morus cathayana* | $C_{40}H_{36}O_{12}$ | 708.717 |

TABLE A-continued

List of Exemplary Diels-Alder Adduct Compounds

| Structure | Name | Species | Molecular Formula | M.W. |
|---|---|---|---|---|
| 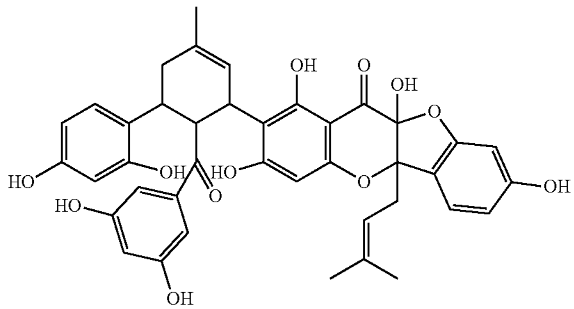 [SMILES: CC(C)=CCC12Oc3cc(O)c(C4C=C(C)CC(c5ccc(O)cc5O)C4C(=O)c4cc(O)cc(O)c4)c(O)c3C(=O)C1(O)Oc1cc(O)ccc12] | Sanggenon D; 2,3,3'-Triepimer | *Morus cathayana* | $C_{40}H_{36}O_{12}$ | 708.717 |
| 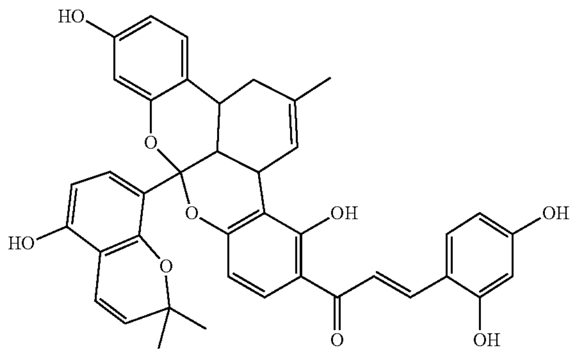 [SMILES: CC1=CC2c3c(ccc(C(=O)/C=C/c4ccc(O)cc4O)c3O)OC3(c4ccc(O)c5c4OC(C)(C)C=C5)Oc4cc(O)ccc4C(C1)C23] | Sorocein B | *Sorocea bonplandii* | $C_{40}H_{34}O_9$ | 658.703 |
| 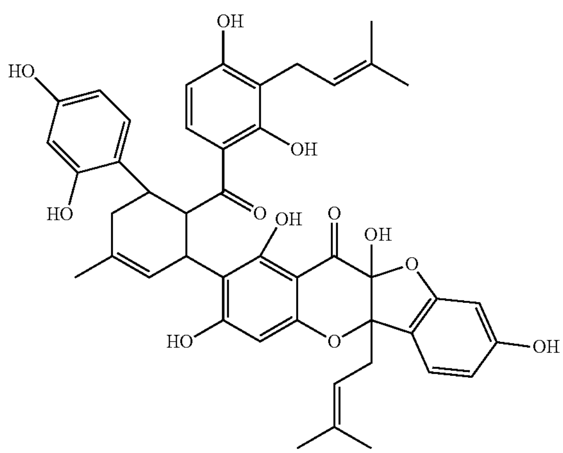 [SMILES: CC(C)=CCc1c(O)ccc(C(=O)C2C(c3c(O)cc4c(c3O)C(=O)C3(O)Oc5cc(O)ccc5C3(CC=C(C)C)O4)C=C(C)CC2c2ccc(O)cc2O)c1O] | Sorocein H | *Sorocea bonplandii* (Moraceae) and *Morus* spp. | $C_{45}H_{44}O_{12}$ | 776.835 |
| 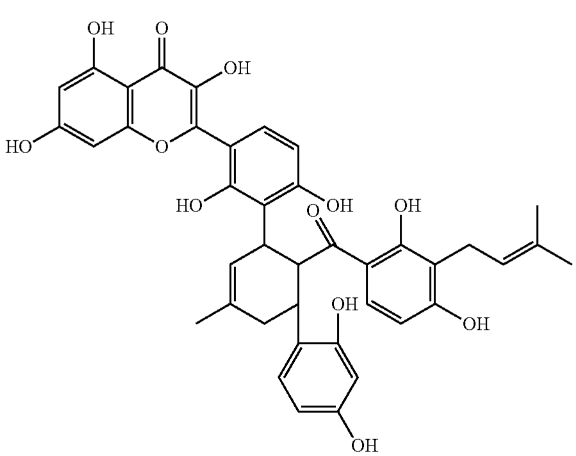 [SMILES: CC(C)=CCc1c(O)ccc(C(=O)C2C(c3c(O)ccc(-c4oc5cc(O)cc(O)c5c(=O)c4O)c3O)C=C(C)CC2c2ccc(O)cc2O)c1O] | Wittiorumin B | *Morus wittiorum* | $C_{40}H_{36}O_{12}$ | 708.717 |

TABLE A-continued

List of Exemplary Diels-Alder Adduct Compounds

| Structure | Name | Species | Molecular Formula | M.W. |
|---|---|---|---|---|
| 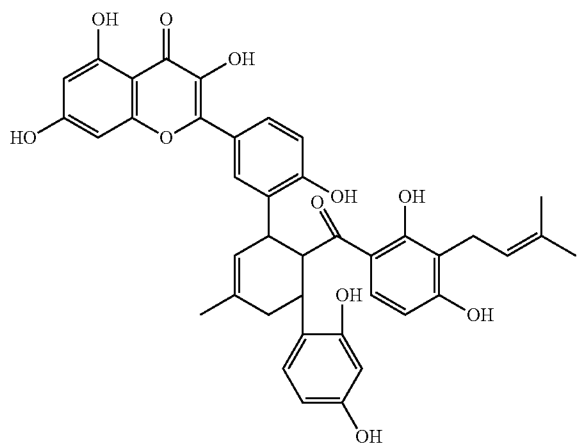 [SMILES: CC(C)=CCc1c(O)ccc(C(=O)C2C(c3cc(-c4oc5cc(O)cc(O)c5c(=O)c4O)ccc3O)C=C(C)CC2c2ccc(O)cc2O)c1O] | Wittiorumin B; 1''-Epimer, 2'-deoxy | *Morus wittiorum* | $C_{40}H_{36}O_{11}$ | 692.718 |
| 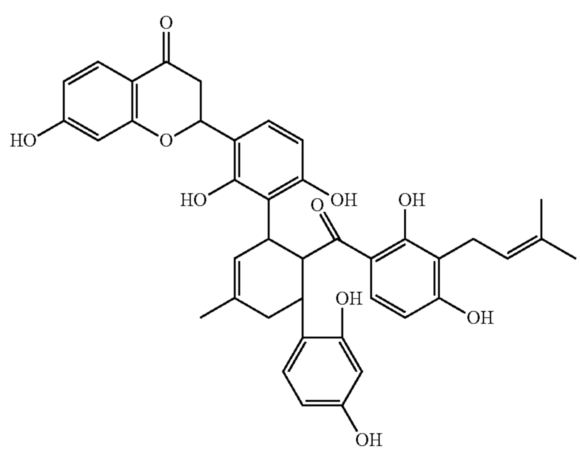 [SMILES: CC(C)=CCc1c(O)ccc(C(=O)C2C(c3c(O)ccc(C4CC(=O)c5ccc(O)cc5O4)c3O)C=C(C)CC2c2ccc(O)cc2O)c1O] | Wittiorumin E | *Morus wittiorum* | $C_{40}H_{38}O_{10}$ | 678.734 |
| 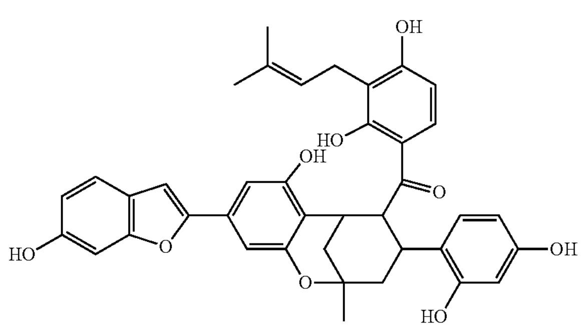 [SMILES: CC(C)=CCc1c(O)ccc(C(=O)C2C(c3ccc(O)cc3O)CC3(C)CC2c2c(O)cc(-c4cc5ccc(O)cc5o4)cc2O3)c1O] | Wittiorumin F | *Morus wittiorum* | $C_{39}H_{36}O_{9}$ | 648.708 |
| 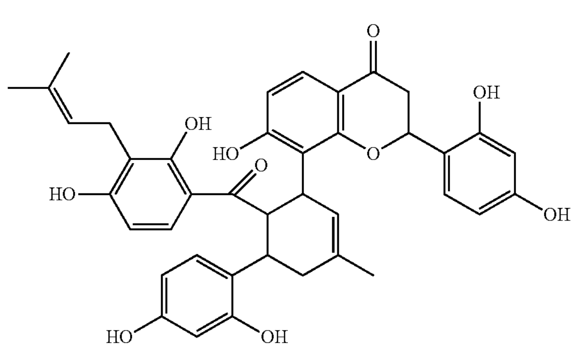 [SMILES: CC(C)=CCc1c(O)ccc(C(=O)C2C(c3c(O)ccc4c3OC(c3ccc(O)cc3O)CC4=O)C=C(C)CC2c2ccc(O)cc2O)c1O] | Wittiorumin G | *Morus wittiorum* | $C_{40}H_{38}O_{10}$ | 678.734 |

TABLE A-continued

List of Exemplary Diels-Alder Adduct Compounds

| Structure | Name | Species | Molecular Formula | M.W. |
|---|---|---|---|---|
| 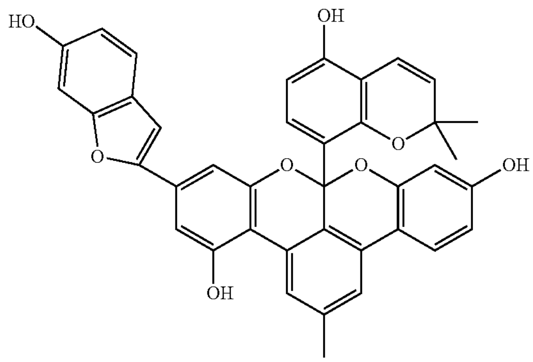 [SMILES: Cc1cc2c3c(c1)-c1c(O)cc(-c4cc5ccc(O)cc5o4)cc1OC3(c1ccc(O)c3c1OC(C)(C)C=C3)Oc1cc(O)ccc1-2] | Yunanensin A | *Moru yunnanesis* | $C_{39}H_{28}O_8$ | 624.645 |

Compounds in Table A and Examples 3, 5, and 6 can be extracted, isolated or purified from the indicated plant species or certain plant parts (e.g., from the bark, trunk, trunk bark, stem bark, root, root bark, bark surface (such as periderm or polyderm, which may include phellem, phellogen, phelloderm, or any combination thereof), leaves, fruits, flowers, other plant parts, or any combination thereof) or can be prepared synthetically or semi-synthetically as described in more detail in PCT Application No. PCT/US2013/43188, which methods of synthesis are incorporated herein by reference. In certain embodiments, one or more compounds of Table A and Examples 3, 5, and 6 are enriched for or are the major active ingredients in an extract of the indicated plant species, wherein the enriched extract is obtained from a whole plant or certain plant parts, such as leaves, bark, trunk, trunk bark, stems, stem bark, twigs, tubers, root, root bark, bark surface (such as periderm or polyderm, which may include phellem, phellogen, phelloderm, or any combination thereof), young shoots, rhizomes, seed, fruit, androecium, gynoecium, calyx, stamen, petal, sepal, carpel (pistil), flower, or any combination thereof.

In further embodiments, major active ingredients in an extract of *Morus* comprise prenylated flavonoids and stilbenes (such as those provided in Table A and Examples 3, 5, and 6), wherein the extract is enriched for these active ingredients from root bark, leaves, twigs, or a combination thereof. In certain embodiments, a *Morus* extract is enriched for prenylated flavonoids and stilbenes, wherein the extract comprises from about 1% to about 25% prenylated flavonoids and from about 1% to about 25% stilbenes, or wherein the extract comprises from about 2% to about 6% prenylated flavonoids and from about 2% to about 6% stilbenes, or wherein the extract comprises at least 3% prenylated flavonoids and at least 3% stilbenes (weight to weight).

In certain embodiments, provided herein are *Morus* extracts enriched for one or more prenylated flavonoids or chalconoids and one or more stilbenes, wherein the one or more prenylated flavonoids are compounds having a structure of Formula (III) or (IV):

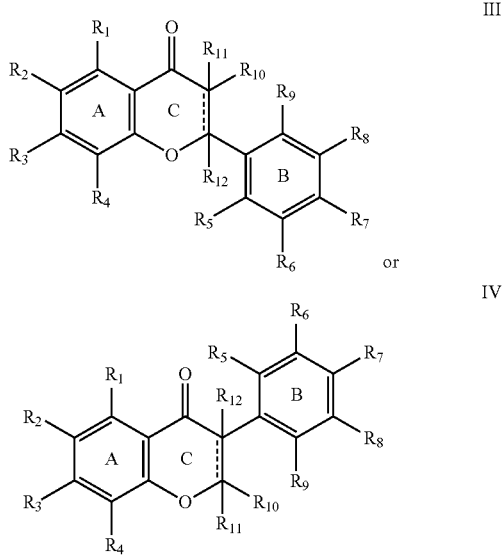

or a pharmaceutically or nutraceutically acceptable salt, tautomer, glycoside, prodrug or stereoisomer thereof, wherein $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, aralkylcarbonyl or a bond to a compound of structure (III) or (IV); or one of $R_1$—$R_{12}$ joins with another one of $R_1$—$R_{12}$ to form a ring, and the remaining $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied; the chalcanoid is a compound of structure (V):

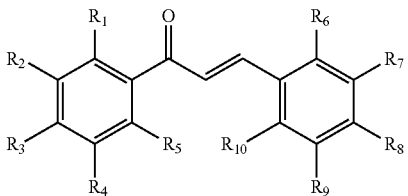

or a pharmaceutically or nutraceutically acceptable salt, tautomer, glycoside, prodrug or stereoisomer thereof, wherein $R_1$—$R_{10}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, or aralkylcarbonyl, provided that all valencies are satisfied; and the one or more stilbenes are compounds having a structure of Formula (I) or (II):

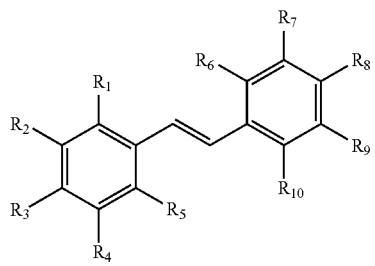

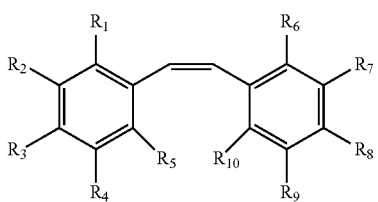

wherein $R_1$—$R_{10}$ are each independently a H, hydroxyl, glycoside, prenyl, flavonoid, chalcone, halogen, sulfhydryl, amino, aldehyde, $C_{1-12}$ alkyl, $C_{1-12}$ alkenyl, $C_{1-12}$ alkoxy, $C_{1-12}$ alkthio, $C_{1-12}$ alkyamino, aryl, heteroaryl, aralkyl, alkylcarbonyl, or aralkylcarbonyl.

In further embodiments, the one or more prenylayted flavonoids are compounds having a structure of Formula (III), (IV) or (V), wherein the optional double bond is present in ring C, $R_{11}$ and $R_{12}$ are absent, and $R_{10}$ is a prenyl group. In still further embodiments, the one or more prenylayted flavonoids are compounds having a structure of Formula (III), (IV) or (V), wherein the at least one of $R_1$—$R_9$ is a prenyl group and $R_{10}$—$R_{12}$ are independently H or hydroxyl. In certain specific embodiments, the prenylated flavonoids include Albanin G, Kuwanon G, Morusin, morusinol, Sanggenon, isoxanthoumol, glabridin, cathayanon A, or any combination thereof. In certain embodiments, the one or more stilbenes are compounds having a structure of Formula (I) or (II), wherein $R_1$—$R_{10}$ are each independently a H, hydroxyl, glycoside, or $C_{1-4}$ alkoxy. In further embodiments, the one or more stilbenes are compounds having a structure of Formula (I) or (II), wherein $R_1$, $R_5$, $R_6$ and $R_{10}$ are H. In still further embodiments, the one or more stilbenes are compounds having a structure of Formula (I) or (II), wherein $R_2$ is a glucoside, or $R_2$ and $R_6$ are glycosides, and one or more of $R_4$, $R_9$, and $R_{10}$ are hydroxyl. In yet further embodiments, the one or more stilbenes are compounds having a structure of Formula (I) or (II), wherein $R_1$, $R_5$, $R_6$ are H, and one or more of $R_2$—$R_4$ and $R_7$—$R_{10}$ are independently hydroxyl, $C_{1-3}$ alkoxy, or any combination thereof. In certain specific embodiments, a stilbene compound includes oxyresveratrol, resveratrol, piceatannol, pinosylvin, 3,4'-dihydroxystilbene, combretastatin A-1, pterostilbene, rhapontigenin, and a stilbene glycoside includes mulberroside A, rhaponticin, piceid, astringin, or any combination of these stilbenes or stilbene glycosides.

In some embodiments, the flavonoid is a compound of structure (III) and in other embodiments the flavonoid is a compound of structure (IV). In some other embodiments, at least one of $R_1$—$R_{12}$, such as $R_{10}$ is prenyl. In other embodiments, polyflavonoids are provided and at least one of $R_1$—$R_{12}$ in the compounds of structure (III) or (IV) is a bond to compounds of structure (III) or (IV) (i.e., the compound comprises more than one flavonoid of structure (III) and/or (IV)).

In some other embodiments of the compounds of structure (III) or (IV), $R_1$—$R_{12}$ is H, hydroxyl, a prenyl group or cycloalkyl. For example, in some embodiments the cycloalkyl is substituted and/or comprises one or more carbon-carbon double bonds (i.e., is unsaturated). The optional substitutents are typically selected from aryl, such as phenyl, and aryl carbonyl. Accordingly, in some further embodiments, the flavonoid has one of the following structures (IIIa) or (IVa):

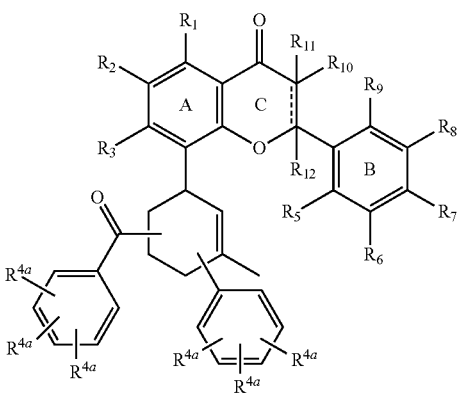

or

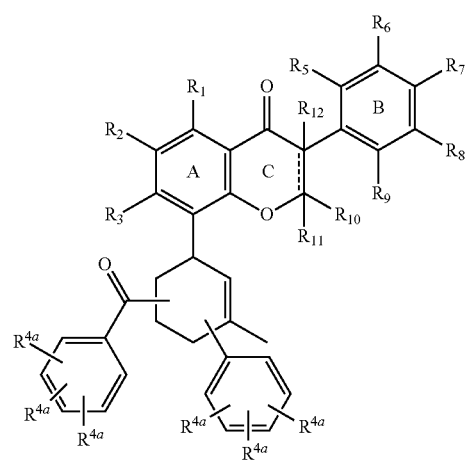

wherein $R^{4a}$ is, at each occurrence, independently H, hydroxyl or a prenyl group.

In certain embodiments of the compounds of structure (IIIa) or (IVa), $R_1$—$R_3$ and $R_5$-$R_{12}$ are each independently selected from H, hydroxyl and a prenyl group. In certain embodiments, at least one of $R_1$—$R_3$, $R_{4a}$ or $R_5$—$R_{12}$ is prenyl, for example in some embodiments, $R_{10}$ is prenyl. In other embodiments of the compounds of structure (IIIa) or (IVa), at least two of $R_1$—$R_3$, $R_{4a}$ or $R_5$—$R_{12}$ is hydroxyl.

In some more specific embodiments, the flavonoid has one of the following structures:

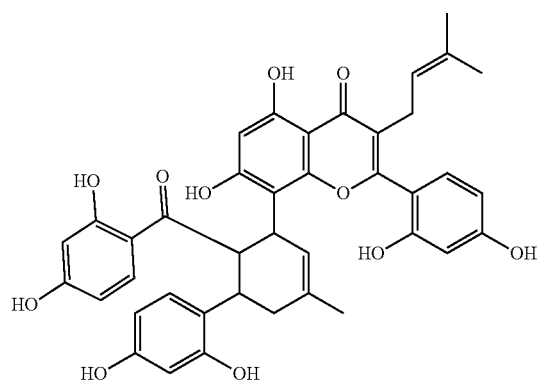

or

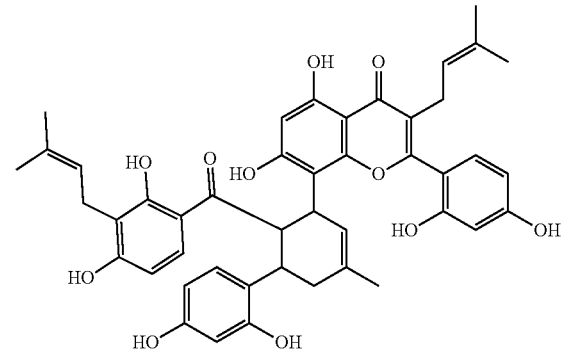

In other embodiments, one of $R_1$—$R_{12}$ joins with another one of $R_1$—$R_{12}$ to form a ring and the remaining $R_1$—$R_{12}$ are H, hydroxyl or a prenyl group. In certain of these embodiments, the ring is a heterocyclic ring, for example a cyclic ether ring. Accordingly, in certain embodiments the flavonoid has one of the following structures (IIIb) or (IVb):

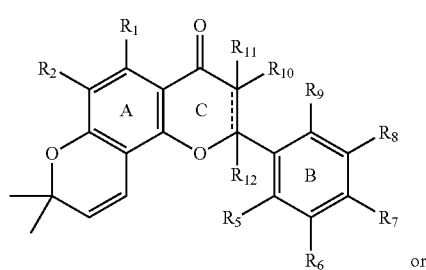

or

IIIb

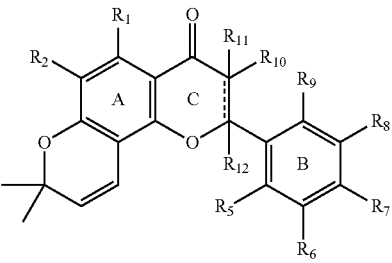

IIIb

In certain embodiments of the compounds of structure (IIIb) or (IVb), $R_1$, $R_2$ and $R_5$—$R_{12}$ are each independently selected from H, hydroxyl and a prenyl group. In certain embodiments, at least one of $R_1$, $R_2$ or $R_5$—$R_{12}$ is prenyl, for example in some embodiments, $R_{10}$ is prenyl. In other embodiments of the compounds of structure (IIIb) or (IVb), at least two of $R_1$, $R_2$ or $R_5$—$R_{12}$ is hydroxyl. In certain embodiments, the flavonoid has the following structure:

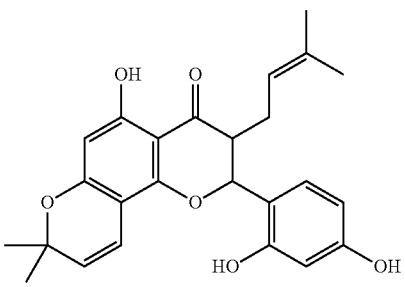 [SMILES: CC(C)=CCC1C(=O)c2c(O)cc3c(c2OC1c1ccc(O)cc1O)C=CC(C)(C)O3]

In various other embodiments, $R_1$—$R_{10}$ of the chalcanoid of structure (V) are each independently selected from H, hydroxyl, a prenyl group, and $C_{1-12}$ alkoxy.

Acacia is a genus of leguminous trees and shrubs. The genus Acacia includes more than 1000 species belonging to the family of Leguminosae and the subfamily of Mimosoideae. Acacias are distributed worldwide in tropical and subtropical areas of Central and South America, Africa, parts of Asia, as well as Australia, which has the largest number of endemic species. Acacias occur primarily in dry and arid regions, where the forests are often in the nature of open thorny shrubs. Acacias are very important economically, providing a source of tannins, gums, timber, fuel and fodder. Tannins, which are isolated primarily from bark, are used extensively for tanning hides and skins. Some Acacia barks are also used for flavoring local spirits. Some indigenous species like A. sinuata also yield saponins, which are used in detergents, foaming agents and emulsifiers. The flowers of some Acacia species are fragrant and used to make perfume. The heartwood of many Acacias is used for making agricultural implements and also provides a source of firewood. Acacia gums find extensive use in medicine and confectionary and as sizing and finishing materials in the textile industry.

The genus of Scutellaria includes approximately 300 species. Scutellaria baicalensis georgi from the Lamiaceae family is said to be one of the potent medicinal herbs and is thus used to treat a number of health disorders for over two thousand years. Scutellaria baicalensis is also called Baical or Chinese Scutellaria, or Scullcap. It is a perennial herb, which grows to a height of 1-4 feet. It has four-angled stems with multiple opposite leaves. Its blue to purple flowers are characterised by the specific shape, which resembles the scull. Two petals of the flower are often called lips. The flowers, blooming in July, are situated on one side of the stem. The root of the herb is thick and branchy. It is almost skinless. The root of Scutellaria baicalensis is used for medicinal purposes. The plant is allowed to grow for about 4 years before the root is taken. The reason is that the amount of beneficial herbal components is higher in the older plants. Roots are harvested in spring or autumn and dried. Chemical composition of the plant includes flavonoids (scutellarin, baicalin, and wogonin), steroidal saponins, alkaloids, glycosides, volatile oils, iridoids and tannins.

Uncaria gambir (Rubiaceae) is a climbing shrub with round branches, which is believed to strengthen teeth when chewed with piper bettle leaves. All parts of the plant have astringent properties. Leaves of the U. gambir plant contain free catechins as well as polymerized catechins—tannins—which are more abundant in younger leaves as compared to older leaves. U. gambir is listed in the Food Additive Database in EAFUS (Everything Added to Food in the United States), in the Korea Food Additives Code by KFDA, and in the Japan Food Additives Code by MHLW as a natural flavoring agent. U. gambir is also listed in the Korea Pharmaceutical Codex (KP), Japan Pharmaceutical Codex (JP) and China Pharmaceutical Codex (CP). In South Korea, there are many over-the-counter (OTC) drugs that contain U. gambir extract, especially for dyspepsia, halitosis, vomiting and anorexia. In Japan, U. gambir is used for diarrhea, vomiting and gastritis. In the United States, U. gambir is used as a dietary supplement to support liver function and fat metabolism.

The biologically active flavans of this disclosure may be obtained by synthetic methods or extracted from one or more plants, such as Acacia, Uncaria, or both. In certain embodiments, an Acacia plant species is selected from A. angustifolia, A. ataxacantha, A. berlandieri, A. bonariensis, A. brevispica, A. catechu, A. chundra, A. concinna, A. floribunda, A. greggii, A. interior, A. macilenta, A. mellifera, A. merrallii, A. occidentalis, A. peninsularis, A. pennata, A. pennatula, A. polyacantha, A. polyphylla, A. riparia, A. roemeriana, A. senegal, A. sinuata, A. tamarindifolia, A. tenuifolia, A. victoriae, A. visco, or any any combination thereof (for exemplary Acacia extracts and flavans, see U.S. Pat. No. 8,124,134). In certain embodiments, an Uncaria plant species is selected from U acida, U. africana, U attenuate, U bernaysii, U. borneensis, U. callophylla, U. cordata, U. elliptica, Uncaria gambir, U. guianensis, U hirsute, U homomalla, U. lanosa, U. longiflora, U. macrophylla, U. orientalis, U. rhynchophylla, U. scandens, U. sessilifructus, U. setiloba, U. sinensis, U. sterrophylla, U. tomentosa, U. wangii, or any any combination thereof (for exemplary Uncaria extracts and flavans, see U.S. Patent Publication No. 2007/0264361).

In further embodiments, a composition of this disclosure comprises an Acacia catechu extract enriched for flavans containing catechin, epicatechin, or a combination thereof. In still further embodiments, a composition of this disclosure comprises an Uncaria gambir extract enriched for flavans containing catechin, epicatechin, or a combination thereof. In yet further embodiments, an Acacia extract enriched for flavans is from Acacia catechu, or an Acacia extract enriched for flavans is a mixture of extracts from one, two, three, four, five or more different Acacia species, Uncaria species, or from other sources. In other embodiments, an Uncaria extract enriched for flavans is from Uncaria gambir, or an Uncaria extract enriched for flavans is a mixture of extracts from one, two, three, four, five or more different Uncaria species, Acacia species, other sources (e.g., different plant such as green tea, synthetic), or any combination thereof. For example, a composition of this disclosure comprises a mixture of an Acacia catechu extract enriched for flavans containing catechin, epicatechin, or both and an Uncaria gambir extract enriched for flavans containing catechin, epicatechin, or both.

In certain embodiments, major active ingredients in an extract of Acacia comprise flavans containing catechin, epicatechin, or both, wherein the extract is enriched for these active ingredients from roots, bark, or a combination thereof. In certain embodiments, major active ingredients in an extract of Uncaria comprise flavans containing catechin, epicatechin, or both, wherein the extract is enriched for these active ingredients from leaves.

In certain embodiments, provided herein are Acacia or Uncaria extracts enriched for one or more flavans containing catechin, epicatechin, or both, wherein the flavans are compounds having a structure of Formula (VI):

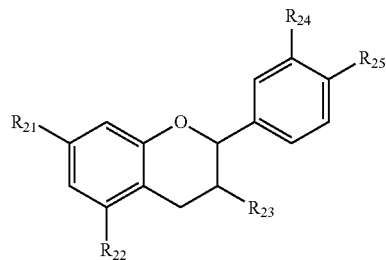

VI wherein $R_{21}$, $R_{22}$, $R_{23}$, $R_{24}$ and $R_{25}$ are independently selected from a H, —OH, —SH, —OCH$_3$, —SCH$_3$, —OR, —SR, —NH$_2$, —NRH, —NR$_2$, —NR$_3^+$X$^-$, esters of substitution groups, independently selected from the group consisting of gallate, acetate, cinnamoyl and hydroxylcinnamoyl esters, trihydroxybenzoyl esters and caffeoyl esters; a carbon, oxygen, nitrogen or sulfur glycoside of a single or a combination of multiple sugars including aldopentose, methyl aldopentose, aldohexose, ketohexose; dimer, trimer or other polymerized flavans;

wherein R is a $C_{1-10}$ alkyl group; and

X is a pharmaceutically acceptable counter anion of hydroxyl, chloride, iodide, sulfate, phosphate, acetate, fluoride, or carbonate.

Curcuma longa L, with common name as turmeric, is a perennial plant of the ginger family, Zingiberaceae. The name of turmeric might come from Latin, terra merita (merited earth) or turmeryte, which is related to saffron. It is originally from tropical south Asia and cultivated extensively in India and Southeast Asia. Turmeric is prepared from the ground rhizome and has been used in India for thousands of years. Besides its culinary usage, modern research has revealed that turmeric has antibacterial, antioxidant, chemopreventive, chemotherapeutic, antiproliferative, antiparasitic, anti-antimalarial, antinociceptive, and anti-inflammatory properties.

In certain embodiments, there are provided herein Curcuma extracts comprising curcuminoids. In further embodiments, a Curcuma longa extract is enriched for curcuminoids, such as curcumin (diferuloylmethane), demethoxycurcumin, bisdemethoxy-curcumin, casumunin A, cassumunin B, or any combination thereof. The biologically active curcuminoids and analogues therof of this disclosure may be obtained by synthetic methods (see Anand et al., *Biochem. Pharmacol.* 76:1590, 2008) or extracted from one or more plants, such as *Curcuma* plants, *Zingiber* plants, or both.

Exemplary species of the *Curcuma* genus of the instant disclosure include *C. aeruginosa, C. albicoma, C. albiflora, C. alismatifolia, C. amada, C. amarissima, C. americana, C. angustifolia, C. aromatica, C. attenuata, C. aurantiaca, C. australasica, C. bakeriana, C. bicolor, C. bhatii, C. brog, C. burttii, C. caesia, C. candida, C. cannanorensis, C. caulina, C. careyana, C. ceratotheca, C. chuanezhu, C. chuanhuangjiang, C. chuanyujin, C. coccinea, C. cochinchinensis, C. codonantha, C. coerulea, C. colorata, C. comosa, C. cordata, C. cordifolia, C. coriacea, C. decipiens, C. domestica, C. ecalcarata, C. ecomata, C. data, C. erubescens, C. euchroma, C. exigua, C. ferruginea, C. flaviflora, C. glans, C. glaucophylla, C. gracillima, C. grahamiana, C. grandiflora, C. haritha, C. harmandii, C. heyneana, C. inodora, C. karnatakensis, C. kuchoor, C. kudagensis, C. künstleri, C. kurzii, C. kwangsiensis, C. lanceolata, C. larsenii, C. latiflora, C. latifolia, C. leucorhiza, C. leucorrhiza, C. loerzingii, C. longa, C. longiflora, C. longispica, C. lutea, C. malabarica, C. mangga, C. meraukensis, C. montana, C. musacea, C. mutabilis, C. neilgherrensis, C.* nilamburensis, *C.* ochrorhiza, *C.* officinalis, *C.* oligantha, *C.* ornata, *C.* pallida, *C.* parviflora, *C.* parvula, *C.* peethapushpa, *C.* petiolata, *C. phaeocaulis, C.* picta—*C.* pierreana, *C.* plicata, *C.* porphyrotaenia, *C.* prakasha, *C.* pseudomontana, *C.* purpurascens, *C.* purpurea, *C.* raktakanta, *C.* ranadei, *C.* reclinata, *C.* rhabdota, *C.* rhomba, *C.* roscoeana, *C.* rotunda, *C.* rubescens, *C.* rubricaulis, *C.* rubrobracteata, *C.* sattayasaii, *C.* sessilis, *C.* sichuanensis, *C.* singularis, *C.* soloensis, *C.* sparganiifolia, *C.* speciosa, *C.* spicata, *C.* stenochila, *C.* strobilifera, *C.* sulcata, *C.* sumatrana, *C.* sylvatica, *C.* sylvestris, *C.* thalakaveriensis, *C.* thorelii, *C.* trichosantha, *C.* vamana, *C.* vellanikkarensis, *C.* viridiflora, *C.* vitellina—*C.* wenchowensis, *C.* wenyujin, *C.* xanthorrhiza, *C.* yunnanensis, *C.* zedoaria, *C.* zedoaroides, *C.* zerumbet.

In certain embodiments, a *Curcuma* extract enriched for curcuminoids is from *Curcuma longa*, or a *Curcuma* extract enriched for curcuminoids is a mixture of extracts from one, two, three, four, five or more different *Curcuma* species or from other sources. For example, a composition comprising curcuminoids may be a a *Curcuma* extract (e.g., *Curcuma longa*) mixed with synthetic curcuminoids, or a mixture of a *Curcuma* extract (e.g., *Curcuma longa*) enriched for curcuminoids with a *Zingiber cassumunar* extract enriched for curcuminoids, *Curcuma phaeocaulis* extract enriched for curcuminoids, *Curcuma. xanthorrhiza* extract enriched for curcuminoids, or any combination thereof. In other embodiments, a *Curcuma* extract enriched for one or more curcuminoids (e.g., curcumin, demethoxy-curcumin, bisdemethoxy-curcumin, casumunin A, cassumunin B, or any combination thereof) may be from root, rhizome, or a combination thereof.

A *Morus* extract enriched for prenylated flavonoids and stilbenes may be used as an anti-inflammatory by inhibiting, for example, both COX and LOX pathways, which can be utilized as is or in combination with at least one bioactive plant extract, such as an extract from *Acacia, Uncaria, Curcuma* or a combination thereof, and optionally contain a pharmaceutically or nutraceutically acceptable active, adjuvant, carrier, diluent, or excipient. In certain embodiments, any of the mentioned compositions can be used to prevent bone loss, increase bone density, prevent, manage or treat osteoporosis in a mammal, such as a human, especially pre-menopausal, menopausal and post-menopausal women.

In certain embodiments, a composition of this disclosure comprises an *Acacia* extract containing or enriched for one or more flavans as described herein (or described in U.S. Pat. No. 8,124,134), and a *Morus* extract containing or enriched for at least one Diels-Alder adduct of a chalcone and a prenylphenyl moiety, prenylated flavonoid, stilbene, or any combination thereof. In certain embodiments, a composition comprises an *Acacia* extract containing or enriched for one or more flavans as described herein or in U.S. Pat. No. 8,124,134 and a *Morus* extract containing or enriched for one or more compounds listed in Table A and Examples 3, 5, 6 and 68. In still further embodiments, a composition comprises an *Acacia* extract containing or enriched for catechin, epicatichin, or both, and a *Morus* extract containing or enriched for one or more prenylated flavonoids, one or more stilbenes, or any combination thereof. In other embodiments, a composition comprises a mixture of a *Morus* extract enriched for one or more prenylated flavonoids and one or more stilbenes, and an *Acacia* extract enriched for flavans.

In further embodiments, a composition of this disclosure comprises a mixture of a *Morus* extract enriched for one or more prenylated flavonoids and one or more stilbenes, and an *Acacia* extract enriched for one or more flavans, wherein the one or more prenylated flavonoids are compounds having a structure of Formula (III) or (IV):

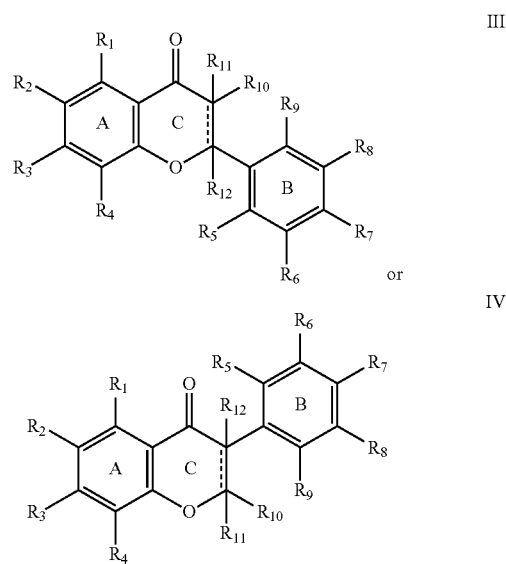

or a pharmaceutically or nutraceutically acceptable salt, tautomer, glycoside, prodrug or stereoisomer thereof, wherein $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, aralkylcarbonyl or a bond to a compound of structure (III) or (IV); or one of $R_1$—$R_{12}$ joins with another one of $R_1$—$R_{12}$ to form a ring, and the remaining $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied;

the chalcanoid is a compound of structure (V):

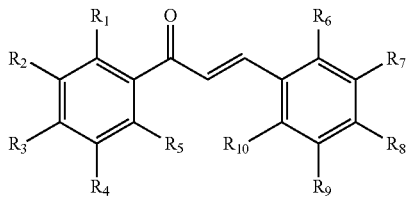

V or a pharmaceutically or nutraceutically acceptable salt, tautomer, glycoside, prodrug or stereoisomer thereof, wherein $R_1$—$R_{10}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, or aralkylcarbonyl, provided that all valencies are satisfied; and the one or more stilbenes are compounds having a structure of Formula (I) or (II):

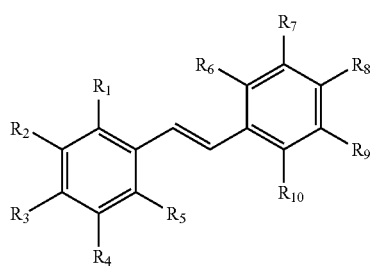

I

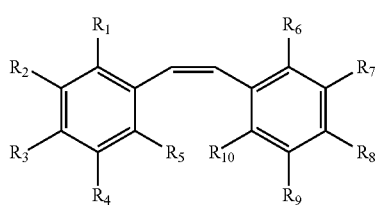

II wherein $R_1$—$R_{10}$ are each independently a H, hydroxyl, glycoside, prenyl, flavonoid, chalcone, halogen, sulfhydryl, amino, aldehyde, $C_{1-12}$ alkyl, $C_{1-12}$ alkenyl, $C_{1-12}$ alkoxy, $C_{1-12}$ alkthio, $C_{1-12}$ alkyamino, aryl, heteroaryl, aralkyl, alkylcarbonyl, or aralkylcarbonyl; and wherein the flavans are compounds having a structure of Formula (VI):

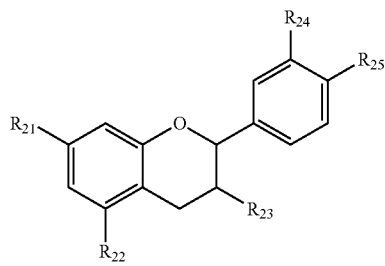

VI wherein $R_{21}$, $R_{22}$, $R_{23}$, $R_{24}$ and $R_{25}$ are independently selected from a H, —OH, —SH, —OCH$_3$, —SCH$_3$, —OR, —SR, —NH$_2$, —NRH, —NR$_2$, —NR$_3^+$X$^-$, esters of substitution groups, independently selected from the group consisting of gallate, acetate, cinnamoyl and hydroxylcinnamoyl esters, trihydroxybenzoyl esters and caffeoyl esters; a carbon, oxygen, nitrogen or sulfur glycoside of a single or a combination of multiple sugars including aldopentose, methyl aldopentose, aldohexose, ketohexose; dimer, trimer or other polymerized flavans;

wherein R is a $C_{1-10}$ alkyl group; and

X is a pharmaceutically acceptable counter anion of hydroxyl, chloride, iodide, sulfate, phosphate, acetate, fluoride, or carbonate.

In any of the mentioned compositions, a *Morus* extract is from *Morus alba*, and an *Acacia* extract is from *Acacia catechu*. In further embodiments of these compositions, a major active ingredient in a *Morus* extract is Albanin G, Kuwanon G, Morusin, oxyresveratrol, mulberroside A or any combination thereof, and a major active ingredient in an *Acacia* extract is catechin, epicatechin, or both.

In further embodiments, any of the mentioned compositions comprise one or more prenylayted flavonoids are compounds having a structure of Formula (III), (IV) or (V), wherein the optional double bond is present in ring C, $R_{11}$ and $R_{12}$ are absent, and $R_{10}$ is a prenyl group. In still further embodiments, any of the mentioned compostions comprise one or more prenylayted flavonoids are compounds having a structure of Formula (III), (IV) or (V), wherein the at least one of $R_1$—$R_9$ is a prenyl group and $R_{10}$—$R_{12}$ are independently H or hydroxyl. In certain embodiments, any of the mentioned compositions comprise one or more stilbenes having a structure of Formula (I) or (II), wherein $R_1$—$R_{10}$ are each independently a H, hydroxyl, glycoside, or $C_{1-4}$ alkoxy. In certain other embodiments, any of the mentioned compostions comprise one or more stilbenes are compounds having a structure of Formula (I) or (II), wherein $R_1$—$R_{10}$ are each independently a H, hydroxyl, glycoside, or $C_{1-4}$ alkoxy. In further embodiments, any of the mentioned compostions comprise one or more stilbenes are compounds having a structure of Formula (I) or (II), wherein $R_1$, $R_5$, $R_6$ and $R_{10}$ are H. In still further embodiments, any of the mentioned compostions comprise one or more stilbenes are compounds having a structure of Formula (I) or (II), wherein $R_2$ is a glucoside, or $R_2$ and $R_8$ are glycosides, and one or more of $R_4$, $R_9$, and $R_{10}$ are hydroxyl. In yet further embodiments, any of the mentioned compostions comprise one or more stilbenes are compounds having a structure of Formula (I) or (II), wherein $R_1$, $R_5$, $R_6$ are H, and one or more of $R_2$—$R_4$ and $R_7$—$R_{10}$ are independently hydroxyl, $C_{1-3}$ alkoxy, or any combination thereof. In certain specific embodiments, a stilbene compound includes oxyresveratrol, resveratrol, piceatannol, pinosylvin, 3,4'-dihydroxystilbene, combretastatin A-1, pterostilbene, rhapontigenin, and a stilbene glycoside includes mulberroside A, rhaponticin, piceid, astringin, or any combination of these stilbenes or stilbene glycosides.

Any of the mentioned *Morus* extract mixed with *Acacia* extract compositions are useful for promoting, managing or improving bone and cartilage health, or for preventing and treating a bone and cartilage disorderor disease (e.g., osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia, or any other bone and cartilage associated indication).

In certain aspects, a composition of this disclosure comprises a mixture of a *Morus* extract enriched for one or more prenylated flavonoids and one or more stilbenes, and an *Acacia* extract enriched for flavans, wherein the composition inhibits cartilage degradation. Cartialge degradation is measured as the level of sulphated GAGs (e.g., released from proteoglycans) released into a medium at the end of a GAG release assay reaction, which reflects the amount of articular cartilage degradation. "Inhibition of cartilage degradation" is established when there is a statistically significant reduction in sulphated GAG release as measured in, for example, a Blyscan™ assay (Accurate Chemical and Scientific Corp., Westbury, New York) and described herein in Example 27.

In certain embodiments, a composition of this disclosure comprises an *Uncaria* extract containing or enriched for one or more flavans as described herein or in U.S. Pat. No. 8,034,387, and a *Morus* extract containing or enriched for at least one Diels-Alder adduct of a chalcone and a prenylphenyl moiety, prenylated flavonoid, stilbene, or any combination thereof. In certain embodiments, a composition comprises an *Uncaria* extract containing or enriched for one or more flavans as described herein or in U.S. Pat. No. 8,034,387 and a *Morus* extract containing or enriched for one or more compounds listed in Table A and Examples 3, 5, 6 and 68. In still further embodiments, a composition comprises an *Acacia* extract containing or enriched for catechin, epicatichin, or both, and a *Morus* extract containing or enriched for one or more prenylated flavonoids, one or more stilbenes, or any combination thereof. In other embodiments, a composition comprises a mixture of a *Morus* extract enriched for prenylated flavonoids, and an *Uncaria* extract enriched for flavans.

In further embodiments, a composition of this disclosure comprises a mixture of a *Morus* extract enriched for one or more prenylated flavonoids and one or more stilbenes, and an *Uncaria* extract enriched for one or more flavans, wherein the one or more prenylated flavonoids are compounds having a structure of Formula (III) or (IV):

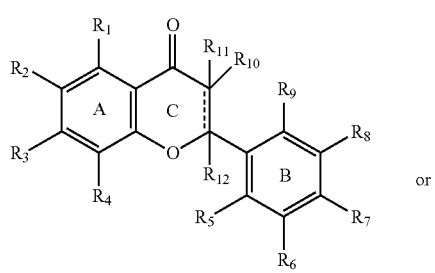

III

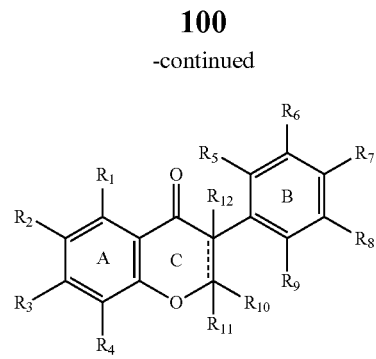

IV or a pharmaceutically or nutraceutically acceptable salt, tautomer, glycoside, prodrug or stereoisomer thereof, wherein $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, aralkylcarbonyl or a bond to a compound of structure (III) or (IV); or one of $R_1$—$R_{12}$ joins with another one of $R_1$—$R_{12}$ to form a ring, and the remaining $R_1$—$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied; the chalcanoid is a compound of structure (V):

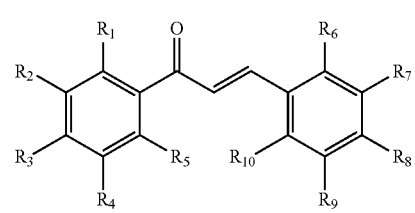

V or a pharmaceutically or nutraceutically acceptable salt, tautomer, glycoside, prodrug or stereoisomer thereof, wherein $R_1$—$R_{10}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, or aralkylcarbonyl, provided that all valencies are satisfied; and the one or more stilbenes are compounds having a structure of Formula (I) or (II):

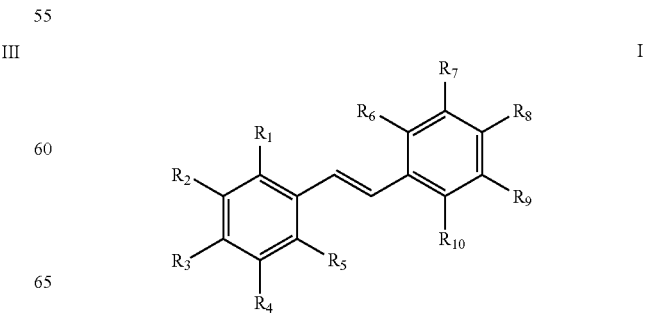

I

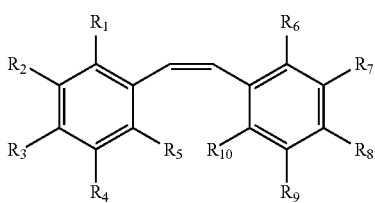

wherein $R_1$—$R_{10}$ are each independently a H, hydroxyl, glycoside, prenyl, flavonoid, chalcone, halogen, sulfhydryl, amino, aldehyde, $C_{1-12}$ alkyl, $C_{1-12}$ alkenyl, $C_{1-12}$ alkoxy, $C_{1-12}$ alkthio, $C_{1-12}$ alkyamino, aryl, heteroaryl, aralkyl, alkylcarbonyl, or aralkylcarbonyl; and wherein the flavans are compounds having a structure of Formula (VI):

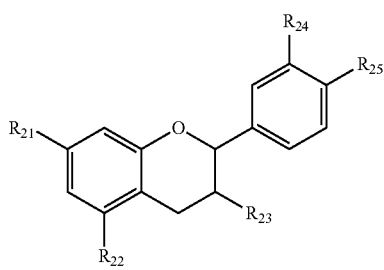

wherein $R_{21}$, $R_{22}$, $R_{23}$, $R_{24}$ and $R_{25}$ are independently selected from a H, —OH, —SH, —OCH$_3$, —SCH$_3$, —OR, —SR, —NH$_2$, —NRH, —NR$_2$, —NR$_3$$^+$X$^-$, esters of substitution groups, independently selected from the group consisting of gallate, acetate, cinnamoyl and hydroxylcinnamoyl esters, trihydroxybenzoyl esters and caffeoyl esters; a carbon, oxygen, nitrogen or sulfur glycoside of a single or a combination of multiple sugars including aldopentose, methyl aldopentose, aldohexose, ketohexose; dimer, trimer or other polymerized flavans;

wherein R is a $C_{1-10}$ alkyl group; and

X is a pharmaceutically acceptable counter anion of hydroxyl, chloride, iodide, sulfate, phosphate, acetate, fluoride, or carbonate.

In any of the mentioned compositions, the *Morus* extract is from *Morus alba*, and the *Uncaria* extract is from *Uncaria gambir*. In further embodiments, a major active ingredient in the *Morus* extract is Albanin G, Kuwanon G, Morusin, oxyresveratrol, mulberroside A or any combination thereof, and a major active ingredient in the *Uncaria* extract is catechin, epicatechin, or a combination thereof.

In further embodiments, the one or more prenylayted flavonoids are compounds having a structure of Formula (III), (IV) or (V), wherein the optional double bond is present in ring C, $R_{11}$ and $R_{12}$ are absent, and $R_{10}$ is a prenyl group. In still further embodiments, the one or more prenylayted flavonoids are compounds having a structure of Formula (III), (IV) or (V), wherein the at least one of $R_1$—$R_9$ is a prenyl group and $R_{10}$—$R_{12}$ are independently H or hydroxyl. In certain specific embodiments, the prenylated flavonoids include Albanin G, Kuwanon G, Morusin, morusinol, Sanggenon, isoxanthoumol, glabridin, cathayanon A, or any combination thereof. In certain embodiments, the one or more stilbenes are compounds having a structure of Formula (I) or (II), wherein $R_1$—$R_{10}$ are each independently a H, hydroxyl, glycoside, or $C_{1-4}$ alkoxy. In further embodiments, the one or more stilbenes are compounds having a structure of Formula (I) or (II), wherein $R_1$, $R_5$, $R_6$ and $R_{10}$ are H. In still further embodiments, the one or more stilbenes are compounds having a structure of Formula (I) or (II), wherein $R_2$ is a glucoside, or $R_2$ and $R_8$ are glycosides, and one or more of $R_4$, $R_9$, and $R_{10}$ are hydroxyl. In yet further embodiments, the one or more stilbenes are compounds having a structure of Formula (I) or (II), wherein $R_1$, $R_5$, $R_6$ are H, and one or more of $R_2$—$R_4$ and $R_7$—$R_{10}$ are independently hydroxyl, $C_{1-3}$ alkoxy, or any combination thereof. In certain specific embodiments, a stilbene compound includes oxyresveratrol, resveratrol, piceatannol, pinosylvin, 3,4'-dihydroxystilbene, combretastatin A-1, pterostilbene, rhapontigenin, and a stilbene glycoside includes mulberroside A, rhaponticin, piceid, astringin, or any combination of these stilbenes or stilbene glycosides.

In some embodiments, the flavonoid is a compound of structure (III) and in other embodiments the flavonoid is a compound of structure (IV). In some othe embodiments, at least one of $R_1$—$R_{12}$, such as $R_{10}$ is prenyl. In other embodiments, polyflavonoids are provided and at least one of $R_1$—$R_{12}$ in the compounds of structure (III) or (IV) is a bond to compounds of structure (III) or (IV) (i.e., the compound comprises more than one flavonoid of structure (III) and/or (IV)).

In some other embodiments of the compounds of structure (III) or (IV), $R_1$—$R_{12}$ is H, hydroxyl, a prenyl group or cycloalkyl. For example, in some embodiments the cycloalkyl is substituted and/or comprises one or more carbon-carbon double bonds (i.e., is unsaturated). The optional substitutents are typically selected from aryl, such as phenyl, and aryl carbonyl. Accordingly, in some further embodiments, the flavonoid has one of the following structures (IIIa) or (IVa):

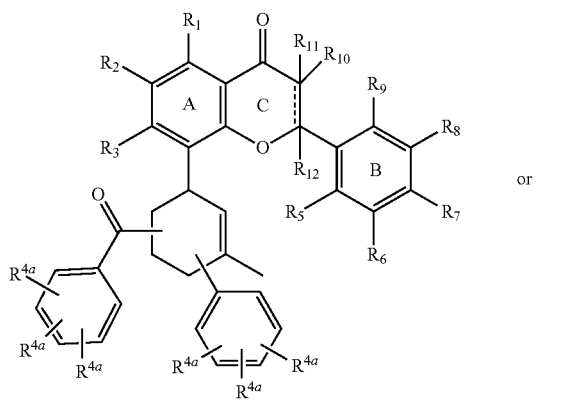

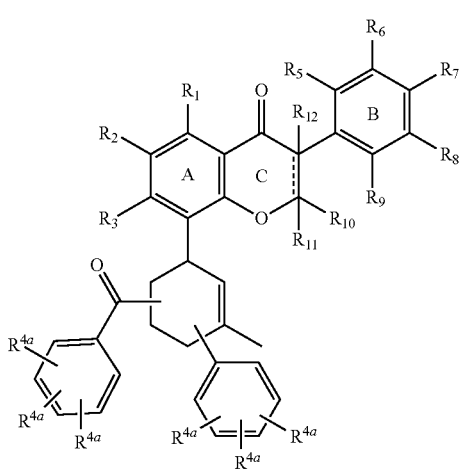

IVa

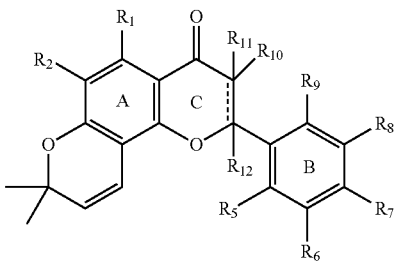

IIIb

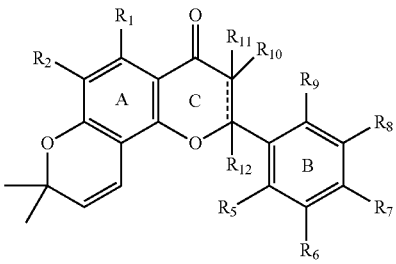

or

IIIb wherein $R^{4a}$ is, at each occurrence, independently H, hydroxyl or a prenyl group.

In certain embodiments of the compounds of structure (IIIa) or (IVa), $R_1$—$R_3$ and $R_5$-$R_{12}$ are each independently selected from H, hydroxyl and a prenyl group. In certain embodiments, at least one one of $R_1$—$R_3$, $R_{4a}$ or $R_5$—$R_{12}$ is prenyl, for example in some embodiments, $R_{10}$ is prenyl. In other embodiments of the compounds of structure (IIIa) or (IVa), at least two of $R_1$—$R_3$, $R_{4a}$ or $R_5$—$R_{12}$ is hydroxyl.

In some more specific embodiments, the flavonoid has one of the following structures:

In certain embodiments of the compounds of structure (IIIb) or (IVb), $R_1$, $R_2$ and $R_5$-$R_{12}$ are each independently selected from H, hydroxyl and a prenyl group. In certain embodiments, at least one one of $R_1$, $R_2$ or $R_5$—$R_{12}$ is prenyl, for example in some embodiments, $R_{10}$ is prenyl. In other embodiments of the compounds of structure (IIIb) or (IVb), at least two of $R_1$, $R_2$ or $R_5$—$R_{12}$ is hydroxyl. In certain embodiments, the flavonoid has the following structure:

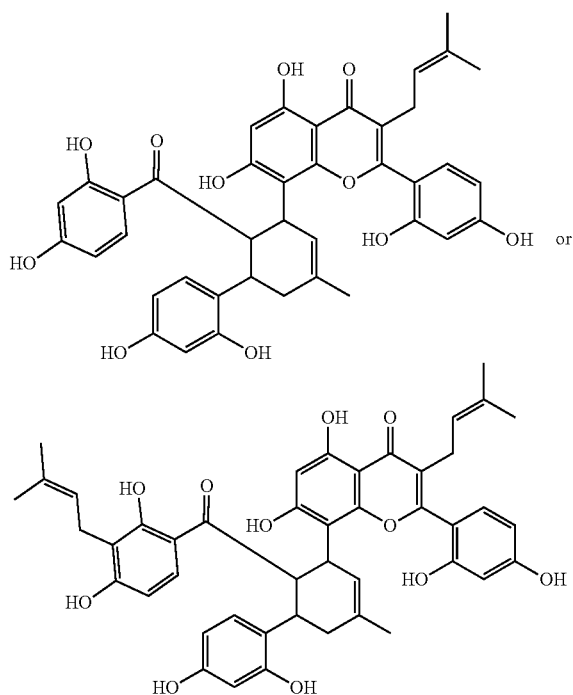

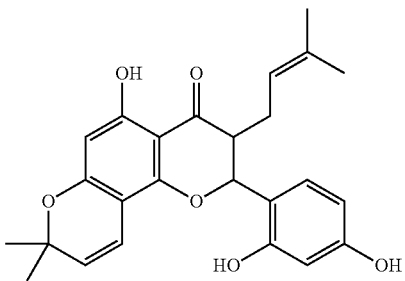 [SMILES: CC(C)=CCC1C(=O)c2c(O)cc3c(c2OC1c1ccc(O)cc1O)C=CC(C)(C)O3]

In other embodiments, one of $R_1$—$R_{12}$ joins with another one of $R_1$—$R_{12}$ to form a ring and the remaining $R_1$—$R_{12}$ are H, hydroxyl or a prenyl group. In certain of these embodiments, the ring is a heterocyclic ring, for example a cyclic ether ring. Accordingly, in certain embodiments the flavonoid has one of the following structures (IIIb) or (IVb):

In various other embodiments, $R_1$—$R_{10}$ of the chalcanoid of structure (V) are each independently selected from H, hydroxyl, a prenyl group, and $C_{1-12}$ alkoxy.

Any of the mentioned Morus extract mixed with Uncaria extract compositions are useful for promoting, managing or improving bone and cartilage health, or for preventing and treating a bone and cartilage disorder or disease (e.g., osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia, or any other bone and cartilage associated indication). In certain embodiments, a composition of this disclosure comprises a mixture of a Morus extract enriched for one or more prenylated flavonoids and one or more stilbenes, and an Uncaria extract enriched for flavans, wherein the composition inhibits bone reabporption and cartilage degradation.

In certain embodiments, a composition comprises a mixture of a Morus extract enriched for prenylated flavonoids, an *Uncaria* extract enriched for flavans, and an *Acacia* extract enriched for flavans. In further embodiments, a composition comprises a mixture of a *Morus* extract enriched for one or more prenylated flavonoids and one or more stilbenes, an *Uncaria* extract enriched for flavans including catechin, epicatechin or both, and an *Acacia* extract enriched for flavans including catechin, epicatechin or both. In certain embodiments, the *Morus* extract is from *Morus alba*, the *Uncaria* extract is from *Uncaria gambir*, and the *Acacia* extract is from *Acacia catechu*. In further embodiments, a major active ingredient in the *Morus* extract is Albanin G, Kuwanon G, Morusin, oxyresveratrol, mulberroside A or any combination thereof, and a major active ingredient in the *Uncaria* and *Acacia* extracts is catechin, epicatechin, or a combination thereof. Any of these three extract compositions (*Morus, Uncaria, Acacia*) are useful for promoting, managing or improving joint health, or for preventing and treating a bone and cartilage disorderor disease (e.g., osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia, or any other bone and cartilage associated indication).

In certain embodiments, a composition of this disclosure comprises a mixture of a *Morus* extract containing or enriched for at least one Diels-Alder adduct of a chalcone and a prenylphenyl moiety, prenylated flavonoid, stilbene or any combination thereof, and a *Curcuma* extract enriched for curcuminoids. In further embodiments, a composition comprises a mixture of a *Morus* extract containing or enriched for one or more compounds listed in Table A and Examples 3, 5, 6 and 68, and a *Curcuma* extract enriched for one or more curcuminoids. In still further embodiments, a composition comprises a *Morus* extract containing or enriched for one or more prenylated flavonoids, one or more stilbenes or any combination thereof, and a *Curcuma* extract enriched for one or more curcuminoids. In certain embodiments, the *Morus* extract is from *Morus alba*, and the *Curcuma* extract is from *Curcuma longa*. In any of the mentioned compositions, a major active ingredient in the *Morus* extract is Albanin G, Kuwanon G, Morusin, oxyresveratrol, mulberroside A or any combination thereof, and a major active ingredient in the *Curcuma* extract is curcumin, demethoxy-curcumin, bisdemethoxy-curcumin or any combination thereof.

Any of the mentioned *Morus* extract mixed with *Curcuma* extract compositions are useful for promoting, managing or improving bone and cartilage health, or for preventing, or treating a bone and cartilage disorderor disease (e.g., osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia, or any other bone and cartilage associated indication). In certain embodiments, a composition of this disclosure comprises a mixture of a *Morus* extract enriched for one or more prenylated flavonoids and one or more stilbenes, and an *Curcuma* extract enriched for one or more curcuminoids, wherein the composition inhibits bone reabsorption and cartilage degradation.

In certain embodiments, a composition comprises a mixture of a *Morus* extract enriched for prenylated flavonoids, an *Acacia* extract enriched for flavans, and a *Curcuma* extract enriched for curcuminoids. In further embodiments, a composition comprises a mixture of a *Morus* extract enriched for one or more prenylated flavonoids and one or more stilbenes, an *Acacia* extract enriched for flavans including catechin, epicatechin or both, and a *Curcuma* extract enriched for one or more curcuminoids. In certain embodiments, the *Morus* extract is from *Morus alba*, the *Acacia* extract is from *Acacia catechu*, and the *Curcuma* extract is from *Curcuma longa*. In further embodiments, a major active ingredient in the *Morus* extract is Albanin G, Kuwanon G, Morusin, oxyresveratrol, mulberroside A or any combination thereof, and a major active ingredient in the *Curcuma* extract is curcumin (diferuloylmethane), demethoxy-curcumin, bisdemethoxy-curcumin or any combination thereof.

In certain embodiments, a composition comprises a mixture of a *Morus* extract enriched for prenylated flavonoids, an *Uncaria* extract enriched for flavans, and a *Curcuma* extract enriched for curcuminoids. In further embodiments, a composition comprises a mixture of a *Morus* extract enriched for one or more prenylated flavonoids and one or more stilbenes, an *Uncaria* extract enriched for flavans including catechin, epicatechin or both, and a *Curcuma* extract enriched for one or more curcuminoids. In certain embodiments, the *Morus* extract is from *Morus alba*, the *Uncaria* extract is from *Uncaria gambir*, and the *Curcuma* extract is from *Curcuma longa*.

Any of these three extract compositions (*Morus, Morus, Acacia, Curcuma* or *Morus, Uncaria, Curcuma*) are useful for promoting, managing or improving bone health, cartilage health or both, or for preventing or for treating a bone disorder, a cartilage disorder or both (e.g., osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia, or any other bone or cartilage associated indication).

In any of the mentioned compositions, a *Morus* extract is enriched for prenylated flavonoids, such as Albanin G, Kuwanon G, Morusin, or any combination thereof. In certain embodiments, a *Morus* extract is enriched for stilbenes, such as oxyresveratrol, mulberroside A, or any combination thereof. In further embodiments, a *Morus* extract is enriched for prenylated flavonoids and stilbenes, including Albanin G, Kuwanon G, Morusin, oxyresveratrol, mulberroside A, or any combination thereof. In still further embodiments, a *Morus* extract is enriched for prenylated flavonoids and stilbenes, wherein the extract comprises from about 2% to about 25% prenylated flavonoids and from about 1% to about 8% stilbenes, or wherein the extract comprises at least 3% prenylated flavonoids and at least 3% stilbenes (weight to weight). In other embodiments, prenylated flavonoids, stilbenes, or both are isolated or purified from a *Morus* extract and used in the compositions of this disclosure. Exemplary active ingredients that can be isolated or purified from a *Morus* extract and used in the compositions of this disclosure include Albanin G, Kuwanon G, Morusin, oxyresveratrol, mulberroside A, or any combination thereof. In any of the mentioned compositions, the *Morus* extract is from *Morus alba*.

In any of the mentioned embodiments, the compositions comprising mixtures of extracts or compounds may be mixed at a particular ratio by weight. For example, a *Morus* extract and an *Acacia* extract may be blended in a 2:1 weight ratio, respectivley. In certain embodiments, the ratio (by weight) of two extracts or compounds of this disclosure ranges from about 0.5:5 to about 5:0.5. Similar ranges apply when more than two extracts or compounds (e.g., three, four, five) are used. Exemplary ratios include 0.5:1, 0.5:2, 0.5:3, 0.5:4, 0.5:5, 1:1, 1:2, 1:3, 1:4, 1:5, 2:1, 2:2, 2:3, 2:4, 2:5, 3:1, 3:2, 3:3, 3:4, 3:5, 4:1, 4:2, 4:3, 4:4, 4:5, 5:1, 5:2, 5:3, 5:4, 5:5, 1:0.5, 2:0.5, 3:0.5, 4:0.5, or 5:0.5. In certain embodiments, *Morus* and *Acacia* extracts are blended in a 1:1, 2:1, 3:1, 4:1, 5:1, 1:2, 1:3, 1:4, or 1:5 weight ratio, respectively. In further embodiments, *Morus* and *Acacia* extracts are blended in a range of 1:2 to 4:1 weight ratio, respectively. In certain embodiments, *Morus* and *Uncaria* extracts are blended in a 1:1, 2:1, 3:1, 4:1, 5:1, 1:2, 1:3, 1:4, or 1:5 weight ratio, respectively. In further embodiments, *Morus* and *Uncaria* extracts are blended in a range of 1:4 to 4:1 weight ratio, respectively. In certain embodiments, *Morus* and *Curcuma* extracts are blended in a 1:1, 2:1, 3:1, 4:1, 5:1, 1:2, 1:3, 1:4, or 1:5 weight ratio, respectively. In further embodiments, *Morus* and *Curcuma* extracts are blended in a range of 1:1 to 4:1 weight ratio, respectively.

In any of the mentioned embodiments, the compositions comprising mixtures of extracts or compounds may be present at certain percentage levels or ratios. In certain embodiments, a composition comprising a *Morus* extract can include 0.1% to 49.9% or about 1% to about 10% or about 0.5% to about 3% of prenylated flavonoids, 0.1% to 49.9% or about 1% to about 10% or about 0.5% to about 3% of stilbenes, or a combination thereof. In certain embodiments, a composition comprising an *Acacia* extract can include from about 0.01% to about 99.9% flavans or include at least 1%, 2%, 3%, 4%, 5%, 6%, 7%, 8%, 9%, 10%, 11%, 12%, 13%, 14%, 15%, 16%, 17%, 18%, 19%, 20%, 30%, 35%, 40%, 45%, 50%, 55%, 60%, 65%, 70%, 75%, or 80% flavans (e.g., catechin, epicatechin, or both)

In certain examples, a composition of this disclosure may be formulated to further comprise a pharmaceutically or nutraceutically acceptable carrier, diluent, or excipient, wherein the pharmaceutical or nutraceutical formulation comprises from about 0.5 weight percent (wt %) to about 90 wt % of active or major active ingredients of an extract mixture. In further embodiments, the pharmaceutical or nutraceutical formulation comprises from about 0.5 weight percent (wt %) to about 90 wt %, about 0.5 wt % to about 80 wt %, about 0.5 wt % to about 75 wt %, about 0.5 wt % to about 70 wt %, about 0.5 wt % to about 50 wt %, about 1.0 wt % to about 40 wt %, about 1.0 wt % to about 20 wt %, about 1.0 wt % to about 10 wt %, about 3.0 wt % to about 9.0 wt %, about 5.0 wt % to about 10 wt %, about 3.0 wt % to about 6 wt % of the major active ingredients in an extract mixture, or the like. In any of the mentioned formulations, a composition of this disclosure is formulated as a tablet, hard capsule, softgel capsule, powder, or granule.

In certain embodiments, a composition comprising a *Morus* extract with a pharmaceutically or nutraceutically acceptable carrier, diluent, or excipient will contain at least 6 wt % or at least 5 wt % or at least 3 wt % or at least 2 wt % or at least 1 wt % active *Morus* ingredients, such as prenylated flavonoids, stilbenes, or a combination thereof. For example, a pharmaceutical or nutraceutical composition comprising a *Morus* extract will include at least 3 wt % prenylated flavonoids or from about at least 0.5 wt % to about at least 2.5 wt % or from about at least 1 wt % to about at least 2.5 wt % or from about at least 1.5 wt % to about at least 2.5 wt % (e.g., Albanin G, Kuwanon G, Morusin, or any combination thereof) and at least 3% stilbenes (e.g., oxyresveratrol, mulberroside A, or both). In certain embodiments, a composition comprising an *Acacia* or *Uncaria* extract with a pharmaceutically or nutraceutically acceptable carrier, diluent, or excipient will contain at least 20 wt % active *Acacia* or *Uncaria* ingredients, such as flavans. For example, a pharmaceutical or nutraceutical composition comprising an *Acacia* or *Uncaria* extract will include at least about 3.5 wt % to about at least 14 wt % or at least about 6 wt % to about at least 16.5 wt % (e.g., catechin, epicatechin, or both). In certain embodiments, a composition comprising a *Curcuma* extract with a pharmaceutically or nutraceutically acceptable carrier, diluent, or excipient will contain at least 25 wt % active *Curcuma* ingredients, such as cucuminoids. For example, a pharmaceutical or nutraceutical composition comprising a *Curcuma* extract will include at least about 4.5 wt % to at least about 13 wt % curcuminoids (e.g., curcumin, demethoxy-curcumin, bisdemethoxy-curcumin, or any combination thereof). In any of the mentioned formulations, a composition of this disclosure is formulated as a tablet, hard capsule, softgel capsule, powder, or granule.

In certain embodiments, a composition of this disclosure comprises *Morus* and *Acacia* extracts, wherein the composition comprises from about 1 wt % to about 2.5 wt % prenylated flavonoids including Albanin G, Kuwanon G and Morusin, from about 1 wt % to about 2.5 wt % stilbenes including oxyresveratrol and mulberroside A, and about 3.5 wt % to about 14 wt % flavans including catechin and epicatechin. In certain other embodiments, a composition of this disclosure comprises *Morus* and *Uncaria* extracts, wherein the compostion comprises from about 0.5 wt % to about 2.5 wt % prenylated flavonoids including Albanin G, Kuwanon G and Morusin, from about 0.5 wt % to about 2.5 wt % stilbenes including oxyresveratrol and mulberroside A, and about 6 wt % to about 16.5 wt % flavans including catechin and epicatechin. In certain further embodiments, a composition of this disclosure comprises *Morus* and *Curcuma* extracts, wherein the compostion comprises from about 1.5 wt % to about 2.5 wt % prenylated flavonoids including Albanin G, Kuwanon G and Morusin, from about 1.5 wt % to about 2.5 wt % stilbenes including oxyresveratrol and mulberroside A, and about 4.5 wt % to about 13 wt % curcuminoids including curcumin.

Any of these compositions may be used to promote joint health; improve joint health; maintain joint health; treat or manage joint health; support joint health; support a normal and comfortable range of motion and/or flexibility; improve range of motion and/or flexibility; reduce the action of harmful enzymes that break down protective joint tissues; alter the action of enzymes that affect joint health; improve joint movement and/or joint function; improve physical mobility; manage and/or maintain physical mobility; alleviate joint pain and/or joint stiffness; improve joint physical function; promote or enhance flexibility and comfortable movement; promote healthy joint function and joint comfort; relieve joint discomfort; relieve joint discomfort caused by exercise, work, overexertion or any combination thereof; promote healthy joints by protecting cartilage integrity; maintain joint cartilage; support joint cartilage; treat, prevent, or manage cartilage degradation; minimize cartilage degradation; promote joint health or comfort by maintaining synovial fluid for joint lubrication; support joint stability and joint flexibility; revitalize joints and promote mobility; promote flexible joints and strong cartilage; maintain steady blood flow to joints to support enhanced flexibility and/or strength; promote joint comfort and a wide range of motion after exercise, work, overexertion, or any combination thereof.

In other embodiments, any of these compositions may be useful for promoting, managing or improving bone health, cartilage health or both, or for preventing or treating a bone disorder, a cartilage disorder (e.g., osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia, or any other bone and cartilage associated indication).

In other embodiments of the present disclosure, a composition can also include an adjuvant or a carrier. Adjuvants include substances that generally enhance the function of the formula in promoting, maintaining, or improving joint health. Suitable adjuvants include Freund's adjuvant; other bacterial cell wall components; aluminum-based salts; calcium-based salts; magnesium, zinc, silica; boron, histidine, glucosamine sulfates, Chondroitin sulfate, copper gluconate, polynucleotides; vitamin D, vitamin K, toxoids; shark and bovine cartilage; serum proteins; viral coat proteins; other bacterial-derived preparations; γ-interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers include compounds that increase the half-life of a therapeutic or neutraceutical composition in a treated subject. Suitable carriers include polymeric controlled release formulations, biodegradable implants, liposomes, bacteria, viruses, oils, esters, or glycols.

Additional adjunctive agents useful with the compositions of this dislclosure include glucosamine (including glucosamine sulfate, glucosamine hydrochloride, N-acetylglucosamine), glycosaminoglycans (GAGs), hyaluronic acid (HA), elastin, ollagen, chicken collagen Type II, hyaluronic acid and collagen blend, chondroitin sulfate, methyl sulfonylmethane (MSM), bovine cartilage, amino acids (including desmosine, isodesmosine, L-glutamine), *Boswellia serrata* extract, piperine (e.g., *Piper nigrum* L (black pepper) extract or *Piper longum* L (long pepper) extract), bromelain (pineapple extract), trypsin, rutin, emu oil, transforming growth factor(TGF)-β, carotenoids (such as lutein, carotene, canthaxanthin); vitamins (such as Vitamin D3), ω-3 fatty acids (such as eicosapentaenoic acid, EPA; docosahexaenoic acid, DHA), calcium fructoborate, eggshell membrane, astaxanthin, *Hydrilla verticillata* extract (leaf and bud), ginger extract (root), grapefruit extract (seed), non-steroidal anti-inflammatory drugs (NSAIDs), or any combination thereof.

Exemplary NSAIDS include salicylates, such as aspirin (acetylsalicylic acid), diflusinal, salsalate; propionic acid derivatives, such as ibuprofen, dexibuprofen, naproxen, fenoprofen, ketoprofen, dexketoprofen, flurbiprofen, oxprozin, loxoprofen; acetic acid derivatives, such as indometacin, tolmetin, sulindac, etodolac, ketorolac, diclofenac, nabumetone; enolic acid derivatives, such as piroxicam, meloxicam, tenoxicam, droxicam, lornoxicam, isoxicam; fenamic acid derivatives, such as mefenamic acid, meclofenamic acid, flufenamic acid, tolfenamic acid; selective COX-2 inhibitors, such s celecoxib, parecoxib, lumiracoxib, etoricoxib, firocoxib, paracetamol, H-harpagide; suphonanilides, such as nimesulide; nicotinic acid derivatives, such as lysine clonixinate; dual COX/LX inhibitors, such as licofelone. A related drug, paracetamol or "acetaminophen" is often considered in the same category as NSAIDS due to its use as a non-narcotic analgesic and fever-reducing agent, but is not classified as a NSAID because it only exerts weak anti-inflammatory activity.

In certain embodiments, compositions of the instant dislcosure further comprise an injectable anticoagulant, an oral anticoagulant, an antiplatelet agent, an anti-angina agent, or a COX-2 selective inhibitor. Examplary injectable anticoagulants include heparin, dalteparin, enoxaparin and tinzaparin. Examples of oral anticoagulants include, but are not limited to warfarin, vitamin K antagonists and vitamin K reductase inhibitors. Examples of antiplatelet agents include aspirin, clodipogrel and dipyridamole. Examplary anti-angina drugs include nitrates, beta-blockers, calcium blockers, angiotensin-converting enzyme inhibitors, and potassium channel activators. Finally, examples of COX-2 selective inhibitors include rofecoxib, celecoxib, etodolac and meloxicam.

In certain embodiments, a composition comprises a mixture of a *Morus* extract enriched for one or more prenylated flavonoids and one or more stilbenes, an *Acacia* extract enriched for flavans, and a glucosamine-type compound. In further embodiments, the *Morus* extract is a *Morus alba* extract, the *Acacia* extract is an *Acacia catechu* extract, and the glucosamine-type compound is glucosamine sulfate, glucosamine hydrochloride, N-acetylglucosamine, chondroitin sulfate, methylsulfonylmethane, and/or hyaluronic acid. In certain embodiments, *Morus* extract, *Acacia* extract, and NAG are blended in a 1:1:1, 2:1:1, 3:1:1, 4:1:1, 5:1:1, 1:2:1, 1:3:1, 1:4:1, 1:5:1, 1:1:2, 1:1:3, 1:1:4, or 1:1:5 weight ratio, respectively. In certain embodiments, *Morus* extract, *Uncaria* extract, and NAG are blended in a 1:1:1, 2:1:1, 3:1:1, 4:1:1, 5:1:1, 1:2:1, 1:3:1, 1:4:1, 1:5:1, 1:1:2, 1:1:3, 1:1:4, or 1:1:5 weight ratio, respectively. In certain embodiments, *Morus* extract, *Curcuma* extract, and NAG are blended in a 1:1:1, 2:1:1, 3:1:1, 4:1:1, 5:1:1, 1:2:1, 1:3:1, 1:4:1, 1:5:1, 1:1:2, 1:1:3, 1:1:4, or 1:1:5 weight ratio, respectively. In certain embodiments, a composition comprises a mixture of a*Morus* extract enriched for prenylated flavonoids, an *Uncaria* extract enriched for flavans, and a glucosamine-type compound. In further embodiments, the *Morus* extract is a *Morus alba* extract, the *Uncaria* extract is an *Uncaria gambir* extract, and the glucosamine-type compound is glucosamine sulfate, glucosamine hydrochloride, N-acetylglucosamine, chondroitin sulfate, methyl sulfonylmethane, or hyaluronic acid.

In certain embodiments, a composition comprises a mixture of a *Morus* extract enriched for prenylated flavonoids, a *Curcuma* extract enriched for curcuminoids, and a glucosamine-type compound. In further embodiments, the *Morus* extract is a *Morus alba* extract, the *Curcuma* extract is a *Curcuma longa* extract, and the glucosamine-type compound is glucosamine sulfate, glucosamine hydrochloride, N-acetylglucosamine, chondroitin sulfate, methylsulfonylmethane, or hyaluronic acid.

In any of the mentioned compositions, the compositions may additionally comprise *Mentha* extract enriched for rosmarinic acid, eriocitrin, or both. Rosmarinic acid accumulation is found most notably in many plants of the Lamiaceae family (dicotyledons), especially in the subfamily Nepetoideae, including plants commonly used as culinary herbs, such as *Ocimum basilicum* (basil), *Ocimum tenuiflorumcum* (holy basil), *Melissa officinalis* (lemon balm), *Rosmarinus officinalis* (rosemary), *Origanum majorana* (marjoram), *Salvia officinalis* (sage), *Thymus vulgaris* (thyme) and *Mentha piperita* (peppermint). Rosmarinic acid is also found in plants with medicinal properties, such as common self-heal (*Prunella vulgaris*) or species in the genus *Stachy*. Other exemplary plants that contain rosmarinic acid include *Heliotropium foertherianum* (a plant in the family Boraginaceae), species in the genera *Maranta* (*Maranta leuconeura, Maranta depressa*, which are plants in the family *Marantaceae*, monocotyledons), species in the genera *Thalia* (*Thalia geniculata*), and *Anthoceros agrestis* (hornwort).

Exemplary mint plants containing rosmarinic acid or eriocitrin or both include *Mentha aquatica* (Water mint or Marsh mint); *Mentha arvensis* (Corn Mint, Wild Mint, Japanese Peppermint, Field Mint, Pudina, Banana mint); *Mentha asiatica* (Asian Mint); *Mentha australis* (Australian mint); *Mentha canadensis*; *Mentha cervina* (Hart's Pennyroyal); *Mentha citrata* (Bergamot mint, Orange mint); *Mentha crispata* (Wrinkled-leaf mint); *Mentha dahurica* (Dahurian Thyme); *Mentha diemenica* (Slender mint); *Mentha laxiflora* (Forest mint); *Mentha longifolia* (*Mentha sylvestris*, Horse Mint); *Mentha piperita* (Peppermint); *Mentha pulegium* (Pennyroyal); *Mentha requienii* (Corsican mint); *Mentha sachalinensis* (Garden mint); *Mentha satureioides* (Native Pennyroyal); *Mentha spicata* (*M. viridis*, syn M. cordifolia Spearmint, Curly mint); *Mentha suaveolens* (Apple mint, Pineapple mint (a variegated cultivar of Apple mint)); *Mentha vagans* (Gray mint).

In certain embodiments, a composition comprises a mixture of a *Morus* extract enriched for prenylated flavonoids, an *Acacia* extract enriched for flavans, and a *Mentha* extract enriched for rosmarinic acid, eriocitrin, or both. In further embodiments, the *Morus* extract is a *Morus alba* extract, the *Acacia* extract is an *Acacia catechu* extract, and the *Mentha* extract is a *Mentha piperita* extract. In certain embodiments, *Morus*, *Acacia* and *Mentha* extracts are blended in a 1:1:0.5, 2:1:0.5, 3:1:0.5, 4:1:0.5, 5:1:0.5, 1:2:0.5, 1:3:0.5, 1:4:0.5, 1:5:0.5, 1:1:1, 1:1:2, 1:1:3, 1:1:4, or 1:1:5 weight ratio, respectively. In certain embodiments, a composition comprises a mixture of a *Morus* extract enriched for prenylated flavonoids, an *Uncaria* extract enriched for flavans, and a *Mentha* extract enriched for rosmarinic acid, eriocitrin, or both. In further embodiments, the *Morus* extract is a *Morus alba* extract, the *Uncaria* extract is an *Uncaria gambir* extract, and the *Mentha* extract is a *Mentha piperita* extract. In certain embodiments, *Morus*, *Uncaria* and *Mentha* extracts are blended in a 1:1:0.5, 2:1:0.5, 3:1:0.5, 4:1:0.5, 5:1:0.5, 1:2:0.5, 1:3:0.5, 1:4:0.5, 1:5:0.5, 1:1:1, 1:1:2, 1:1:3, 1:1:4, or 1:1:5 weight ratio, respectively.

In certain embodiments, a composition comprises a mixture of a *Morus* extract enriched for prenylated flavonoids, a *Curcuma* extract enriched for curcuminoids, and a *Mentha* extract enriched for rosmarinic acid, eriocitrin, or both. In further embodiments, the *Morus* extract is a *Morus alba* extract, the *Curcuma* extract is a *Curcuma longa* extract, and the *Mentha* extract is a *Mentha piperita* extract. In certain embodiments, *Morus*, *Curcuma* and *Mentha* extracts are blended in a 1:1:0.5, 2:1:0.5, 3:1:0.5, 4:1:0.5, 5:1:0.5, 1:2:0.5, 1:3:0.5, 1:4:0.5, 1:5:0.5, 1:1:1, 1:1:2, 1:1:3, 1:1:4, or 1:1:5 weight ratio, respectively.

Any of the mentioned compositions are useful for promoting bone health, cartilage health or both; improving bone health, cartilage health or both; maintaining bone health, cartilage health or both; treating or managing bone health, cartilage health or both; supporting bone health, cartilage health or both; supporting a normal and comfortable range of motion or flexibility; improving range of motion or flexibility; reducing the action of harmful enzymes that break down protective bone tissue, cartilage tissue or both; altering the action of enzymes that affect bone health, cartilage health or both; improving joint movement or bone function, cartilage function or both; improving physical mobility; managing or maintaining physical mobility; alleviating bone and cartilage pain or joint stiffness; improving physical function of bone or cartilage; promoting or enhancing flexibility and comfortable movement; promoting healthy bone function, cartilage function, joint comfort or any combination thereof; relieving discomfort; relieving discomfort caused by oxidative stress, harmful free radicals, aging, wear and tear, exercise, work, overexertion or any combination thereof; managing or reducing bone damage, cartilage damage or both caused by oxidative stress, harmful free radicals, aging, wear and tear, exercise, work, overexertion or any combination thereof; promoting healthy bone, healthy cartilage or both by protecting bone integrity, cartilage integrity or both; maintaining bone, cartilage or both; supporting bone, supporting cartilage or both; treating, preventing, or managing bone absorption, cartilage degradation or both; minimizing cartilage degradation; promoting bone health, cartilage health, joint comfort, or any combintion thereof by maintaining synovial fluid for joint lubrication; supporting bone stability; revitalizing bone, cartilage or both to promote mobility; promoting flexible joints, strong cartilage or both; maintaining steady blood flow to bone to support enhanced bone strength; promoting comfort and a wide range of motion after exercise, work, overexertion or any combination thereof.

In further embodiments, any of the mentioned compositions are useful for promoting, managing or improving bone health, cartilage health or both, or for preventing, managing or treating a bone disorder, cartilage disorder or both (such as osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia), or any other bone- or cartilage-associated indication, or any combination thereof.

Bone is constantly undergoing a metabolic process called remodeling. This includes a degradation process, bone reabsorption, and a building process, bone formation. Cross-linked telopeptides collagens are the products in the remodeling process. While telopeptide of type I collagen accounts about 90% of the organic matrix of bone, the type II collagen is the major organic constituent of cartilage. Disruption of the structural integrity of cartilage is the major histological finding in osteoarthritis and rheumatoid arthritis. Following the degradation of cartilage, fragments of C-terminal cross-linked telopeptide type II collagen (CTX-II) are being released into circulation and subsequently secreted into urine. Therefore, (CTX-II) is considered a viable biomarker for cartilage degradation and disease progression. In multiple studies, urinary CTX-II has been reported to be useful indicator in progression of osteoarthritis, and early indication of rheumatoid arthritis.

As osteoarthritis progresses, the joint components including matrix and cartilage are degraded by proteases. The degraded products such as CTX-II are released into the serum and urine, and the CTX-II concentration in body fluids reflects OA progression. Levels of CTX-II can be measured by known assays, such as the one described in Example 38 herein.

In certain embodiments, the promotion, management or improvement of bone health, cartilage health or both, or prevention, management or treatment of a bone disorder, cartilage disorder or both (such as osteoporosis, osteoarthritis, osteonecrosis, osteophyte, bone fracture, metabolic bone disorders, osteochondritis diseases, osteochondroma, osteitis deformans, osteitis fibrosa cystica, ostteitis pubis, condensing osteitis, osteogenesis imperfecta, osteomalacia (rickets), osteomyelitis, osteopenia), or any other bone- or cartilage-associated indication, or any combination thereof, is detected by measuring a biomarker, such as CTX-II.

The MIA-induced OA disease model in rats is a standardized model most frequently used to mimic the human OA (Lee et al., 2014). The model involves inoculation of MIA into a femorotibial joint pocket that induces pain responses in the ipsilateral limb accompanied by progressive cartilage degradation. Intra-articular injection of MIA disrupts chondrocyte glycolysis by inhibiting glyceraldehyde-3-phosphatase dehydrogenase and results in chondrocyte death, neovascularization, subchondral bone necrosis and collapse, as well as inflammation (Guzman et al., 2003). These characteristics make the model very attractive to evaluate compounds for their anti-inflammatory, analgesic and/or potential disease modifying activities as it shares similar disease pathology to the human OA. As a result, we selected this mature model to investigate the effect of UP1306 and UP446 alone or in combination in mitigating CTX-II biomarker while managing clinical symptoms such as pain sensitivity and maintaining articular structural integrity after administered orally for 6 weeks.

Coupled with symptoms and biomarkers, histopathological analyses of articular cartilage, synovial membrane, and subchondral bone have been used to evaluate OA disease progression or to measure outcome of therapeutic interventions (Goldring et al., 2000). In the current discovery, significant improvements in maintenance of the articular structural integrity of rats treated with the composition were observed. These effects were demonstrated in the histopathology data as exhibited by limited loss, degeneration, or necrosis of chondrocytes, smoother articular cartilage surface, deeper and uniform stain of intracellular matrix, and close to normal contour of the subchondral bone. For obvious reasons, this minimal cartilage degradation was also supported by the significant reductions in pain sensitivity where the composition achieved unexpected synergistic impact in reducing OA associated pain. The changes in magnitude of inhibition were computed and were found that the composition performed 180.1, 128.0, 114.0, 89.1, 84.9% better than UP1306 and 65.7, 91.5, 85.6, 61.4, 53.2% more than UP446 at week-1, week-2, week-3, week-4 and week-5, respectively. Furthermore, as demonstrated by the urine CTX-II, statistically significant reduction in the level of uCTX-II was also observed for rats treated with the composition. Here, neither UP1306 nor UP446 treated rats reached a significant level of reductions the level of uCTX-II when administered alone. In comparison, the composition resulted in a 20.2% and 27.2% greater reductions in uCTX-II than its constituents UP1306 and UP446, respectively. These findings confirm the assumption that combining these plant extracts together could result an unexpected reduction of biomarker uCTX-II such an improvement had clinical relevance with profound boost to their cartilage sparing activity and hence alleviation of pain.

Substantiating this statement in human clinical studies, urine CTX-II levels were well aligned with cartilage degradation and associated pain in OA patients. For example, urinary CTX-II concentrations were found elevated and associated with knee pain and function in subjects underwent anterior cruciate ligament reconstruction. In these patients, decreased uCTX-II concentrations were correlated with decreased knee pain and improving function providing meaningful prognosis (Chmielewski et al., 2012). Similarly, in a cross sectional evaluation of biochemical markers of bone, cartilage, and synovial tissue metabolism in patients with knee osteoarthritis, uCTX-II were found significantly increased corresponding disease severity and were correlated with changes in joint space narrowing (Garnero et al., 2001).

Considering the multifactorial nature of OA, it has previously been suggested that the ability to slow the progression of articular cartilage degeneration is greater with a combination therapy than that of any single component alone (Lippiello et al., 2000). The composition of bioflavonoid standardized extracts from *Scutellaria baicalensis*, *Acacia catechu*, and *Morus alba* suit very well in this category. In fact, when the merit of formulating these three plant materials was tested, an unexpected synergy in alleviating pain sensitivity was observed from the combination of these three plant materials that exceeded the predicted result based on simply summing the effects observed for each of its constituents. Furthermore, significance of urinary CTX-II level reductions was achieved only for the standardized blend consists of these three extracts. Overall, A) reduction in urine CTX-II level B) articular cartilage protection and C) unexpected significant reductions in pain sensitivity were the fundamental findings of this discovery. Clinical and pre-clinical literature searches failed to produce previous reports of either of the constituents to reduce urine CTX-II levels in OA. This signifies the novelty of the composition in maintaining articular structural integrity as reflected by the reduced uCTX-II level accompanied by minimal pain sensitivity. We believe that these medicinal plants may have complementary effects to each other in reducing biomarker uCTX-II, preventing articular cartilage degradation and mitigating associated pain which could be translated to improved joint mobility and function.

We have evaluated the efficacy of a composition comprised of acacia, scutellaria and morus extracts at the ratio of 0.282:0.308:0.410, respectively, administered orally to MIA-induced osteoarthritis disease model in the rats. Prenylated flavonoids from *M. alba*, free-b-ring flavonoids from *S. baicalensis* and flavans from *A. catechu* have traditionally been used for multiple indications. However, the use of these extracts in a specific combination together for cartilage protection or associated symptoms has never been reported. As a matter of fact, there has not been any report in the literature for any of the disclosed extracts to reduce urine CTX-II. Here, significant reduction in urinary CTX-II, synergistic pain alleviation and maintenance of articular structural integrity were observed as a result of oral treatment of their composition. These findings suggest that the standardized blend of morus, scutellaria and acacia could potentially be considered as an alternative therapy from natural sources for the treatment of OA and its associated symptoms.

EXAMPLES

Example 1

Preparation of Organic and Aqueous Extracts from *Morus alba*

Plant material from *Morus alba* L. root barks was ground to a particle size of no larger than two millimeters (mm). Dried ground plant material (60 grams (g) was then transferred to an Erlenmeyer flask and Methanol:Dichloromethane (1:1 volume ratio) (600 milliliters (mL)) was added. The mixture was shaken for one hour, filtered and the biomass was extracted again with Methanol:Dichloromethane (1:1 volume ratio) (600 mL). These organic extracts were combined and evaporated under vacuum to provide 3.55 g of organic extract (OE). After organic extraction, the biomass was air dried and extracted once with ultrapure water (600 mL). The aqueous solution was filtered and freeze-dried to provide 4.44 g of aqueous extract (AE).

Similar results were obtained using the same procedure or reflex in flasks, but with the organic solvent being replaced with methanol or ethanol to provide a methanol extract (ME) or ethanol extract (EE), respectively. Other species and parts of plants and marine sample were extracted using this same procedure.

Example 2

High Throughput Purification (HTP) of Active Plant Extracts

Organic extract material (400 mg) from the *Morus alba* root bark extract obtained in Example 1 was loaded onto a prepacked (2 cm ID×8.2 cm, 10 g silica gel) column. The column was then eluted using a Hitachi® High Throughput Purification (HTP) system with a gradient mobile phase of (A) 50:50 volume ratio of EtOAc:Hexane and (B) Methanol from 100% A to 100% B in 30 minutes at a flow rate of 5 mL/min. The separation was monitored using a broadband wavelength UV detector and the fractions were collected in a 96-deep-well plate at 1.9 mL/well using a Gilson fraction collector. The sample plate was dried under low vacuum and centrifugation and then the samples were dissolved with 1.5 mL dimethyl sulfoxide (DMSO) per well. A portion (100 μL) was taken and combined (based on UV trace) for the function assay. Column fractions having significant biological activity were retained for further testing.

Example 3

Isolation, Purification, and Identification of Prenylated Flavonoids from *Morus alba* Extracts An organic extract (11 g) from the root barks of *Morus alba*, obtained as described in Example 1, was divided and loaded separately onto two pre-packed flash columns (120 g silica, particle size 32-60 μm, 4 cm×19 cm), and then eluted with Hexane, EtOAc and Methanol (as the mobile phase) at a flow rate of 20 mL/minutes. The gradients started with 95% Hexane/EtOAC for 5 minutes, then increased EtOAC from 5% to 100% over the duration of 25 minutes, and then held at 100% EtOAc for additional five minutes, before increasing MeOH from 0% to 50% MeOH/EtOAC over a next period of 15 minutes, finally changed the elution solution to 100% MeOH and eluted the column for another 16 minutes. The total run time was 66 minutes and 88 fractions were generated for each column. The fractions were analyzed by silica gel thin layer chromatography (TLC) and pooled together to generate eight column eluent pools.

The resulting best active pool (containing 300 mg of material) was fractionated on a preparative C18 column (30 cm×250 cm) with a gradient mobile phase of water (A) and methanol (B) over 60 minutes at a flow rate of 20 mL/minute to generate 22 fraction pools. Mass Spectrometry (MS) analysis showed that these pooled fractions of material contain three related compounds, described in more detail below.

Compound 1 (28.2 mg) was identified as a Diels-Alder adduct of a chalcone and prenylphenyl moiety called Kuwanon G, also known as Moracenin B or Albanin F, by High Resolution Electron Spray Ionization Mass Spectroscopy (HRESIMS) (m/z) [M+H]⁻=693.2329; UV $\lambda_{max}$ (MeOH): 265, 320 nm; $^1$H NMR (600 MHz, DMSO-d$_6$, 100° C.) δ ppm 1.44 (s, 3H) 1.52 (br. s., 3H) 1.58 (s, 3H) 1.92 (m, 2H) 3.08 (d, 3H) 3.56 (m, 2H) 4.29 (d, J=10.02 Hz, 1H) 4.48 (m, 1H) 5.07 (m, 1H) 5.14 (br. s, 1H) 5.93 (s, 2H) 5.96 (dd, J=8.35, 2.23 Hz, 1H) 6.02 (br s, 1H) 6.11 (d, J=2.23 Hz, 1H) 6.41 (dd, J=8.35, 2.23 Hz, 1H) 6.51 (s, 1H) 6.60 (m, 1H) 7.13 (d, J=8.35 Hz, 1H) 7.28 (br s, 1H); $^{13}$C NMR (126 MHz, METHANOL-d$_4$) δ ppm 16.35 (1 C) 21.78 (1 C) 23.35 (1 C) 24.53 (1 C) 37.72 (1 C) 97.14 (1 C) 101.57(1 C) 102.22(1 C) 102.33(1 C) 104.28(1 C) 106.55 (2C) 107.00(1 C) 107.21 (1 C) 112.37(1 C) 114.47(1 C) 120.27(1 C) 121.62(2 C) 123.27(1 C) 131.05(1 C) 131.35 (2 C) 132.62 (1 C) 132.99 (1 C) 155.16 (1 C) 155.56 (1 C) 156.38 (1 C) 159.66 (1 C) 160.39 (2 C) 161.13 (1 C) 161.88 (1 C) 164.51 (1 C) 164.63 (1 C) 182.46 (1 C) 208.68 (1 C).

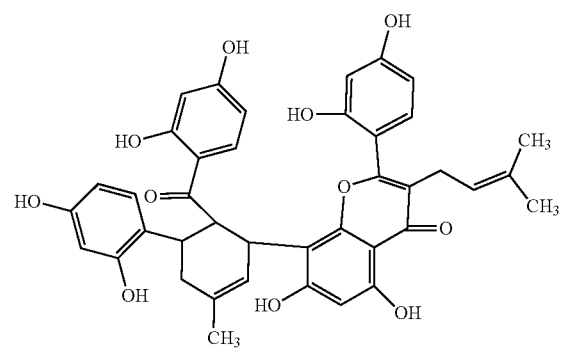

Kuwanon G

Compound 2 (10.5 mg) was identified as Albanin G, also known as Kuwanon H or Moracenin A, another Diels-Alder adduct of a chalcone and prenylphenyl moiety by HRESIMS (m/z) [M−H]⁻=759; UV $\lambda_{max}$ (MeOH): 265, 320 nm; $^{13}$C NMR (126 MHz, METHANOL-d$_4$) δ ppm 16.35 (1 C) 16.47 (1 C) 20.96 (1 C) 21.79 (1 C) 23.32 (1 C) 24.51 (1 C) 24.53 (1 C) 33.74 (1 C) 35.61 (1 C) 36.81 (1 C) 37.77 (1 C) 97.19 (1 C) 102.27 (1 C) 102.33(1 C) 104.24(1 C) 106.07(1 C) 106.53 (2 C) 107.34(1 C) 112.37(1 C) 113.94(1 C) 114.35 (1 C) 120.17(1 C) 121.60(2 C) 122.31 (2 C) 123.25(1 C) 130.21 (2C) 131.33 (2 C) 132.96 (1 C) 156.37 (3 C) 157.07 (1 C) 159.59 (1 C) 160.37 (1 C) 161.23 (1 C) 161.77 (1 C) 161.96 (1 C) 162.21 (1 C) 182.45 (1 C) 208.82 (1 C).

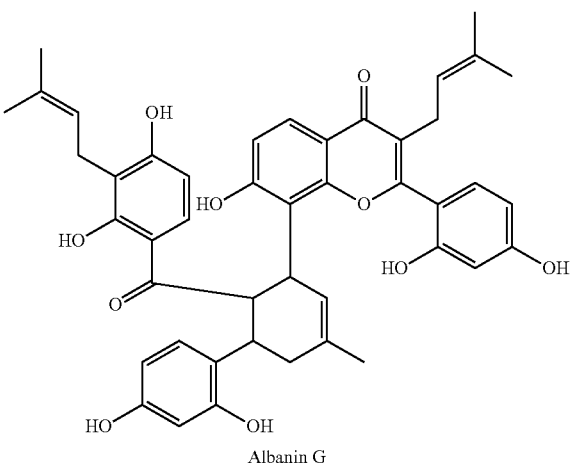 [SMILES: CC(C)=CCc1c(O)ccc(C(=O)C2C(c3c(O)ccc4c(=O)c(CC=C(C)C)c(-c5ccc(O)cc5O)oc34)C=C(C)CC2c2ccc(O)cc2O)c1O]

Albanin G

Compound 3 (12.9 mg) was identified as Morusinol by ESIMS (m/z) [M–H]⁻=437; UV $\lambda_{max}$ (MeOH): 269, 317 nm; ¹H NMR (500 MHz, METHANOL-$d_4$) δ ppm 1.08 (s, 6H) 1.43 (s, 6H) 1.60 (m, 2H) 2.43 (m, 2H) 5.59 (d, J=9.97 Hz, 1H) 6.16 (s, 1H) 6.43 (m, 2H) 6.59 (d, J=10.26 Hz, 1H) 7.15 (d, J=9.09 Hz, 1H); ¹³C NMR (126 MHz, METHANOL-$d_4$) δ ppm 21.52 (t, 1 C) 28.54 (q, 2 C) 28.88 (q, 2 C) 43.19 (t,1 C) 71.56 (s, 1 C) 79.28 (s, 1 C) 100.28 (d, 1 C) 102.35 (s, 1 C) 104.06 (d, 1 C) 106.05 (s, 1 C) 108.26 (d, 1 C) 113.14 (s, 1 C) 115.89 (d, 1 C) 122.99 (s, 1 C) 128.36 (d, 1 C) 132.37 (d, 1 C) 153.97 (s, 1 C) 157.96 (s, 1 C) 160.62 (s, 1 C) 162.13 (s, 1 C) 162.88 (s, 1 C) 163.63 (s, 1 C) 184.09 (s, 1 C).

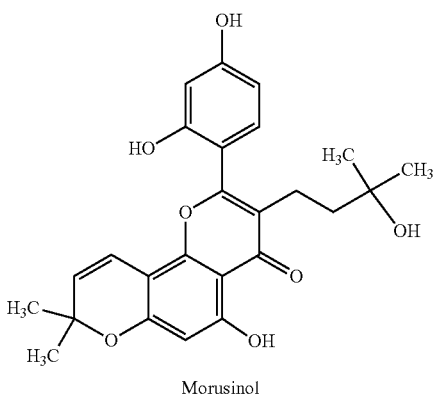 [SMILES: CC(C)(O)CCc1c(-c2ccc(O)cc2O)oc2c3c(cc(O)c2c1=O)OC(C)(C)C=C3]

Morusinol

Another best active pool (containing 538 mg of material) was fractionated on a preparative C18 column (30 cm×250 cm) with a gradient mobile phase of water (A) and methanol (B) over 60 minutes at a flow rate of 20 mL/minute to generate 16 fraction pools. A prenylphenylated Compound 4, called Morusin (80 mg), also known as Mulberrochromene was isolated. The structure and spectroscopy data were as follows: ESIMS (m/z) [M–H]⁻=419; UV max (MeOH): 269.4 nm; 1H NMR (500 MHz, METHANOL-$d_4$) δ ppm 1.41 (m, 9H) 1.58 (s, 3H) 3.10 (d, J=7.15 Hz, 2H) 5.09 (m, 1H) 5.57 (d, J=10.49 Hz, 1H) 6.14 (s, 1H) 6.40 (m, 2H) 6.59 (d, J=10.01 Hz, 1H) 7.10 (d, J=8.11 Hz, 1H); 13C NMR (126 MHz, METHANOL-$d_4$) δ ppm 16.25 (q, 1 C) 23.48 (t, 1 C) 24.42 (q, 1 C) 26.99 (q, 2 C) 77.70 (s, 1 C) 98.69 (d, 1 C) 100.79 (s, 1 C) 102.43 (d, 1 C) 104.51 (s, 1 C) 106.63 (d, 1 C) 111.67 (s, 1 C) 114.35 (d, 1 C) 120.63 (s, 1 C) 121.30 (d, 1 C) 126.73 (d, 1 C) 131.02 (d, 1 C) 131.42 (s, 1 C) 152.36 (s, 1 C) 156.51 (s, 1 C) 159.04 (s, 1 C) 160.61 (s, 1 C) 161.27 (s, 1 C) 162.14 (s, 1 C) 182.44 (s, 1 C).

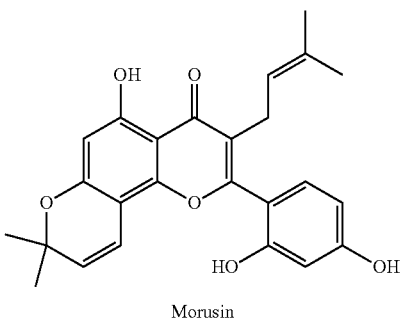 [SMILES: CC(C)=CCc1c(-c2ccc(O)cc2O)oc2c3c(cc(O)c2c1=O)OC(C)(C)C=C3]

Morusin

Example 4

Preparation of Organic 70% EtOH Extracts from *Morus alba*

2 kg of dried *Morus alba* roots and root barks were cut, crushed, and then extracted with approximately ten-fold volume (20 L) of 70% ethyl alcohol in water (v/v); the extraction was carried on at 80° C. for 5 hrs. The ethanol solution was filtered to obtain the supernatant which was then concentrated with an evaporator under vacuum at 40° C. This extraction and concentration procedure was repeated two times. The extraction solutions were then combined together and concentrated until the volume become ¹⁄₂₅ of the original volume. The concentrated solution was dried by vacuum freeze-drying to obtain 283.5 g of *Morus alba* 70% EtOH extract powder 1-01. The extraction yield was about 14.7% (w/w).

Example 5

Isolation of Mulberroside A from *Morus alba* EtOH Extracts

A 20 g amount of *Morus alba* 70% ethyl alcohol extract 1-01 from Example 4 was loaded onto silica gel column and the column was eluted with a stepwise application of solvent mixture containing linear gradient of hexane:EtOAc (5:1 to 1:5) to give eight sub-fractions. Among the eight subfractions, the 8ᵗʰ fraction was subjected to a RP-HPLC column (YMC-ODS) 5 μm, C18 (250×30 mm) by injection onto a preparative HPLC system (JAI, LC-9104, Japan) eluted with 15% Acetonitrile in $H_2O$ in 16.2 min with UV wavelength 330 nm to afford Compound 5 (mulberroside A) (191 mg).

Compound 5 (mulberroside A, $C_{26}H_{32}O_{14}$): APCI-MS (m/z) [M+H]⁺ 569.58; UV $\lambda_{max}$ (MeOH): 217.9, 325.6 nm; ¹H NMR (400 MHz, DMSO-$d_6$) δ ppm 6.34 (brs, 1H) 6.52 (dd, J=8.6, 2.4 Hz, 1H) 6.54 (d, J=2.4 Hz, 1H) 6.57 (s, 1H) 6.64 (s, 1H) 6.94 (d, J=16.4 Hz, 1H) 7.22 (d, J=16.4 Hz, 1H) 7.45 (d, J=8.6 Hz, 1H); ¹³C NMR (125 MHz, DMSO-$d_6$) δ ppm 60.58 (t, G-6') 60.62 (d, G-6) 69.56 (d, G-4) 69.63 (d, G-4' 73.20 (d, G-2') 73.29 (d, G-2) 76.61 (d, G-3') 76.61 (d, G-3) 77.00 (d, G-5') 77.04 (d, G-5) 100.39 (s, G-1') 100.76 (s, G-1) 102.65 (d, C-2') 103.86 (d, C-3) 105.35 (d, C-4' 106.52 (d, C-5) 107.46 (d, C-6') 117.86 (s, C-1) 123.47 (d, C-6) 126.00 (d, a) 127.27 (d, b) 139.77 (s, C-1') 155.86 (s, C-2) 157.96 (s, C-4) 158.40 (s, C-5') 158.92 (s, C-3')

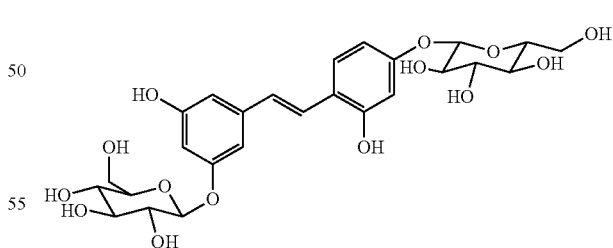

Mulberroside A

Example 6

Preparation and HPLC Quantification Of Extracts from *Morus* Plants

*Morus* samples were collected from different plant parts in different geological locations in S. Korea. The dry plant materials were ground into powder. *Morus* plant powder (20 grams) was mixed with enough diatomaceous earth to fill up a 100 mL extraction cell, and extracted with 70% Ethanol/water by using ASE 350 Extractor (Extraction condition: Heat=5 minutes, Static=5 minutes, Flush=80 volume, Purge=900 seconds, Cycles=3, Pressure=1500 psi, Temperature=60° C.). After extraction, the solution was concentrated with an evaporator at 50° C. to produce a solid extract.

The target components Mulberroside A, Oxyresveratrol, Kuwanon G, Albanin G and Morusin in the *Morus* extracts were quantified with a Luna C18 reversed-phase column (Phenomenex, 10 μm, 250 mm×4.6 mm) in a Hitachi HPLC system at 325 nm. The column was eluted with a binary gradient of 0.1% Formic acid in water (mobile phase A) and acetonitrile (mobile phase B) at 1 ml/min flow rate and 30° C. column temperature.

TABLE 1

Gradient Table of HPLC Analytical Method

| Time (min) | Mobile phase A | Mobile phase B |
|---|---|---|
| 0.0 | 90 | 10 |
| 8.0 | 85 | 15 |
| 35.0 | 10 | 90 |
| 35.1 | 0 | 100 |
| 38.0 | 0 | 100 |
| 38.1 | 90 | 10 |
| 45.0 | 90 | 10 |

Reference Standard Material 72-1 (*Morus* 70% EtOH extract 1-01) produced according to Example 4 was utilized as the quantification standard. All extract samples were prepared in a concentration around 5 mg/ml in MeOH. After sonicating for approximately 15 minutes, the sample solution was cooled in a flask to room temperature and filtered through a 0.45 um nylon syringe filter and 20 μl of the sample was injected into the column.

*Morus* plants were collected from South Korea and China from different geological locations in both countries. The HPLC quantification of Mulberroside A, Oxyresveratrol, Kuwanon G, Albanin G and Morusin content in different species, different plant parts, collected from different locations, and at different age of plants, are listed in Tables 2 and 3.

The actives have been qualified from *Morus* root bark, root wood, fine roots, stem bark, branch, branch bark, branch wood, and twigs. There are small amounts of stilbene-type compounds—Mulberroside A and Oxyresveratrol—detected in *Morus* leaf.

TABLE 2

Quantification of Active Compounds in *Morus* Collected from S. Korea.

| | | Active Content in Extract (%) | | | | | |
|---|---|---|---|---|---|---|---|
| *Morus* No. | Plant Part | Mulberroside A | Oxy-resveratrol | Kuwanon G | Albanin G | Morusin | Extraction Yield (%) |
| MK-1 | Root bark | 10.93 | 0.07 | 1.66 | 0.82 | 0.55 | 23% |
| MK-2 | Root bark | 11.58 | 0.75 | 2.79 | 1.18 | 1.21 | 19% |
| MK-3 | Root wood | 6.40 | 2.26 | 0.58 | 0.20 | 0.24 | 8% |
| MK-4 | Fine root | 9.58 | 2.15 | 2.98 | 1.73 | 1.35 | 15% |
| MK-5 | Stem bark | 2.89 | 0.16 | 0.27 | 0.42 | 0.48 | 19% |
| MK-6 | Root bark | 0.36 | 0.16 | 0.23 | 0.00 | 0.09 | 18% |
| MK-7 | Root bark | 13.28 | 0.00 | 0.25 | 0.00 | 0.00 | 27% |
| MK-8 | Root bark | 11.71 | 0.08 | 0.63 | 0.25 | 0.15 | 21% |
| MK-9 | Root bark | 17.63 | 0.48 | 2.80 | 0.66 | 1.56 | 21% |
| MK10 | Root bark | 0.28 | 0.19 | 1.70 | 0.06 | 0.05 | 16% |
| MK-11 | Leaves | 0.54 | 0.06 | 0.00 | 0.00 | 0.00 | 23% |
| MK-12 | Fruit | 0.00 | 0.00 | 0.00 | 0.00 | 0.00 | 35% |
| MK-13 | Branch | 3.31 | 4.07 | 0.14 | 0.00 | 0.18 | 9% |
| MK-14 | Root bark | 12.51 | 0.39 | 5.73 | 2.48 | 2.42 | 22% |
| MK-15 | Root wood | 1.58 | 2.52 | 0.36 | 0.14 | 0.12 | 7% |
| MK-16 | Branch bark | 22.46 | 0.09 | 0.58 | 0.00 | 0.57 | 15% |
| MK-17 | Branch wood | 4.95 | 1.78 | 0.17 | 0.00 | 0.00 | 5% |
| MK-18 | Root bark | 0.41 | 0.28 | 3.36 | 0.11 | 0.18 | 14% |

TABLE 3

Quantification of Active Compounds in *Morus* Collected from China

| | | Active Content in Extract (%) | | | | | |
|---|---|---|---|---|---|---|---|
| *Morus* No. | Plant Part | Mulberroside A | Oxy-resveratrol | Kuwanon G | Albanin G | Morusin | Extraction Yield (%) |
| MC-1 | Root bark | 1.74 | 0.10 | 7.29 | 6.31 | 5.38 | 17% |
| MC-2 | Root bark | 3.42 | 0.37 | 4.69 | 1.00 | 1.97 | 18% |
| MC-3 | Root bark | 0.04 | 0.05 | 0.34 | 0.00 | 0.12 | 8% |
| MC-4 | Root bark | 0.11 | 0.60 | 0.39 | 0.00 | 0.14 | 8% |
| MC-5 | Root bark | 0.24 | 0.22 | 0.73 | 0.00 | 0.18 | 9% |
| MC-6 | Root bark | 14.07 | 0.36 | 2.06 | 1.29 | 1.42 | 20% |

TABLE 3-continued

Quantification of Active Compounds in *Morus* Collected from China

| Morus No. | Plant Part | Active Content in Extract (%) | | | | | Extraction Yield (%) |
|---|---|---|---|---|---|---|---|
| | | Mulberroside A | Oxy-resveratrol | Kuwanon G | Albanin G | Morusin | |
| MC-7 | Root bark | 9.96 | 1.01 | 2.51 | 0.73 | 0.78 | 12% |
| MC-8 | Root bark | 0.21 | 2.64 | 0.06 | 0.46 | 1.40 | 12% |
| MC-9 | Root bark | 5.85 | 1.44 | 5.11 | 2.41 | 8.70 | 19% |
| MC-10 | Root bark | 2.81 | 0.76 | 11.43 | 4.21 | 3.82 | 11% |
| MC-11 | Root bark | 0.03 | 0.01 | 0.40 | 0.75 | 0.10 | 11% |
| MC-12 | Fruit | 0.00 | 0.00 | 0.00 | 0.00 | 0.00 | 74% |
| MC-13 | Leaves | 0.00 | 0.00 | 0.13 | 0.00 | 0.00 | 20% |
| MC-14 | Twigs | 2.67 | 0.90 | 0.06 | 0.17 | 0.03 | 4% |

Example 7

HPLC Quantification of Extracts from *Morus* Root Bark

Ethanol extracts of *Morus* root barks were obtained from different geological locations in China. The contents of four active components—Mulberroside A, Kuwanon G, Albanin G and Morusin—in those *Morus* extracts were quantified with the HPLC method described in Example 6. As shown in the Table 4, two *Morus* extracts (ME-10 and ME-12) contained none of the four active compounds. Three *Morus* extracts (ME-6, ME-7 and ME-8) contained no Mulberroside A and very small amounts of prenylated flavonoids (less than 4% as a total of the three compounds present). Another four *Morus* extracts (ME-3, ME-4, ME-5, and ME-14) contained small amounts of prenylated flavonoids (less than 2% as a total of the three compounds present) and variable amount of Mulberroside A. This Example clearly demonstrates the lack of enrichment and standardization of stilbene and prenylated flavonoids in regular *Morus* root bark extracts.

TABLE 4

Quantification of Active Compounds in *Morus* Extracts from China

| Morus Extract | Active Content in Extract (%) | | | |
|---|---|---|---|---|
| | Mulberroside A | Kuwanon G | Albanin G | Morusin |
| ME-1 | 20.4 | 2.17 | 0.77 | 1.31 |
| ME-2 | 22.26 | 2.57 | 0.83 | 1.49 |
| ME-3 | 10.86 | 0.42 | 0.17 | 0.22 |
| ME-4 | 1.07 | 0.22 | 0.13 | 0.13 |
| ME-5 | 2.3 | 0.54 | 0.27 | 0.23 |
| ME-6 | 0 | 0.45 | 0.15 | 0.95 |
| ME-7 | 0 | 0.47 | 0.16 | 0.99 |
| ME-8 | 0 | 1.32 | 0.35 | 2.08 |
| ME-9 | 6.7 | 2.29 | 0.99 | 0.91 |
| ME-10 | 0 | 0 | 0 | 0 |
| ME-11 | 6.13 | 2.15 | 1.02 | 0.93 |
| ME-12 | 0 | 0 | 0 | 0 |
| ME-13 | 8 | 2.8 | 1.01 | 1.06 |
| ME-14 | 6.49 | 0.85 | 0.22 | 0.21 |

Example 8

Preparation of *Morus alba* 70% EtOH Extract 10

Dried *Morus alba* roots and root barks (93.3 kg) were cut, crushed, and then extracted with approximately seven-fold volume (700 L) of 70% ethyl alcohol in water (v/v); the extraction was carried out at 100° C. for 4 hrs. The ethanol solution was filtered to obtain the supernatant, which was then concentrated with an evaporator under vacuum at 40° C. This extraction and concentration procedure was repeated two times. The extraction solutions were then combined together and concentrated until the volume become ¹⁄₂₅ of the original volume. The concentrated solution was dried by vacuum freeze-drying to obtain 18.3 kg of *Morus alba* 70% EtOH extract powder 10. The extraction yield was about 19.6% (w/w). The major active component content is listed in Table 5 of Example 12.

Example 9

Preparation of *Morus alba* EtOAc Fraction 11

*Morus alba* EtOH extract produced according to Example 8 was extracted with approximately two-fold volume of ethyl alcohol (EP grade, Ducksan Chemical, Korea) from 4 kg of dried *Morus alba* root bark yielded 570 g of *Morus alba* EtOH extract powder. The EtOH extract was partitioned with hexane and water followed by extraction with ethyl acetate. Extraction was performed by homogenization of the extraction solution at 15,000 rpm for five minutes with homogenizer (IKA T25D, Germany). The well homogenized extraction solution was then separated by centrifuge (Beckman J-20XP, Germany) at 3,000 rpm (rotor #JLA 8.1000) for five minutes. Corresponding n-hexane soluble and water soluble extracts were prepared from 570 g of the crude *Morus alba* EtOH powder. This resulted in production of 80.5 g of the n-hexane soluble extract and 156 g of the water-soluble extract of *Morus alba*. After solvent partition with EtOAc, the upper layer (EtOAc soluble layer) was filtered by filter paper (Hyundai Micro, No. 20, Korea) and the EtOAc solution was collected. The residue (precipitate material) collected from the centrifugation was re-extracted with two-fold volume (300 L) of ethyl acetate (EP grade, Ducksan Chemical, Korea). The re-extracted solution was agitated at 150 rpm for 2 hours. The resulting mixture was then filtered (Hyundai Micro, No. 20, Korea) to obtain an additional EtOAc extract solution. The above-described procedure was repeated two times. The three resulting EtOAc extract solutions were combined and concentrated by evaporator at 40° C. to obtain the final EtOAc extract 11. The final amount of *Morus alba* EtOAc fraction 11, obtained from this process was 327 g. The major active component content is provided in Table 5 (Example 12).

Example 10

Preparation of *Morus alba* 70% EtOH Precipitate Extract 12

*Morus alba* EtOH precipitate extract 12 was produced by follows; 634 kilograms (KG) of dried *Morus alba* roots and root barks were cut, crushed and extracted with approximately 7 fold volume (3600 liters (L)) of 70% ethyl alcohol in water (v/v); the extraction solvent was treated at 80° C., for 4 hrs; the residue was filtered to obtain the supernatant which was then concentrated with an evaporator at 40° C. The above-described procedure was repeated three times. The extraction solutions were then concentrated until the volume become about 1/30 the original starting volumes. Then the concentrated solutions were combined to evaporate again in order to reduce volume of concentrated solution until 1/90 volume of the original extraction solution. The concentrated solution was rested at room temperature for 24 hours (hr) to allow separation into two layers (supernatant and precipitate-layer). The precipitate was filtered and dried by vacuum freeze-drying to obtain *M. alba* 70% EtOH precipitate powder. A total of 24 kg of the resulting product was obtained from 634 kg of raw plant material. The extraction yield was about 3.79% (w/w). The major active component content is listed in Table 5 (Example 12).

Example 11

Preparation of *Morus alba* 70% EtOH Extract (13-1), Precipitate (13-2), and Supernatant (13-3) Extracts

*Morus alba* EtOH precipitate extract was produced as follows: 465 kg of dried *Morus alba* roots and root bark were cut, crushed, and extracted with approximately 10-fold volume (4500 L) of 70% ethyl alcohol in water (v/v); the extraction solvent was treated at 80° C. for 4 hrs; the residue was filtered to obtain the supernatant which was concentrated with an evaporator at 40° C. Above-described procedure was repeated three times. The extraction solutions were concentrated until the volume become 1/30 the original volume. The concentrated solutions were then combined and evaporated again to reduce the volume of the concentrated solution until 1/90 volume of the original extraction solution was achieved. The concentrated solution was left at room temperature for 24 hr to allow separation into a supernatant and precipitate layer. The precipitate layer was then dried by vacuum to obtain 12 kg of *Morus alba* 70% EtOH precipitate powder 13-2. The precipitate yield from *Morus* root barks was about 2.6% (w/w). The supernatant layer was dried by vacuum drying to obtain 24 kg *Morus alba* 70% EtOH supernatant powder 13-3. The extraction yield for the supernatant 13-3 was about 5.2%.

*Morus alba* 70% EtOH combination extract (13-1) was obtained by blending 2 kg of precipitate (13-2) and 4 kg of supernatant (13-3)). The major active component content in both *Morus alba* EtOH extract 13-1, precipitate 13-2 and supernatant 13-3 is listed in Table 5 Example 12).

Example 12

HPLC Quantification of Active Content in Different *Morus alba* Extracts

The detailed HPLC quantification method for Mulberroside A, Oxyresveratrol, Kuwanon G, Albanin G and Morusin content was described in Example 6. Table 5 lists the active contents in different *Morus* root bark extracts as prepared in the Examples 8, 9, 10 and 11.

TABLE 5

Quantification of Active Compounds in *Morus* Extracts

| | Stilbene in Extract (%) | | | Prenylated Flavonoid in Extract (%) | | | Total |
|---|---|---|---|---|---|---|---|
| *Morus* Extracts | Mulberroside A | Oxy-resveratrol | Total Stilbenes | Kuwanon G | Albanin G | Morusin | Prenylated Flavonoids |
| 10 | | | | 2.88 | 1.64 | | |
| 11 | 1.55 | 0.33 | 1.89 | 9.31 | 6.74 | 6.84 | 22.89 |
| 12 | 1.27 | 0 | 1.27 | 5.30 | 4.28 | 4.25 | 13.83 |
| 13-1 | 7.31 | 0.26 | 7.57 | 3.12 | 1.71 | 2.01 | 6.84 |
| 13-2 | 0.76 | 0 | 0.76 | 5.51 | 3.98 | 4.48 | 13.97 |
| 13-3 | 7.50 | 0 | 7.50 | 1.27 | 0.36 | 0.48 | 2.11 |

Example 13

Preparation of Organic Extracts from *Curcuma longa*

A total of 20 grams of dried rhizome powder of *Curcuma longa* were loaded into two 100 ml stainless steel tube and extracted twice with an organic solvent mixture (methylene chloride/methanol in a ratio of 1:1) using an ASE 300 automatic extractor at 80° C. and under 1,500 psi of pressure. The extract solution was filtered, collected, and evaporated with a rotary evaporator to give crude organic extract (OE) (6.04 g, 30.2% yield).

Example 14

High Throughput Purification (HTP) of *Curcuma longa* Organic Extracts

The *Curcuma longa* organic extract (OE, 400 mg) as described in Example 13 was loaded onto a pre-packed flash column (2 cm ID×8.2 cm, 25 ml, 10 g silica gel), eluted using a Hitachi high throughput purification (HTP) system with an unique gradient mobile phase of (A) 50:50 EtOAc: hexanes and (B) methanol from 100% A to 100% B in 30 minutes at a flow rate of 5 mL/min. A total of 88 fractions were collected in a 96-deep-well plate at 1.9 mL per well using a Gilson fraction collector. The sample plate was dried under low vacuum and centrifugation, and then the dried samples were resuspended in 1.5 mL dimethyl sulfoxide (DMSO) per well. A portion (100 µL) from each well was taken and combined (based on UV trace) for the BKB1 inhibition assay.

Example 15

Bradykinin B1 Radioligand Binding Assay of Curcuma Extracts and Fractions Thereof Bradykinin B1 (BKB1) radioligand binding assay was conducted to determine the inhibition activity of *Curcuma longa* OE and extract fractions on BKB1 binding to BKB1 receptor (BKB1R). Membranes from human IMR-90 lung fibroblasts, stimulated with IL-1β in modified HEPES buffer (PH=7.4), were incubated with a test sample in the presence of 0.9 nM [$^3$H](Des-Arg$^{10}$)-Kallidin for 60 minutes at room temperature. After incubation, membranes were filtered and washed five times with modified DPBS buffer (pH=7.4). Samples were scintillation counted to determine the amount of specifically bound to the BKB1 receptor containing membrane.

The *Curcuma longa* OE was tested at a concentration of 166 µg/mL and IC$_{50}$ values were determined using the same method with serial dilutions at concentrations ranging from 400 µg/mL and 5 ng/mL to obtain a dose-response curve. Data showing inhibition of BKB1 binding to BKB1R by *Curcuma longa* OE extracts is provided in Table 6.

TABLE 6

Inhibition of BKB1Receptor Binding by *Curcuma longa* OE

| Sample | BKB1(166 µg/ml) POC (%) | BKB1 IC$_{50}$ (µg/mL) |
|---|---|---|
| OE extract | −0.14 | 9.6 |

*Curcuma longa* OE showed strong inhibition of BKB1 binding with an IC$_{50}$ of about 9.6 µg/mL. Furthermore, HTP fractions of the *Curcuma longa* OE were examined in the BKB1 binding assay (data not shown). The activity profile of the HTP fractions indicates that fractions 11-22, 34, and 38 had the most potent BKB1 receptor binding inhibition, with a mean percentage of control (POC) below 10%. Curcuminoids were found to be the major active compounds associated with the activity of HTP fractions 11-22.

Example 16

BKB1 AND BKB2R Binding Activity of *Curcuma* Compounds

BKB1 binding assay, as described in Example 15, was used to test curcumin compound isolated from a *Curcuma longa* extract (Compound 11), as well as commercially available curcumin purchased from Sigma-Aldrich (C1386). Curcumin was tested at final concentrations ranging from 200 µM to 5 nM. Binding curves were plotted by non-linear regression fit (using GraphPad Prizm software). K$_i$ values were computed using Cheng-Prusoff algorithm. In addition, inhibition of BKB2 receptor binding activity by curcumin was examined with methods similar to those described in Example 15 for the BKB1 receptor with some modifications. Bradykinin Radioligand Binding Assay (BKB2) was conducted using a standard assay under the following conditions:

1. Composition of Assay Buffer: 24 mM TES, pH 6.8, 1 mM 1.10-Phenanthrioline, 0.3% BSA.
2. Source of BKb2R: CHO-K1 cells expressing recombinant human BKb2R
3. Ligand: [$^3$H]-Bradykinin: 0.2 nM.
4. Incubation time: 90 min RT.
5. Reading: TopCount.

Commercial curcumin (Sigma, C1386) was tested at concentrations ranging from 200 µM to 5 nM. Binding curves for commercial curcumin does not conform to mass action law for competitive inhibitor. K$_i$ was manually calculated by using Cheng-Prusoff equation. The inhibition activity for BKB1 and BKB2 by curcumin is provided in Table 7.

TABLE 7

Inhibition of BKB1 and BKB2 by *Curcumin*

| Compound | BKB1 Ki (µg/ml) | BKB2 Ki (µg/ml) |
|---|---|---|
| Curcumin | 2.173 | 58 |

The data indicate that curcumin is a selective BKB1 antagonist since it shows much stronger inhibition of BKB1 binding activity as compared to BKB2 binding.

Example 17

Preparation of *Curcuma longa* Ethyl Alcohol Extract 19

*Curcuma* EtOH extract was produced as follows: 20 kg of dried *Curcuma longa* rhizomes (roots) were pulverized, and extracted with approximately 4-fold volume (80 L) of 100% ethyl alcohol and the extraction solvent held at 80-85° C. for 30 hrs. The residue was filtered to obtain a supernatant that was concentrated with an evaporator at 85-90° C. The extraction solutions were then concentrated until the volume was ½5 of the original volume. The concentrated solution was dried by spray dry process (temperature I/P 200° C. and O/P 95° C.) to obtain about 1 kg of 25% *Curcuma* in EtOH extract powder 19 with reddish-orange color. The extraction yield was about 5% (w/w).

Example 18

Quantification of Curcumin in *Curcuma* Rhizome Extract

The following analytical method was used to determine the amount of Curcumin in the *Curcuma longa* rhizome extracts. An Agilent HPLC/PDA system was used with a C18 reversed-phase column (Phenomenex, USA, Luna 5 um, 250 mm×4.6 mm) for detection and quantitation of Curcumin and minor components. A binary 0.1% acetic acid in purified water (mobile phase A) and acetonitrile (mobile phase B) gradient was used for elution of Curcumin components as described in Table 7. The flow rate was set to 1 ml/min passing through the Luna C18 column with a column temperature of 35° C. The UV detector was set to read absorbance at 407 nm.

TABLE 7

Curcumin HPLC Gradient Elution Scheme

| Time (min) | Mobile phase A % | Mobile phase B % |
|---|---|---|
| 0 | 55 | 45 |
| 10.0 | 55 | 45 |
| 10.1 | 10 | 90 |
| 25.0 | 10 | 90 |
| 25.1 | 55 | 45 |
| 30.0 | 55 | 45 |

The quantification standard—Curcumin was purchased from Sigma-Aldrich Co. The highest concentration level of Curcumin was 0.05 mg/ml and diluted to L5 from L1(0.0031 mg/ml) using methanol. Concentration of *Curcuma longa* rhizome extract samples were adjusted to about 1 mg/ml in methanol in a volumetric flask and sonicated until dissolved (approximately 20 minutes), then cooled to room temperature, mixed well and filtered through a 0.45 μm nylon syringe filter. Then 10 μl of sample was quantified by HPLC, which results for *Curcuma longa* rhizome extract are provided in Table 8.

TABLE 8

HPLC Quantification of *Curcuma longa* Rhizome Extract

| Sample | Curcumin % | Curcuminoids (total) % |
|---|---|---|
| 110 | 16.34 | 30.04 |
| 210 | 14.71 | 27.93 |
| 310 | 13.08 | 26.53 |

Example 19

Preparation of *gambir* (*Uncaria gambir*) Extract 21

*Uncaria gambir* water extract was produced as follows. 100 kg of dried leaves of *Uncaria gambir* was cut, crushed, and extracted with 15-fold volume (1500 L) of 70% ethyl alcohol and the extraction solvent treated at 80° C. for 7 hrs. The resulting residue was filtered to obtain a supernatant. The above-described procedure was repeated for second time. The extraction supernatant solutions were combined together and concentrated with an evaporator at 46° C. under vacuum condition until the volume became 1/30$^{th}$ of the original volume. The concentrated solution was evaporated further to reduce volume of concentrated solution until 1/90 volume of the original solution. The resulting concentrated solution was then rested at room temperature for 24 hrs to allow precipitate to form in the concentrated solution. The precipitate was filtered and dried under vacuum to obtain precipitate powder as *Uncaria gambir* extract powder 21. The yield from 100 kg of dried leaves of *Uncaria gambir* was about 6 kg of extract powder, so the extraction yield was about 6% (w/w).

Example 20

HPLC Quantification of *Uncaria gambir* Extracts

The following analytical method was used to determine the amount of catechin in the *Uncaria gambir* leaf extracts. An Agilent HPLC/PDA system with a C18 reversed-phase column (Phenomenex, USA, Luna 5 um, 250 mm×4.6 mm) was used for the detection and quantitation of catechin compound in Gambir extracts. A binary column gradient was used for elution of material from the column. Mobile Phase A: 0.1% phosphoric acid in purified water, and Mobile Phase B: acetonitrile gradient was used for elution (Table 9). The flow rate was set to 1.0 ml/min passing through the Luna C18 column with a column temperature of 35° C. The UV detector was set to record absorbance at 275 nm.

TABLE 9

Gradient Table of HPLC Analytical Method

| Time (min) | Mobile Phase A | Mobile Phase B |
|---|---|---|
| 0.0 | 85.0 | 15.0 |
| 7.0 | 85.0 | 15.0 |
| 12.0 | 10.0 | 90.0 |
| 16.5 | 10.0 | 90.0 |
| 16.6 | 85.0 | 15.0 |
| 24.0 | 85.0 | 15.0 |

Pure catechin reference sample was purchased from Sigma-Aldrich Co. The reference sample was dissolved in MeOH:0.1% $H_3PO_4$ (1:1). Highest level concentration range of catechin was 0.5 mg/ml and diluted to L5 from L1 (0.003 mg/ml) using 50% methanol in 0.1% $H_3PO_4$. Concentration of the Gambir extract samples were adjusted to 2 mg/ml in 50% methanol in 0.1% $H_3PO_4$ in a volumetric flask and sonicated until dissolved (approximately 10 minutes), and then cooled to room temperature, mixed well and filtered through a 0.45 μm nylon syringe filter. HPLC analysis was performed by injecting a 20 μl sample into the HPLC.

TABLE 10

HPLC Quantification of *Gambir* Extract

| Sample | Catechin % |
|---|---|
| 210 | 20.0 |
| 212 | 18.5 |

Example 21

Preparation of *Acacia catechu* 65% Catechin Extract

*Acacia catechu* 65% catechin extract was produced as follows: 500 kg of *Acacia catechu* (KATHA) was put into 750 L of 50% ethyl alcohol and stirred at room temperature for 90 min. After 500 L of ethyl acetate was put into the homogenized KATHA slurry, it was stirred smoothly for 30 min. The slurry was allowed to separate into two layers for 1 hr. The ethyl acetate layer was moved into a new bottle, and the partition was repeated with the water layer. Both the 1st and 2nd ethyl acetate layers were combined and concentrated at 60-62° C. until TDS 30%, and then spray dried (temp. I/P 190° C.-O/P 90° C.). A total of 72.5 kg *Acacia catechu* extract was obtained from 500 kg of raw material with catechin and epicatechin total content at not less than 65%. The extraction yield was 14.5% (w/w).

Example 22

Ex Vivo Glycosaminoglycans (GAG) Release Assay

Articular cartilage from hock joints of rabbits (2.5 kg body weight) was removed immediately after each animal was sacrificed and articular cartilage explants were obtained by following the method described by Sandy et al. (*Biochem. Biophy Acta* 543:36, 1978).

Briefly, after the articular surfaces were surgically exposed under sterile conditions, approximately 200-220 mg articular surfaces per joint were dissected and submerged into complete medium (DMEM, supplemented with heat inactivated 5% FBS; penicillin 100 U/ml; streptomycin 100 ug/ml). They were then rinsed several times with the complete medium and incubated for 1 to 2 days at 37° C. in a humidified 5% $CO_2$/95% air incubator for stabilization. The complete medium was replaced with a basal medium (DMEM, supplemented with heat-inactivated 1% FBS, 10 mM HEPES, and penicillin 100 U/ml streptomycin 100 μg/ml). Approximately 30 mg cartilage pieces (2×3×0.35 mm/piece) were placed in 24-well plates and treated with given concentrations of test agents. After pretreatment for 1 h, 5 ng/ml of rhIL-1α was added to the culture medium and further incubated at 37° C. in a humidified 5% $CO_2$/95% air incubator. The culture medium was collected 24 h later and stored at –20° C. until assay.

The amount of sulphated GAGs (e.g., released from proteoglycans) in the medium at the end of the reaction reflects the amount of articular cartilage degradation, which was determined using the commercially available 1,9-dimethy-methylene blue method according to the instructions of the manufacturer (Blyscan™ assay, Accurate Chemical and Scientific Corp., Westbury, New York).

Example 23

Effect of Purified Compounds from *Morus* on Ex Vivo Gag Release

Rabbit cartilage explants were cultured with rhIL-1α (5 ng/ml) in the absence or presence of purified *Morus* compounds isolated according to Example 3 to examine the protective effects on proteoglycan (PG) degradation. Purified compound inhibited rhIL-1α-mediated degradation of PG in a concentration dependent manner. Especially, Mulberroside A, Oxyresveratrol and Morusin showed a strong inhibitory effect when compared with diclofenac treated group.

TABLE 12

Effect of *Morus* Compounds on Ex Vivo GAG Release

| Sample | Dose | % GAG release |
|---|---|---|
| Normal | — | 36.6 |
| IL-1α | 5 ng/ml | 100 |
| Diclofenac | 300 μg/ml | 34.6 |
| Mulberoside A | 25 μg/ml | 73.1 |
|  | 50 μg/ml | 75.8 |
|  | 100 μg/ml | 70.5 |
| Kuwanon G | 25 μg/ml | 56.6 |
|  | 50 μg/ml | 48 |
|  | 100 μg/ml | 44.4 |
| Oxyresveratrol | 25 μg/ml | 59.8 |
| Morusin | 25 μg/ml | 48.4 |
|  | 50 μg/ml | 49.9 |
|  | 100 μg/ml | 33.6 |

Example 24

Morus Extract Reduces Ex Vivo Gag Release

Rabbit cartilage explants were cultured with rhIL-1a (5 ng/ml) in the absence or presence of *Morus* extracts to examine the protective effects on PG degradation. *Morus* extracts inhibited rhIL-1α-mediated degradation of PG in a concentration dependent manner. All samples showed a strong effect as compared to that of IL-1α treated group.

TABLE 13

Effect of *Morus* Extracts on Ex Vivo GAG Release

| Sample | Dose | % GAG release |
|---|---|---|
| Normal | / | 36.6 |
| IL-1α | 5 ng/ml | 100 |
| Diclofenac | 300 μg/ml | 34.6 |
| 13-1 | 100 μg/ml | 50.2 |
|  | 200 μg/ml | 41.9 |
| 11 | 100 μg/ml | 49.9 |
|  | 200 μg/ml | 37.3 |
| 13-3 | 100 μg/ml | 67.20 |
|  | 200 μg/ml | 61.3 |

Example 25

Preparation of Ethanol Extracts from *Mentha piperita*

Peppermint (*Mentha piperita*) 90% EtOH extract (lot #RM604-13002) was produced as follows: 73.4 kg of dried *Mentha piperita* was cut, crushed, and extracted with a 15-fold volume (1100 L) of 90% ethyl alcohol (v/v) at 85° C. for 3 hrs. The resulting residue was filtered to obtain a supernatant that was concentrated with a vacuum evaporator at 40° C. The resulting residue was extracted a second time with 13-fold volume (950 L) of 90% ethyl alcohol (v/v) at 40° C. for 1 hrs and filtered to obtain a second supernatant which was concentrated with a vacuum evaporator at 40° C. The resulting concentrated cake was dried under vacuum to obtain 19.3 kg of Peppermint 90% EtOH extract powder designated as Extract 25. The extraction yield was 25.3% (w/w).

Example 26

Preparation of Methanol and Other Oragnic Extracts From *Mentha piperita*

Dried ground peppermint leaf powder (*Mentha piperila*) (21.7 g) loaded into two 100 ml stainless steel tubes and extracted twice with an organic solvent mixture (methanol) using an ASE 300 automatic extractor at 80° C. under a pressure of 1,500 psi. The extract solution was automatically filtered, collected, and evaporated with a rotary evaporator to give a crude organic extract (ME 26-1) (4.48 g, 20.64% yield).

Alternatively, 252.3 g of dried ground leaf powder of *Mentha piperita* was extracted with methanol three times by refluxing one hour each time. The organic solution was combined and evaporated under vacuum to provide methanol extract (ME 26-2) 40.88 g with a yield of 16.20%.

Similar results were obtained using the same procedure, but with the organic solvent being replaced with methanol or ethanol to provide a methanol extract (ME) or ethanol extract (EE), Ethanol:$H_2O$ (7:3) extracts, Ethanol:$H_2O$ (1:1) extracts, Ethanol:$H_2O$ (3:7) extracts and water extracts respectively.

Example 27

Effect of *Curcuma* and *Uncaria* Extracts on Ex Vivo Gag Release

Rabbit cartilage explants were cultured with rhIL-1α (5 ng/ml) in the absence or presence of *Curcuma* extract from Example 17 or *Uncaria* extract from Example 19 to examine the protective effect on PG degradation. *Curcuma* extract 19 decreased rhIL-1α-mediated degradation of PG in a concentration dependent manner, while *Uncaria* extract 21 showed a weak protective effect on PG degradation.

TABLE 14

Effect of *Curcuma* and *Gambir* Extracts on Ex Vivo GAG Release

| Sample | Dose | % GAG release |
|---|---|---|
| (—) | — | 39.0 |
| IL-1α | 5 ng/ml | 100.0 |
| Diclofenac | 300 μg/ml | 45.6 |
| 19 | 30 μg/ml | 88.9 |
| (*Curcuma*) | 50 μg/ml | 65.0 |
| | 66.7 ug/ml | 59.2 |
| | 100 μg/ml | 38.2 |
| | 300 ug/ml | 50.4 |
| 21 | 66.7 μg/ml | 97.7 |
| (*Gambir*) | 80 μg/ml | 81.0 |
| | 100 μg/ml | 78.0 |
| | 120 μg/ml | 86.4 |
| | 200 μg/ml | 88.4 |
| | 300 μg/ml | 88.4 |

Example 28

Effect of Peppermint Extract on Ex Vivo Gag Release

Rabbit cartilage explants were cultured with rhIL-1α (5 ng/ml) in the absence or presence of Peppermint extract from Examples 25 and 26 to examine the protective effects on PG degradation.

TABLE 15

Effect of Peppermint Extracts on Ex Vivo GAG Release

| Sample | Dose | % GAG release |
|---|---|---|
| Normal | — | 34.5 |
| IL-1α | 5 ng/ml | 100 |
| Diclofenac | 300 μg/ml | 22.6 |
| 191-8 | 150 μg/ml | 110.9 |
| | 250 μg/ml | 84.1 |
| | 500 μg/ml | 73.0 |
| 622-9 | 150 μg/ml | 91.5 |
| | 250 μg/ml | 79.2 |
| | 500 μg/ml | 68.7 |

Peppermint extract inhibited rhIL-1α-mediated degradation of PG in a concentration dependent manner, although the effect of Peppermint extracts on PG degradation were weaker than the diclofenac treated group.

Example 29

Effect of *Curcuma longa* (C):*Morus* (M) Compositions on Ex Vivo Gag Release Rabbit cartilage explants were cultured for 24 hr with rhIL-1α (5 ng/ml) in the absence or presence of a mixture of *Curcuma* and *Morus* extracts to examine the protective effects on PG degradation. The plant extracts from *Morus* and *Curcuma* were produced according Examples 8 and 17, respectively. *Curcuma* and *Morus* extracts were combined at different ratios, including 4:1, 2:1, 1:1, 1:2 and 1:4, respectively. The compositions were tested at four doses—50, 100, 200 and 300 μg/ml. As shown in Table 17, all compositions of plant extracts prevented rhIL-1α mediated degradation of articular cartilage in a concentration dependent manner.

TABLE 17

Effect of *Morus*/*Curcuma* Compositions on Ex Vivo GAG Release

| Sample | Dose (μg/ml) | % GAG release |
|---|---|---|
| (—) | — | 51.9 |
| IL-1α | 0.005 | 100.0 |
| Diclofenac | 300 | 36.8 |
| 4C:1M | 50 | 80.5 |
| | 100 | 58.1 |
| | 200 | 49.1 |
| | 300 | 61.8 |
| 2C:1M | 50 | 82.0 |
| | 100 | 57.5 |
| | 200 | 47.4 |
| | 300 | 68.4 |
| 1C:1M | 50 | 88.7 |
| | 100 | 62.0 |
| | 200 | 54.2 |
| | 300 | 59.7 |
| 1C:2M | 50 | 81.6 |
| | 100 | 59.5 |
| | 200 | 58.0 |
| | 300 | 57.2 |
| 1C:4M | 50 | 62.6 |
| | 100 | 63.3 |
| | 200 | 56.7 |
| | 300 | 32.7 |

Example 30

Evaluation of *Curcuma* (C):*Morus* (M) Composition Synergy on Ex Vivo Gag Release Rabbit cartilage explants were cultured for 24 hr with rhIL-1α (5 ng/ml) in the absence or presence of compositions of *Curcuma* extract, *Morus* extract, or a mixture thereof to examine the presence of a protective effect on PG degradation. The plant extracts from *Morus* and *Curcuma* were produced according Examples 8 and 17, respectively. *Curcuma* and *Morus* extracts were combined at different ratios, including 1:2 and 1:4. The compositions were tested at two doses—200 and 300 μg/ml, or at one dose—75 μg/ml to examine whether the combined extracts worked synergistically or additively. The individual extract compositions were tested at concentrations that were in proportion to the weight content of those extracts in the mixed composition.

TABLE 18

Synergistic Effect of C:M Composition versus C or M Alone

| Cmpsn | μg/ml | % Inhibition | Cmpsn | μg/ml | % Inhibition | Remark |
|---|---|---|---|---|---|---|
| 1C:4M | 200 | 85.1 | 1C:4M | 300 | 97.8 | Theoretical value |
| 1C:4M | 200 | 87.8 | 1C:4M | 300 | 100 | Experimental result |

TABLE 18-continued

Synergistic Effect of C:M Composition versus C or M Alone

| Cmpsn | µg/ml | % Inhibition | Cmpsn | µg/ml | % Inhibition | Remark |
|---|---|---|---|---|---|---|
| C | 40 | 49.1 | C | 60 | 72.6 | Individual |
| M | 160 | 70.7 | M | 240 | 92 | Individual |
| 1C:2M | 200 | 81.7 | 1C:2M | 300 | 95.6 | Theoretical value |
| 1C:2M | 200 | 95.8 | 1C:2M | 300 | 100 | Experimental result |
| C | 66.7 | 59.9 | C | 100 | 85 | Individual |
| M | 133.3 | 54.3 | M | 200 | 70.6 | Individual |
| 1C:1M | 75 | 53 | | | | Theoretical value |
| 1C:1M | 75 | 57.5 | | | | Experimental result |
| C | 37.5 | 33 | | | | Individual |
| M | 37.5 | 29.9 | | | | Individual |

Compositions of *Curcuma* and *Morus* extracts interfered with the rhIL-1α-mediated degradation of PG in a concentration dependent and synergistic manner. Especially, compositions 1C:4M (5 wt % curcuminoids, 2.4 wt % prenylated flavonoids, 2.4 wt % stilbenes) and 1C:2M (8.3 wt % curcuminoids, 2 wt % prenylated flavonoids, 2 wt % stilbenes) showed a synergistic effect at 200 and 300 µg/ml. Composition 1C:1M (12.5 wt % curcuminoids, 1.5 wt % prenylated flavonoids, 1.5 wt % stilbenes) also showed a synergistic effect at 75 µg/ml. Synergy values were calculated by using the COLBY formular (Colby, Weeds 15:20, 1967).

Example 31

Effect Of *Curcuma* (C):*Morus* (M):N-Acetyl Glucosamin (NAG) Compositions on Ex Vivo Gag Release Rabbit cartilage explants were cultured for 24 hr with rhIL-1α (5 ng/ml) in absence or presence of composition of *Curcuma* and *Morus* extract to examine the protective effects on PG degradation. The plant extracts from *Morus* and *Curcuma* were produced according to Examples 8 and 17, respectively. *Curcuma* and *Morus* extracts were combined with N-Acetyl Glucosamine (NAG) at a ratio 1C:1M:2NAG. The compositions were tested at four doses—50, 100, 200 and 300 µg/ml. The individual extracts in the compositions were tested at concentrations that were in proportions of the weight contents of those extracts in the compositions. Synergy values were calculated by using the Colby formular (Colby, *Weeds* 15:20, 1967).

TABLE 19

Effect of *Curcuma*, *Morus*, and NAG Compositions

| Sample | Dose | % GAG release |
|---|---|---|
| Normal | — | 40.7 |
| IL-1α | 5 ng/ml | 100.0 |
| Diclofenac | 300 µg/ml | 30.1 |
| 1C:1M:2NAG | 50 µg/ml | 83.2 |
| | 100 µg/ml | 59.7 |
| | 200 µg/ml | 52.7 |
| | 300 µg/ml | 46.4 |
| *Curcuma* | 12.5 µg/ml | 71.8 |
| | 25 µg/ml | 74.9 |
| | 50 µg/ml | 50.8 |
| | 75 µg/ml | 58.4 |

TABLE 19-continued

Effect of *Curcuma*, *Morus*, and NAG Compositions

| Sample | Dose | % GAG release |
|---|---|---|
| *Morus* | 12.5 µg/ml | 76.3 |
| | 25 µg/ml | 77.7 |
| | 50 µg/ml | 70.9 |
| | 75 µg/ml | 70.9 |
| NAG | 12.5 µg/ml | 95.7 |
| | 25 µg/ml | 99.2 |
| | 50 µg/ml | 87.5 |
| | 75 µg/ml | 81.2 |

As shown in the Table 19, the composition of plant extracts prevented with the rhIL-1α mediated degradation of articular cartilage in a concentration dependent manner. In particular, a 1C:1M:2NAG compostion showed an unexpected synergistic effect at 300 µg/ml as compared to the three individual extracts alone (Table 20).

TABLE 20

Synergistic Effect of C:M:NAG Compositions

| Sample | Dose | % Inhibition | Remark |
|---|---|---|---|
| 1C:1M:2NAG | 300 µg/ml | 89.6 | Theoretical value |
| 1C:1M:2NAG | 300 µg/ml | 90.5 | Experimental result |
| C | 75 µg/ml | 70.1 | Individual |
| M | 75 µg/ml | 49.2 | Individual |
| NAG | 150 µg/ml | 31.8 | Individual |

Example 32

Formulation of *Morus* Root Bark Extract with Other Actives and Ingredients

The bone density compositions were formulated with *Morus* root bark extracts with other active and/or excipient ingredients set forth in the following compositions.

Supplement Facts

Serving Size: Two (2) Tablets per day

Directions: Take one (1) Tablet twice daily with meals.

| Composition 1 | | |
|---|---|---|
| Amount per Serving | Amount | % Daily Value |
| Glucosamine Hydrochloride | 1,500 mg | * |
| Chinese mulberry extract (*Morus alba*) (root bark) | 200 mg | * |
| *Curcumin* extract (*Curcuma longa*) (rhizome) | 200 mg | * |
| Vitamin D3 (as cholecalciferol) | 400 IU | 100% |
| Calcium (elemental) | 600 mg | 60% |

*Daily Value not established

| Composition 2 | | |
|---|---|---|
| Amount per Serving | Amount | % Daily Value |
| Glucosamine Hydrochloride | 1,500 mg | * |
| Chondroitin sulfate | 1,200 mg | * |
| Chinese mulberry extract (*Morus alba*) (root bark) | 100 mg | * |

-continued

Composition 2

| Amount per Serving | Amount | % Daily Value |
|---|---|---|
| Curcumin extract (Curcuma longa) (rhizome) | 50 mg | * |
| Vitamin D3 (as cholecalciferol) | 400 IU | 100% |
| Calcium (elemental) | 300 mg | 30% |

*Daily Value not established

Composition 3

| Amount per Serving | Amount | % Daily Value |
|---|---|---|
| N-Acetyl-Glucosamine | 1,000 mg | * |
| Chondroitin sulfate | 200 mg | * |
| Chinese mulberry extract (Morus alba) (root bark) | 150 mg | * |
| Gambir extract (Uncaria gambir) (whole plant) | 150 mg | * |
| Vitamin D | 800 IU | 200% |
| Calcium Citrate (elemental) | 1,000 mg | 100% |
| Magnesium Citrate | 300 mg | 75% |
| Vitamin K1 | 100 mcg | 125% |
| Vitamin K2 | 10 mcg | 12.5% |

*Daily Value not established

Composition 4

| Amount per Serving | Amount | % Daily Value |
|---|---|---|
| Chinese mulberry extract (Morus alba) (root bark) | 250 mg | * |
| Curcumin (Curcuma longa) (rhizome) | 250 mg | * |
| Vitamin D3 | 800 IU | 200% |
| Calcium (elemental) | 1,000 mg | 100% |
| Magnesium Citrate | 400 mg | 100% |
| Phosphorus | 300 mg | 30% |
| Boron (Citrate) | 200 mcg | * |
| Zink (Citrate) | 13 mg | 87% |

*Daily Value not established

Other ingredients: microcrystalline cellulose, croscarmellose sodium, hydroxypropyl cellulose, stearic acid, coating silicon dioxide, glycerin, hydroxypropyl methylcellulose.

This composition provides support of bone and bone and cartilage health. It prevents bone loss, increase bone density and provides bone and cartilage comfort by rejuvinating cartilage, lubricating connective tissue and strengthening bones. The composition helps you to keep moving and to stay strong and flexible. Bone & Joint Support provides 4-way protection for your joints and bones:

Glucosamine Hydrochloride is provided to protect and strengthen joints*.

Morus alba bioflavonoids are provided to act as potent antioxidants, to protect joints against harmful inflammation and oxidants that breakdown bone and cartilage tissues*.

Vitamin D3 is provided for enhanced mineral absorption to help support and nourish bones*.

Calcium is provided to improve bone strength and increase bone density*.

Example 33

Mono-Iodoacetate (MIA) Induced Osteoarthritis Model

Osteoarthritis (OA) is a degenerative joint disease characterized by joint pain and a progressive loss of articular cartilage and, to date, with no cure. As the disease advances, the biochemical alterations that occur within the articular cartilage will result in imbalances between anabolic and catabolic processes that ultimately alter the overall joint structure and function, and lead to chronic pain. Multiple animal models have been developed and utilized to study the pathogenesis of OA and to evaluate the effectiveness of novel therapeutic agents with limited success. An animal model with a robust induction and reproducibility of joint pathology, along with pain associated with the disease, was desired, so the minimally invasive mono-iodoacetate (MIA) induced OA model was employed. Mono-iodoacetate (MIA) is an inhibitor of glyceraldehyde-3-phosphate dehydrogenase activity shown to induce chondrocyte death and hence reproduces cartilage lesions with loss of proteoglycan matrix and functional joint impairment similar to human OA (Marker and Pomonis, Methods Mol. Biol. 851:239, 2012).

Male Sprague-Dawley (SD) rats weighing about 170 to about 230 g (6 weeks of age) were purchased and acclimated for one week. One day before disease induction, animals were randomized into four group as follows: G1 (Normal), G2 (Vehicle), G3 (Diclofenac; 10 mg/kg) and G4 (G:M; 500 mg/kg). Each group was orally gavaged with their respective treatment. Anesthetized rats were injected with 0.8 mg of MIA in a 50 µl saline solution into the intra-articular pocket one hour after the second dose of treatments. Pain sensitivity was measured once a week using a Randall-Salitto meter and treatment lasted for 6 weeks. Body weights were measured once a week to calculate the respective weekly dosage of each group. Once the in-life study was concluded, structural and cellular alterations of joint tissues as a result of disease progression and/or treatment efficacy was assessed by using histopathology with a modified Mankin scoring system.

Example 34

Bone Histomorphometry in Therapeutic MIA Induced Osteoarthritis Model

Male Sprague-Dawley (SD) rats weighing 170~230 g (6 weeks of age) were purchased and acclimated for one week. One day before disease induction, animals were randomized into four group of Normal, Vehicle, Diclofenac (10 mg/kg) and GM (500 mg/kg). Anesthetized rats were injected with 0.8 mg of MIA in 50 µl saline solution into the intra-articular pocket. One week after MIA induction, samples were administrated daily with gastric tube for 6 weeks.

Bone histomorphometry was evaluated on both femur and tibia per knee joint in rats from the MIA-induced osteoarthritis model by Micro CT scan using an Inveon™ unit (Siemens Healthcare USA, Inc., Pennsylvania, USA) at Korea Basic science institute, Ochang, Korea. BMD was used as an indicator of osteoporosis and fracture risk; BV/TV as an indicator of trabecular bone volume refers to the ratio of the trabecular bone volume to the total volume; BS/BV as an indicator of trabecular turnover refers to the ratio of the trabecular bone surface to the trabecular bone volume of a region of interest.

As shown Table 21, BMD in the GM group was significantly increased when compared with that of vehicle group. BV/TV showed the increasing tendency in G:M group when compared to that of vehicle group. Diclofenac (positive control) group showed decreasing tendency in BV/TV (Table 21).

TABLE 21

Change in BMD and Bone Architecture in Therapeutic MIA Model

|  | Normal | Vehicle | Diclofenac (10 mg/kg) | GM (500 mg/kg) |
|---|---|---|---|---|
| BMD (mg/cm3) | 1023.5 ± 8.3 | 881.9 ± 64.0 | 896.2 ± 29.4 | 956.2 ± 43.7* |
| BV/TV (%) | 74.76 ± 2.60 | 68.24 ± 5.03 | 65.35 ± 7.75 | 70.12 ± 4.97 |
| BS/BV | 7.22 ± 0.65 | 8.76 ± 1.13 | 9.11 ± 1.41 | 8.22 ± 1.09 |

Data represented as mean ± SD.
*p < 0.05 (vs vehicle).
BV/TV; total trabecular bone volume/total tissue (bone + marrow) volume Example 35

Bone Histomorphometry In Concurrent Mia-induced Osteoarthritis Model

Male Sprague-Dawley (SD) rats weighing 170~230 g (6 weeks of age) were purchased and acclimated for one week. One day before disease induction, animals were randomized into four group of Normal, Vehicle, Diclofenac (10 mg/kg) and G:M (500 mg/kg). Anesthetized rats were injected with 0.8 mg of MIA in 50 μl saline solution into the intra-articular pocket at 1 hour after sample treatments. And then samples were administrated daily with gastric tube for 6 weeks.

Bone histomorphometry was evaluated on both femur and tibia per knee joint by Micro CT scan using an Inveon™ unit (Siemens Healthcare USA, Inc., Pennsylvania, USA) at Korea Basic science institute, Ochang, Korea. BV/TV as an indicator of trabecular bone volume is the ratio of the trabecular bone volume to the total volume. BMD used as an indicator of osteoporosis and fracture risk. Therefore, we checked those markers whether GM has the efficacy on the osteoporosis.

As shown Table 22, BMD in both Diclofenac and G:M group was significantly increased when compared to that of vehicle group. Both Diclofenac and GM groups had tendency to increase BV/TV values in comparison against vehicle group in MIA rats. (Table 22).

TABLE 22

Change in BMD and Bone Architecture in Concurrent MIA-Induced Model

|  | Normal | Vehicle | Diclofenac (10 mg/kg) | GM (500 mg/kg) |
|---|---|---|---|---|
| BMD (mg/cm3) | 1023.5 ± 8.3 | 881.9 ± 64.0 | 982.3 ± 19.44 | 996.1 ± 11.64 |
| BV/TV (%) | 74.76 ± 2.60 | 68.24 ± 5.03 | 71.89 ± 5.43 | 70.84 ± 5.92 |

Data represented as mean ± SD.
*p < 0.05 (vs vehicle).
BV/TV; total trabecular bone volume/total tissue (bone + marrow) volume Example 36

Ovariectomized (OVX) Osteoporosis Model

CM (a proprietary blend of Curcuma longa and Morus alba extracts) was tested to show the improvement of bone mineral density (BMD) in ovariectomized (OVX) rats. Briefly, female Sprague-Dawley (SD) rats weighing 190~220 g (7 weeks of age) were purchased and acclimated for one week. Rats were randomly divided into ovariectomy (OVX) and sham operation group (n=10). OVX was performed through flank incision under isoflurane anesthesia. Similar surgical procedures were applied to the sham group except the ovaries were not removed.

OVX rats were divided into OVX control group, Morus-, Curcumin- and C:M-treated groups at three dosages. Ten weeks after the OVX or sham operation, all samples were administrated daily for 12 weeks. Sham and OVX control rats received the same volume of 0.5% carboxymethyl cellulose (CMC) as vehicle. Osteoporosis related parameters including BMD, total trabecular bone volume/Total tissue (BV/TV), trabecular thickness (TH/TB) were analyzed.

TABLE 23

Change of BMD and architecture in therapeutic MIA induced model.

|  | Normal | Vehicle | Diclofenac (10 mg/kg) | G:M (500 mg/kg) |
|---|---|---|---|---|
| BMD (mg/cm3) | 1023.5 ± 8.3 | 881.9 ± 64.0 | 896.2 ± 29.4 | 956.2 ± 43.7* |
| BV/TV (%) | 74.76 ± 2.60 | 68.24 ± 5.03 | 65.35 ± 7.75 | 70.12 ± 4.97 |
| BS/BV | 7.22 ± 0.65 | 8.76 ± 1.13 | 9.11 ± 1.41 | 8.22 ± 1.09 |

Data represented as mean ± SD.
*p < 0.05 (vs vehicle).
BV/TV; total trabecular bone volume/total tissue (bone + marrow) volume Example 37

Bone Histomorphometry in Concurrent MIA-induced Osteoarthritis Model

Male Sprague-Dawley (SD) rats weighing 170~230 g (6 weeks of age) were purchased and acclimated for one week. One day before disease induction, animals were randomized into four group of Normal, Vehicle, Diclofenac (10 mg/kg) and GM (500 mg/kg). Anesthetized rats were injected with 0.8 mg of MIA in 50 μl saline solution into the intra-articular pocket at 1 hour after sample treatments. Samples were administrated daily with gastric tube for 6 weeks.

Bone histomorphometry was evaluated on both femur and tibia per knee joint by Micro CT scan using an Inveon™ unit (Siemens Healthcare USA, Inc., Pennsylvania, USA) at Korea Basic science institute, Ochang, Korea. BV/TV as an indicator of trabecular bone volume is the ratio of the trabecular bone volume to the total volume. BMD used as an indicator of osteoporosis and fracture risk.

As shown Table 24 and FIG. 1, BMD in both Diclofenac and GM group was significantly increased when compared to that of vehicle group. Both Diclofenac and GM groups had tendency to increase BV/TV values in comparison against vehicle group in MIA rats (Table 24; FIG. 1).

TABLE 24

Change in BMD and Bone Architecture in Concurrent MIA-Induced Model

|  | Normal | Vehicle | Diclofenac (10 mg/kg) | GM (500 mg/kg) |
|---|---|---|---|---|
| BMD (mg/cm3) | 1023.5 ± 8.3 | 881.9 ± 64.0 | 982.3 ± 19.44 | 996.1 ± 11.64 |
| BV/TV (%) | 74.76 ± 2.60 | 68.24 ± 5.03 | 71.89 ± 5.43 | 70.84 ± 5.92 |

Data represented as mean ± SD.
*p < 0.05 (vs vehicle).
BV/TV; total trabecular bone volume/total tissue (bone + marrow) volume Example 38

Clinical Trial Evaluating the Effect of *Morus alba* and *Acacia catechu* on Adults with Osteoarthritis This study examined the effect of an *Acacia/Morus* (1A: 2M) composition on discomfort (onset and overall) and overall function when taken for a 12-week period by individuals having osteoarthritis (OA) of the knee. In this study, 135 adults, aged 35 to 75 years, with BMI of less than 35 kg/m$^2$ who had knee pain for at least 15 of the 30 days prior to starting the study, had symptoms of knee pain for at least 6 months prior to starting the study, and had a Kellgren-Lawrence grade of I, II, or III according to a screening X-ray and met all the inclusion/exclusion criteria were enrolled after signing the informed consent. The study lasted approximately 12 weeks, with subjects seen at a screening visit and 6 study visits (at days 0, 7, 14, 28, 56 and 84). The screening visit also included an X-ray of the knee for determination of OA with Kellgren-Lawrence grades of I-III inclusionary (unless subject had an X-ray from the past 6 months). At the screening visit, subjects were provided with rescue medication (acetaminophen) and were asked to bring the unused rescue medication to each follow-up visit so that rescue medication usage could be determined.

The study subjects were randomized and administered one of the following three study articles:

Test Product—was comprised of *Morus alba* (White Mulberry) and *Acacia catechu* (Senegalia catechu) (100 mg per capsule), formulated with pharmaceutically acceptable carriers or excipients, including microcrystalline cellulose, magnesium stearate (vegetable) and silicon dioxide.

Positive Control—was comprised of a combination of glucosamine (375 mg) and chondroitin (300 mg), formulated with pharmaceutically acceptable carriers or excipients, including magnesium stearate (vegetable) and silicon dioxide.

Placebo—was comprised of pharmaceutically acceptable carriers or excipients, including microcrystalline cellulose, magnesium stearate (vegetable) and silicon dioxide Subjects were instructed to take two capsules with a morning meal and two capsules with an evening meal with up to 8 ounces of water, for a total of four capsules per day.

One efficacy measure was to determine the effect on discomfort when Test Product was used for 12 weeks as compared to Postive Control (glucosamine-chondroitin) and Placebo, as measured by: (a) Western Ontario and McMaster University Osteoarthritis Index (WOMAC) pain sub-score; (b) Visual Analog Scale (VAS)-Discomfort ratings (ratings over 12 weeks); and (c) rescue medication use (over 12 weeks).

A second efficacy measure was to determine the acute effect on discomfort over the first 7 days of use of Test Product as compared to Postive Control and Placebo, as measured by: (a) Visual Analog Scale (VAS)-Discomfort ratings (daily ratings over the first 7 days of product use); and (b) rescue medication use (over the first 7 days of product use).

A third efficacy measure was to determine the effect on overall function when Test Product was used for 12 weeks as compared to Postive Control and Placebo, as measured by: (a) Western Ontario and McMaster University Osteoarthritis Index (WOMAC) stiffness and activities of daily living sub-scores; (b) Range of Motion Goniometer Testing; and (c) Six Minute Walk Test (6MWT).

A fourth efficacy measure was to determine the effects on inflammation and bone metabolism when Test Product was used for 12 weeks as compared to Postive Control and Placebo, as measured by production of the following various biomarkers: (a) tumor necrosis factor-alpha (TNFα); (b) Interleukin-1 beta (IL-1β), (c) Interleukin-10 (IL-10), and (d) urinary CTX-II.

The main efficacy analysis was conducted on a Per-Protocol (PP) basis, using the PP population because the attrition was well within the expected limit, so no intention-to-treat (ITT) analysis was necessary. For each continuous efficacy variable, the mean change from baseline to each subsequent time point within each product group was tested for nominal significance by the paired Student t test, or by the non-parametric Wilcoxon test if substantially non-normally distributed. For each continuous efficacy variable at each time point, and for changes from baseline to each subsequent time point, the values were tested for an overall difference between the three products by the one-way analysis of variance (ANOVA). For the analysis of the biomarkers (TNFα and CTX-II/CR), three approaches were used as follows: (1) non-parametric testing for any difference between the three groups (using the non-parametric Kruskal-Wallis test instead of the 1-way ANOVA); (2) parametric (ANOVA) and non-parametric (KW) testing between the three groups on the logarithms of the values; and (3) analysis of covariance (ANCOVA), for comparing mean changes from baseline between UP1306 and G+C, and between UP1306 and Placebo, adjusted for baseline value) on the logarithms of the values.

Safety of daily supplementation with UP1306 was determined based on changes from baseline to 12 weeks in blood work (comprehensive metabolic panel, complete blood count with differential and PT/INR), blood pressure (BP), heart rate (FIR), adverse events, and subjective remarks.

All safety analyses were conducted on the Safety population. For each continuous safety variable, the mean change (or mean percentage change) from baseline to each subsequent time point within each product group was tested for significance by the paired Student t test, or by the non-parametric Wilcoxon test if substantially non-normally distributed. For each continuous safety variable at each time point, the mean differences in the variable, and in the change in that variable from baseline, between the three different products was tested for significance by the one-way analysis of variance (ANOVA). For each categorical safety variable, the difference in the distribution of categories between the different test articles was tested for significance by the Fisher Exact test if possible, or by the Chi-Square test if necessary. Adverse events (AEs) were listed, MedDRA encoded, grouped by general type of event (gastrointestinal, neurologic, cardiac, etc.), and cross-tabulated by event type and product group. Differences in AE patterns between test articles were measured by the Fisher Exact test. Subjective remarks were categorized to the extent possible, and analyzed for pattern differences between product groups in the same way as AEs.

Results

Safety

There were no changes of clinical significance for any of the safety endpoints (e.g. blood pressure, heart rate and safety lab values). There was also no significant association between the test product and frequency of occurrence of adverse events. No serious adverse events (SAEs) were observed during the course of this study.

A total of 43 adverse events (AEs) were observed among 30 of the 133 subjects in the Safety population. Fifteen (15) of the 43 AEs were observed in the subjects in the Test Product (*Morus/Acacia*) group, ten (10) of the 43 AEs were observed in the subjects in the Postive Control (glucosamine and chondroitin combination) group, and 18 of the 43 AEs were observed in the subjects in the Placebo group.

Fourteen (14) of the 43 total AEs, among seven subjects, were considered probably or possibly related to the Test Product; the other one was considered unlikely or definitely not related to the Test Product. Among the 14 probably or possibly related AEs, three (3) AEs occurred among two of the subjects in the Test Product group; two AEs occurred among two of the subjects in the Postive Control group; and 9 AEs occurred among three of the subjects in the Placebo group.

Overall, there were no safety concerns raised with the Test Product.

Efficacy

There were significant improvements from baseline to most time-points for all efficacy measures within groups. The two significant differences observed between the Test Product and the controls were the following:

WOMAC Pain: significant decrease from baseline to Day 56 for Test Product over the Positive Control ($p=0.048$).

Urine CTX-II: significant difference between the changes for Test

Product and Placebo after 12 weeks of use ($p=0.029$).

Based on the data from this study, the high rate of response for the Placebo group made it difficult to extract statistically significant data between the three groups as the response rate was favorable for all three study groups. The subject reported outcomes (WOMAC, VAS) failed to show statistical significance other than one time point for Test Product (Day 56 for UP1306 over the Positive Control ($p=0.048$)), but the objective biomarkers, such as CTXII, met the objective by showing significant difference between the Test Product and Placebo after 12 weeks product use ($p=0.029$).

As noted above, the measure of the following biomarkers: (a) tumor necrosis factor-alpha (TNFα); (b) Interleukin-1 beta (IL-1β), (c) Interleukin-10 (IL-10), and (d) urinary CTX-II, was used as a surrogate measure of the effect Test Product had on inflammation and bone metabolism when used for 12 weeks, as compared to Positive Control and Placebo. The values for interleukin-1 beta (IL-1β), interleukin-10 (IL-10) were below the limits of quantitation for the majority of the subjects resulting in a small data set; therefore, these were not analyzed. In addition, tumor necrosis factor-alpha (TNFα) showed no statistically significant changes in scores within group for any of the three tested articles, including no statistically significant difference in the change from baseline to day 84 between groups (data not shown).

Measurement of Urinary CTX-II at Baseline and at Day 84

CTX-II measurements Urinary levels of collagen type II C telopeptide fragments were measured by the CartiLaps ELISA assay. The assay uses a highly specific monoclonal antibody for the detection of degradation products of C-terminal telopeptide of type II Collagen. The assay is based on the competitive binding of the monoclonal antibody to urinary fragments of type II collagen.

The concentration of the CTX-II ELISA (ng/l) was standardized to the total urine creatinine (mmol/l): concentration/creatinine=ng/mmol. Creatinine concentration was measured using a creatinine Colorimetric assay kit (Cayman Chemical) that relies on the Jaffe's reaction. CTX-II biomarker values were not normally distributed and consequently the mean values and standard deviations were calculated by non-parametric statistics.

TABLE 25

Urinary CTX-II/CR (ng/mmol), by Product, by Visit, all Subjects (Actual Values)*

| Visit | Test Product | Positive Control | Placebo |
|---|---|---|---|
| Visit 2 | 414 ± 231 (44) | 403 ± 310 (45) | 339 ± 208 (44) |
| Randomization | 364 (131 – 1,117) | 342 (70 – 1,894) | 263 (92 – 888) |
| Visit 7 Day 84 | 377 ± 296 (44) | 404 ± 233 (45) | 417 ± 266 (43) |
|  | 301 (87 – 1,890) | 357 (48 – 1,216) | 305 (126 – 1,129) |
| Change from | −37 ± 319 (44) | 2 ± 303 (45) | 85 ± 238 (43) |
| Baseline to Day 84 | −23 (−667 – 1,372) | 9 (−1,174 – 605) | 6 (−277 – 791) |

*analysis using log transformed values

TABLE 26

Urinary CTX-II/CR (ng/mmol), by Product by Visit, in PP Population

| | | | | 3-group Comp | | ANCOVA | |
|---|---|---|---|---|---|---|---|
| Visit | Test Product | Positive Control | Placebo | par ANOVA | Non-par KW | TP vs. PC | TP vs. Pla |
| Visit 2 | 5.88 ± 0.53 (43) | 5.77 ± 0.67 (44) | 5.68 ± 0.60 (41) | 0.332 | 0.340 (np) | | |
| Rand | 5.89 (4.88-7.02) | 5.82 (4.25-7.55) | 5.61 (4.53-6.79) | | | | |

TABLE 26-continued

Urinary CTX-II/CR (ng/mmol), by Product by Visit, in PP Population

| | | | | 3-group Comp | | ANCOVA | |
| --- | --- | --- | --- | --- | --- | --- | --- |
| Visit | Test Product | Positive Control | Placebo | par ANOVA | Non-par KW | TP vs. PC | TP vs. Pla |
| Visit 7 | 5.74 ± 0.61 (43) | 5.81 ± 0.64 (44) | 5.91 ± 0.57 (40) | 0.428 | 0 499 (np) | | |
| Day 84 | 5.71 (4.47-7.54) | 5.86 (3.87-7.1) | 5.75 (4.9-7.03) | | | | |
| Change from Rand to Day 84 | −0.14 ± 0.62 (43) −0.08 (−1.69-1.3) p = 0.165 (np) | 0.04 ± 0.66 (44) 0.03 (−1.26-1.6) p = 0.804 (np) | 0.25 ± 0.64 (40) 0.13 (−0.75-2.03) p = 0.042 (np) | 0.025 | 0.070 (np) | 0.327 | 0.029 |

*analysis using log transformed values

There was a statistically significant difference between the changes for Test Product and Placebo after 12 weeks of product use (p=0.029).

Urinary CTX-II levels are useful for detecting populations at high risk of joint damage progression early in the disease. These data also indicate that in these patients with increased bone/cartilage degradation, even in the absence of severe joint damage, early intervention with products aimed at reducing both bone and cartilage degradation—in combination, for example, with an anti-inflammatory therapy—may help to prevent subsequent joint damage. These findings have important clinical implications for the management of OA, RA and other cartilage degradation related conditions.

Example 39

Preparation of Composition UP1306

Dried Moms alba root barks were cut, crushed, and then extracted with approximately seven-fold volume of 70% ethyl alcohol in water at 100° C. for 4 hrs three times to give Moms alba 70% EtOH extract powder with a yield of 19.6% (w/w). The standardized moms extract contains no less than 4% Mulberroside A and no less than 3% of total bioflavonoids including Kuwanon G, Albanin G and Morusin. Catechins enriched *Acacia* extract was obtained by repeated crystallization from the aqueous extract of *Acacia catechu* heartwood with a yield of 14.5% (w/w). (+)-Catechin was identified as the major active flavan in the *A. catechu* extract. The *Acacia* extract was standardized as no less than 65% of catechin and a minor enantiomer epicatechin. Compositions UP1306 or AmLexin was prepared by mixing the standardized extracts of *Acacia catechu* heartwood (no less than 65% catechins) and *Morus alba* root bark (no less than 7% stilbenes and bioflavonoids) at a ratio of 1:2 by weight with no less than 15% catechins and 2% stilbenes and bioflavonoids.

Example 40

Preparation Of Composition UP446

The *Scutellaria baicalensis* extract was prepared by extraction of dried *Scutellaria baicalensis* roots powder with water and then recrystallization to give the final product containing baicalin as the major bioflavonoid at content not less than 75% as well as other minor free-B-ring flavonoids such as wogonin-7-O-glucuronide, oroxylin A-7-O-glucuronide, and baicalein. *Acacia* extract was obtained from repeated crystallization of an aqueous extract of the heartwoods of an India medicinal plant, *A. catechu*. (+)-Catechin is the major component in the *A. catechu* extract with a content of not less than 65% plus a minor amount of its enantiomer, epicatechin, as well as other minor amounts of flavans. Composition UP446 was a mixture of the *S. baicalensis* and *A. catechu* standardized extracts at a ratio 4:1 with baicalin content not less than 60% and catechin content not less than 10%. Other minor flavonoids, such as wogonin 7-glucuronide and baicalein, account for about 15% of total weight.

Example 41

Preparation of Organic and Aqueous Extracts from *Morus alba*, *Acacia catechu*, and *Scutellaria baicalensis*

Plant materials from *Morus alba* L. root barks, *Acacia catechu* (L) Wild barks and *Scutellaria baicalensis* roots were ground to a particle size of no larger than two millimeters (mm). Each dried ground plant material (60 grams) was then transferred to an Erlenmeyer flask and Methanol:Dichloromethane (1:1 volume ratio) (600 milliliters (mL)) was added. The mixture was shaken for one hour, filtered and the biomass was extracted again with Methanol:Dichloromethane (1:1 volume ratio) (600 mL). These organic extracts were combined and evaporated under vacuum to provide organic extracts (OE) (See Table 27). After organic extraction, the biomass was air dried and extracted once with ultrapure water (600 mL). The aqueous solution was filtered and freeze-dried to provide aqueous extracts (AE) (See Table 27).

Similar results were obtained using the same procedure, but with the organic solvent being replaced with methanol or ethanol to provide a methanol extract (ME) or ethanol extract (EE), respectively. Other species and parts of plants and marine sample were extracted using this same procedure.

TABLE 27

| Plant source | Amount (g) | Organic extract (g) | Aqueous extract (g) |
| --- | --- | --- | --- |
| *Acacia catechu* | 60 | 27.2 | 10.8 |
| *Scutellaria baicalensis* | 60 | 9.18 | 7.18 |
| *Morus alba* | 60 | 3.55 | 4.44 |

Example 42: Animals

Sprague-Dawley rats were purchased form Charles River Laboratories (Hollister, CA, USA) at the age of 8 weeks and were acclimated upon arrival for a week before being assigned randomly to their respective groups. Rats (3/cage) were housed in a polypropylene cage and individually identified by numbers on their tails. Each cage was covered with wire bar lid and filtered top (Allentown, NJ, USA). Each individual cage was identified with a cage card indicating project number, test article, dose level, group, and animal numbers. The Harlan T7087 soft cob beddings were used and changed at least twice a week. Animals were provided with fresh water and rodent chow diet # T2018 (Harlan Teklad, 370W, Kent, WA, USA) ad libitum and were housed in a temperature-controlled room (22.2° C.) on a 12 h light-dark cycle. All animal experiments were conducted according to the institutional guidelines congruent with guide for the care and use of laboratory animals.

Example 43: Mono-Iodoacetate (MIA)-Induced Experimental Osteoarthritis Model Induction and Treatment Treatment started a week before MIA injection. Animals (body weight 215-229 g) were randomized into six groups of 10 rats per group as G1=normal, G2=vehicle (0.5% CMC-Na solution), G3=Diclofenac (10 mg/kg, Lot #W08B043, Ward Hill, MA), G4=UP1306 (400 mg/kg) (Lot #AM14002), G5=UP446 (250 mg/kg), and G6=Composition–UP1306 (400 mg/kg)+UP446 (250 mg/kg) were orally gavaged with respective treatment. The standardized blends for each treatment groups are defined as UP446=1A:4S, UP1306=1A:2M and the composition at the given dosage=0.282A:0.308S:0.410M where "A", "S" and "M" stands for acacia, scutellaria and moms, respectively. On the induction day, isoflurane (Lot #B66H15A, Piramal Enterprise Ltd. Andhra Pradesh, India) anesthetized rats were injected with 0.8 mg of MIA (Lot #A0352046, Acros Organics, New Jersey, USA) in 50 µL saline solution into the intra-articular pocket of left femorotibial (knee) joint using 26 G needle an hour after treatment. Normal control rats were injected with an equal volume of saline. Paw withdrawal thresholds as a result of constant pressure applied to the affected joint as a measure of pain sensitivity were taken once a week using Randall-Salitto Anesthesiometer (IITC, USA) and treatment lasted for 6 weeks. Body weights were measured once a week to calculate the respective weekly dosage of each group. The merit of combining UP1306 and UP446 was then evaluated using the Colby's equation (Colby, 1967). Pain sensitivity percent inhibition values were used to determine the calculated efficacy values and compared to the observed percent inhibition values of the composition.

Example 44: Histopathology Procedures and Evaluations

At necropsy, animals were asphyxiated with $CO_2$ and the femorotibial joint was carefully dissected out, fixed in 10% buffered formalin and sent to Nationwide Histology (Veradale, WA, USA) for further histopathology analysis. The fixed specimens were then decalcified with Calci-Clear Rapid for 1 and a half days and embedded in paraffin. Standardized 5 µm serial sections were obtained at the medial and lateral midcondylar level in the sagittal plane and were stained with hematoxylin and eosin (HE) and Safranin O-fast green to enable evaluation of proteoglycan content. A modified Mankin system (Mankin et al., 1981) was used to score structural and cellular alterations of articular components as indications of disease progression and/or treatment efficacy. The histological analysis was conducted by a certified Pathologist at Nationwide Histology.

Example 45: CTX-II ELISA Assay

CTX-II ELISA was performed according to the kit manufacturer's specifications. Briefly, a standard curve was prepared by generating serial dilutions (1:2) of CTX-II standard (5000 pg/mL) in Sample Diluent. Rat urine samples were thawed on ice and diluted 1:3 with Sample Diluent. 100 µL of samples and standards were added to a 96-well plate pre-coated with CTX-II antibody. The plate was covered and incubated at 37° C. for 2 hours. The liquid was aspirated from each well, then 100 µL of Detection Reagent A working solution was added to each well. The plate was covered and incubated at 37° C. for 1 hour. The solution was aspirated from each well and the plate was washed three times with 1× Wash Buffer. 100 µL of Detection Reagent B working solution was added to each well, then the plate was covered and incubated at 37° C. for 1 hour. The solution was aspirated from each well and the plate was washed five times with 1× Wash Buffer. 90 µL of Substrate Solution was added to each well, then the plate was covered and incubated at 37° C. for 30 minutes. 50 of Stop Solution was added to each well, and the optical density at 450 nm was detected using a Tecan Genios plate reader. CTX-II concentrations for each sample were determined by multiplying by the dilution factor and fitting the value to the standard curve. To offset the variations in urine flow between rats, values were normalized to total urine protein.

Example 46: Anti-Pain Sensitivity Activity of Compositions in MIA-Induced OA Model Pain, one of the main cardinal symptoms of OA was evidenced a week following model induction. As seen in Table 27, rats with an intra-articular injection of MIA without treatment showed progressive increase in pain sensitivity as exhibited by the mean pain sensitivity values. Compared to the vehicle treated normal control animals, rats with intraarticular 0.8 mg/joint MIA showed 44.9, 45.4, 47.7, 46.5 and 47.1% increase in pain sensitivity from week-1 to week-5, respectively. In contrast, all treatment groups showed statistically significant inhibition in pain sensitivity for all the weeks (Table 28 and 29). The highest inhibition in pain sensitivity was observed for rats treated with 650 mg/kg of the composition followed by the 325 mg/kg. These reductions were compared against the vehicle treated group and found as 47.9%, 53.8%, 64.4%, 60.7% and 62.5% from week 1 to week-5, respectively, for rats treated with UP1306 and UP446 composition at oral doses of 650 mg/kg/day. Rats administered with UP446 at 250 mg/kg experienced greater inhibition in pain sensitivity than UP1306 at 400 mg/kg (Table 28 and 29). The observed pain reliefs were statistically significant at each data point examined for both the studies for all the treatment groups.

TABLE 28

Compression threshold for MIA-injected rats treated with UP1306, UP446 and their composition

| Group | Dose (mg/kg) | N | Compression threshold (Mean ± SD) | | | | | |
|---|---|---|---|---|---|---|---|---|
| | | | Baseline | Week-1 | Week-2 | Week-3 | Week-4 | Week-5 |
| Control | 0 | 10 | 243.9 ± 1.8 | 246.5 ± 5.0 | 244.5 ± 2.3 | 247.8 ± 2.5 | 245.0 ± 1.9 | 246.4 ± 1.8 |
| MIA+ | 0 | 10 | 246.2 ± 3.3 | 135.9 ± 2.6 | 133.4 ± 1.9 | 129.6 ± 1.6 | 131.2 ± 3.6 | 130.4 ± 1.9 |
| Diclofenac | 10 | 10 | 244.1 ± 3.8 | 190.8 ± 1.1 | 171.8 ± 0.6 | 170.1 ± 2.2 | 171.6 ± 0.6 | 170.9 ± 1.1 |
| UP1306 | 400 | 10 | 243.5 ± 3.8 | 159.2 ± 3.0 | 164.8 ± 1.1 | 168.7 ± 3.4 | 173.4 ± 3.0 | 174.5 ± 1.7 |
| UP446 | 250 | 10 | 243.1 ± 2.2 | 175.2 ± 3.5 | 170.9 ± 1.2 | 174.6 ± 5.8 | 180.5 ± 5.2 | 183.6 ± 4.5 |
| Composition | 650 | 10 | 242.8 ± 1.6 | 201.9 ± 2.7 | 205.2 ± 5.0 | 213.2 ± 9.7 | 210.8 ± 1.3 | 212.0 ± 5.3 |

Composition: UP1306 + UP446

TABLE 29

Percent change of pain sensitivity against vehicle treated MIA-induced rats

| Group | Dose (mg/kg) | N | Percent change of vehicle Pain sensitivity inhibition | | | | | |
|---|---|---|---|---|---|---|---|---|
| | | | Baseline | Week-1 | Week-2 | Week-3 | Week-4 | Week-5 |
| Diclofenac | 10 | 10 | 0.9 | 40.4* | 28.8* | 31.2* | 30.8* | 31.0* |
| UP1306 | 400 | 10 | 1.1 | 17.1* | 23.6* | 30.1* | 32.1* | 33.8* |
| UP446 | 250 | 10 | 1.2 | 28.9* | 28.1* | 34.7* | 37.6* | 40.8* |
| Composition | 650 | 10 | 1.4 | 47.9* | 53.8* | 64.4* | 60.7* | 62.5* |

*$P \leq 0.001$;
Composition: UP1306 + UP446

Example 46: Unexpected Pain Reduction Synergistic Activity a Composition Comprised of *Morus, Acacia* and *Scutellaria* Extracts The merit of combining UP1306 and UP446 at the indicated dosages for pain relief was also assessed using Colby's equation. In this method, for a formulation of two or more materials together will presume to have unexpected synergy, when the observed value of a certain end point measurement is greater or equal to the hypothetically calculated values. In this study, pain sensitivity was used as the end point measurement for synergy determination. As seen in Table 30, the observed pain inhibitions were greater than the expected for the composition at each week administered at oral doses of 650 mg/kg.

TABLE 30

Unexpected synergistic effect of UP1306 and UP446 combination in reducing pain sensitivity

| Dose (mg/kg) | | UP1306 + UP446 | | | | |
|---|---|---|---|---|---|---|
| | | wk1 | wk2 | wk3 | wk4 | wk5 |
| 250 | UP446 | 28.9 | 28.1 | 34.7 | 37.6 | 40.8 |
| 400 | UP1306 | 17.1 | 23.6 | 30.1 | 32.1 | 33.8 |
| | (x + y) | 46.0 | 51.7 | 64.8 | 69.7 | 74.6 |
| | (xy)/100 | 4.9 | 6.6 | 10.4 | 12.1 | 13.8 |
| 650 | Expected | 41.1 | 45.1 | 54.4 | 57.6 | 60.8 |
| | Observed (Composition) | 47.9 | 53.8 | 64.4 | 60.7 | 62.5 |

Example 47: Improved Histological Findings as a Result of a Composition Comprised of *Morus, Acacia* and *Scutellaria* Extracts in MIA-Induced OA Model Complementing the pain sensitivity reduction data, statistically significant improvements in articular cartilage matrix integrity were shown as reflected by the modified total Mankin score for animals treated with the compositions and their active constituents.

Structural abnormalities and fibrovascular proliferation were also significantly reduced in this group. When the overall structural abnormality (such as cartilage thickening or thinning, surface irregularity, fissure loss, degeneration, ulcerative necrosis, sever disorganization and chaotic appearance) was assessed, reductions of 38.3, 60.5, and 56.5% were observed for rats treated with AM (400 mg/kg), UP446 (250 mg/kg) and AU (650 mg/kg), respectively (Table 31). Diclofenac showed a 51.4% reduction in structural abnormalities (Table 31). The highest inhibition (80.8%) in inflammation and infiltration of inflammatory cells was observed for rats treated with AU at 650 mg/kg as compared to the 37.7% and 53.8% inhibitions from its constituents AM and UP446, respectively (Table 31).

The extent of osteoclast activities and subchondral bone damage were minimal. In contrast, various degrees of histopathological changes including cellular degeneration and disorganization of the articular cartilage chondrocytes, depletion and collapse of the intracellular matrix, articular surface irregularities, osteophyte remodeling, and fibrillation of the subchondral bone were observed for MIA-injected rats treated with vehicle. These changes are similar to the most common findings in human OA biology (Loeser et al., 2013). In Safranin O staining, articular cartilage of treatment groups revealed minimum loss of staining intensity indicating its ability to spare cartilage degradation (Table 31). For instance, reductions of 46.0, 31.0, 59.7 and 57.1% were observed in matrix GAG loss for Diclofenac (10 mg/kg), AM (400 mg/kg), UP446 (250 mg/kg) and AU (650 mg/kg), respectively. Rats in the normal control groups treated with vehicle showed negligible changes in all the parameters examined (Table 31). Normal structure of the articular cartilage, subchondral bone of both tibia plateaus and femoral bone, and the surrounding joint structure appeared intact in this group of rats.

TABLE 31

Modified Mankin scoring system for histopathological findings for MIA-induced rats treated with UP1306, UP446 and their composition

| Group | Dose (mg/kg) | MIA mg/joint | N | Structural abnormality | Bone at Articular surfaces | Inflammation/ Cellular infiltration | Fibrovascular proliferation | Matrix GAGs |
|---|---|---|---|---|---|---|---|---|
| Control– | 0 | 0 | 10 | 1.15 ± 0.61† | 0.90 ± 0.58† | 0.75 ± 0.34* | 1.35 ± 0.63* | 1.36 ± 0.67† |
| MIA+ | 0 | 0.8 | 10 | 2.53 ± 0.79 | 1.90 ± 0.70 | 1.30 ± 0.68 | 2.40 ± 1.02 | 2.68 ± 0.76 |
| Diclofenac | 10 | 0.8 | 10 | 1.23 ± 0.36‡ | 0.70 ± 0.24‡ | 0.55 ± 0.15† | 1.55 ± 0.69* | 1.44 ± 0.38‡ |
| UP1306 | 400 | 0.8 | 10 | 1.56 ± 0.38† | 1.35 ± 0.50 | 0.81 ± 0.50 | 1.60 ± 0.83 | 1.85 ± 0.37* |
| UP446 | 250 | 0.8 | 10 | 1.00 ± 0.40‡ | 1.05 ± 0.47* | 0.60 ± 0.20* | 1.75 ± 0.64 | 1.08 ± 0.34‡ |
| Composition | 650 | 0.8 | 10 | 1.10 ± 0.51‡ | 0.70 ± 0.60† | 0.25 ± 0.25‡ | 1.85 ± 0.71 | 1.15 ± 0.46‡ |

*P ≤ 0.05;
†P ≤ 0.001;
‡P ≤ 0.0001;
AM-UP1306, Composition-UP1306 + UP446.
MIA—monoiodoacetate.
Structural abnormality (0-6): Cartilage thickness/thinning, irregular surface frayed/fissure loss, degeneration, ulcerative necrosis/fragmentation, severe disorganization/chaotic;
Bone at the articular surfaces (0-6): Subchondral bone thickness/volume & density, osteoclastic activity, subchondral bone damage;
Inflammation/Cellular infiltration (0-6): Cellular Infiltration/Inflammation & Proliferation, hypercellular, cluster/hypocellular;
Fibrovascular proliferation (0-6): Fibrovascular Proliferation replacing periarticular/capsul/bone (Pannus), condyle &/or tibial plateau, menicus reduction, fusion, adhesion;
Matrix GAGs (0-6): Matrix GAGs reduction: radial, interterritorial to pericellular loss of staining, femoral condyle/tibial plateau-integrity & thickness of articular Cartilage.

Example 48: Significant Reductions in Urine CTX-II Level as a Result of the Composition Urine CTX-II (C-telopeptide of type II collagen), is a type II collagen biomarker frequently referenced for its close correlation with progression of articular cartilage degradations. After 5 weeks of daily oral treatment, 31.33 and 31.94% reductions in urine CTX-II were observed for rats treated with diclofenac (10 mg/kg) and UP1306+UP446 (650 mg/kg) (Table 32). This inhibition of cartilage degradations and hence low level of urine CTX-II, were statistically significant for rats treated with the composition. On the other hand, UP1306 and UP446 treated rats showed a 21.93 and 17.38% reduction in uCTX-II, respectively.

TABLE 32 uCTX-II normalized to total protein at week 5.

| Group | Dose (mg/kg) | N | uCTX-II (ng/L) (Mean ± SD) | Total protein (g/L) (Mean ± SD) | Ratio (CTX-II/Protein) | P-values vs MIA+ |
|---|---|---|---|---|---|---|
| Control– | 0 | 5 | 365 ± 145 | 3.08 ± 1.02 | 118.39 | 0.332 |
| MIA+ | 0 | 15 | 635 ± 233 | 6.46 ± 2.64 | 98.30 | — |
| Diclofenac | 10 | 8 | 304 ± 233 | 4.72 ± 1.23 | 64.41 | 0.017 |
| UP1306 | 400 | 10 | 607 ± 237 | 7.91 ± 2.57 | 76.74 | 0.129 |
| UP446 | 250 | 10 | 614 ± 148 | 7.56 ± 2.34 | 81.22 | 0.103 |
| Composition† | 650 | 8 | 489 ± 172 | 7.66 ± 2.37 | 63.84 | 0.003 |

†Composition: UP1306 + UP446

Example 49

Immortalized chondrocytes grown in micromass culture exhibit a similar gene expression profile to chondrocytes in vivo. Treatment with IL-1β or TNF-α in this model induces a change to the gene expression profile of chondrocytes in OA, downregulating genes involved in cartilage synthesis, such as SOX9, COL2A1, and ACAN, and upregulating genes involved in cartilage degradation, such as ADAMTS5 and MMP13. This change in expression profile also leads to a reduction of glycosaminoglycans (GAGs) and collagen within the extracellular matrix (ECM) (Greco, 2011) (Schlichting, 2014). By pre-treating chondrocytes in micromass culture with AmLexin and UP446 individually as well as in combination before cytokine treatment, it can be determined whether the composition of the two compounds is more chondroprotective than the two separate formulations.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method for increasing bone density in a mammal in need thereof comprising administering an effective amount of a composition, wherein the composition comprising a mixture of at least one Morus extract enriched for one or more prenylated flavonoids, at least one Scutellaria extract enriched for one or more free-B-ring flavonoids, and at least one Acacia extract enriched for one or more flavans, wherein the Morus extract, the Scutellaria extract, and the Acacia extract are blended in a 1.3:1:1 weight ratio.

2. The method for increasing bone density in a mammal in need thereof of claim 1, wherein the Morus extract is from Morus alba, the Scutellaria extract is from Scutellaria baicalensis, and the Acacia extract is Previously from Acacia catechu.

3. The method for increasing bone density in a mammal in need thereof of claim 1, wherein the Acacia extract comprises 0.01% to 99.9% flavans.

4. The method for increasing bone density in a mammal in need thereof of claim 1, wherein the *Morus* extract comprises 0.1% to 49.9% prenylated flavonoids.

5. The method for increasing bone density in a mammal in need thereof of claim 1, wherein the *Scutellaria* extract comprises 0.01% to 99.9% free-B-ring flavonoids.

6. The method for increasing bone density in a mammal in need thereof of claim 1, wherein the one or more prenylated flavonoids comprises is Albanin G, Kuwanon G, Morusin, or any combination thereof.

7. The method for increasing bone density in a mammal in need thereof of claim 1, wherein the one or more flavans comprises catechin, epicatechin, or a combination thereof.

8. The method for increasing bone density in a mammal in need thereof of claim 1, wherein the composition additionally comprises a glucosamine-type compound.

9. The method for increasing bone density in a mammal in need thereof of claim 8, wherein the glucosamine-type compound comprises glucosamine sulfate, glucosamine hydrochloride, N-acetylglucosamine, chondroitin sulfate methylsulfonylmethane, and hyaluronic acid.

10. The method for increasing bone density in a mammal in need thereof of claim 1, wherein the composition further comprises a pharmaceutically or nutraceutically acceptable carrier, diluent, or excipient, wherein the pharmaceutical or nutraceutical formulation comprises from about 0.5 weight percent (wt %) to about 90 wt % of active ingredients of the extract mixture.

11. The method for increasing bone density in a mammal in need thereof of claim 10, wherein the composition is formulated as a tablet, hard capsule, softgel capsule, powder, or granule.

* * * * *